(12) United States Patent
Shvartsbart et al.

(10) Patent No.: US 11,306,079 B2
(45) Date of Patent: Apr. 19, 2022

(54) 3-(5-AMINO-PYRAZIN-2-YL)-BENZENESULFONAMIDE DERIVATIVES AND RELATED COMPOUNDS AS PI3K-GAMMA KINASE INHIBITORS

(71) Applicant: Incyte Corporation, Wilmington, DE (US)

(72) Inventors: Artem Shvartsbart, Kennett Square, PA (US); Andrew P. Combs, Kennett Square, PA (US); Nikoo Falahatpisheh, Wilmington, DE (US); Padmaja Polam, Kennett Square, PA (US); Lixin Shao, Wilmington, DE (US); Stacey Shepard, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 152 days.

(21) Appl. No.: 16/955,240

(22) PCT Filed: Dec. 20, 2018

(86) PCT No.: PCT/US2018/066805
§ 371 (c)(1),
(2) Date: Jun. 18, 2020

(87) PCT Pub. No.: WO2019/126505
PCT Pub. Date: Jun. 27, 2019

(65) Prior Publication Data
US 2020/0331903 A1 Oct. 22, 2020

Related U.S. Application Data

(60) Provisional application No. 62/608,896, filed on Dec. 21, 2017.

(51) Int. Cl.
| | | |
|---|---|---|
| *C07D 417/04* | (2006.01) | |
| *C07D 417/14* | (2006.01) | |
| *C07D 403/04* | (2006.01) | |
| *C07D 403/14* | (2006.01) | |
| *C07D 401/14* | (2006.01) | |
| *C07D 493/08* | (2006.01) | |
| *C07D 487/08* | (2006.01) | |
| *C07D 413/04* | (2006.01) | |

(52) U.S. Cl.
CPC ......... *C07D 417/04* (2013.01); *C07D 401/14* (2013.01); *C07D 403/04* (2013.01); *C07D 403/14* (2013.01); *C07D 413/04* (2013.01); *C07D 417/14* (2013.01); *C07D 487/08* (2013.01); *C07D 493/08* (2013.01); *C07B 2200/05* (2013.01)

(58) Field of Classification Search
CPC .. C07D 417/04; C07D 401/14; C07D 403/04; C07D 403/14; C07D 413/04; C07D 417/14; C07D 487/08; C07D 493/08; C07B 2200/05

USPC ...................................................... 514/210.2
See application file for complete search history.

(56) References Cited

U.S. PATENT DOCUMENTS

| | | |
|---|---|---|
| 5,521,184 A | 5/1996 | Zimmermann |
| 2004/0186148 A1 | 9/2004 | Shanker et al. |
| 2007/0225286 A1 | 9/2007 | Ren et al. |
| 2008/0039450 A1 | 2/2008 | Jensen et al. |
| 2009/0163463 A1 | 6/2009 | Bruce et al. |
| 2012/0214800 A1 | 8/2012 | Bruce et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2014/0051681 A1 | 2/2014 | Augeri et al. |
| 2014/0187529 A1 | 7/2014 | Shetty et al. |
| 2016/0311809 A1 | 10/2016 | Charrier et al. |
| 2017/0037032 A1 | 2/2017 | Bellenie et al. |

(Continued)

FOREIGN PATENT DOCUMENTS

| | | |
|---|---|---|
| AR | 099436 | 7/2016 |
| WO | WO 2000/009495 | 2/2000 |

(Continued)

OTHER PUBLICATIONS

Atzrodt, "The Renaissance of H/D Exchange," Angew Chem Int Ed., 2007, 7744-7765.

(Continued)

*Primary Examiner* — Kristin A Vajda
(74) *Attorney, Agent, or Firm* — Fish & Richardson P.C.

(57) ABSTRACT

This application relates to compounds of Formula (I) or pharmaceutically acceptable salts thereof, which are inhibitors of PI3K-γ which are useful for the treatment of disorders such as autoimmune diseases, cancer, cardiovascular diseases, and neurodegenerative diseases.

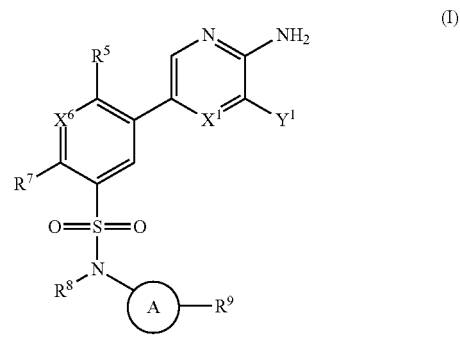

58 Claims, No Drawings

(56) References Cited

U.S. PATENT DOCUMENTS

| | | | |
|---|---|---|---|
| 2017/0042889 | A1 | 2/2017 | Bellenie et al. |
| 2018/0111916 | A1 | 4/2018 | Gray et al. |
| 2018/0170922 | A1 | 6/2018 | Charrier et al. |

FOREIGN PATENT DOCUMENTS

| | | |
|---|---|---|
| WO | WO 2000/053595 | 9/2000 |
| WO | WO 2001/014402 | 3/2001 |
| WO | WO 2001/064655 | 9/2001 |
| WO | WO 2002/000196 | 1/2002 |
| WO | WO 2003/024967 | 3/2003 |
| WO | WO 2003/037347 | 5/2003 |
| WO | WO 2003/099771 | 12/2003 |
| WO | WO 2004/005281 | 1/2004 |
| WO | WO 2004/046120 | 6/2004 |
| WO | WO 2004/056786 | 7/2004 |
| WO | WO 2004/080980 | 9/2004 |
| WO | WO 2005/028444 | 3/2005 |
| WO | WO 2006/056399 | 6/2006 |
| WO | WO 2009/007390 | 1/2009 |
| WO | WO 2009/096198 | 5/2011 |
| WO | WO 2015/120800 | 8/2015 |
| WO | WO 2015/162456 | 10/2015 |
| WO | WO 2015/162459 | 10/2015 |

OTHER PUBLICATIONS

Barber et al., "PI3Kgamma inhibition blocks glomerulonephritis and extends lifespan in a mouse model of systemic lupus," Nat Medicine, 2005, 9:933-935.
Berod et al., "PI3Kγ deficiency delays the onset of experimental autoimmune encephalomyelitis and ameliorates its clinical outcome," Euro J Immunol., 2011, 41(3):833-844.
Blom et al., "Optimizing Preparative LC-MS Configurations and Methods for Parallel Synthesis Purification," J Combi Chem., 2003, 5(5):670-683.
Blom et al., "Preparative LC-MS Purification: Improved Compound Specific Method Optimization," J Combi Chem., 2004, 6(6):874-883.
Blom, "Two-Pump At Column Dilution Configuration for Preparative LC-MS," J Combi Chem., 2002, 4(4):295-301.
Brock et al., "Roles of G beta gamma in membrane recruitment and activation of p110 gamma/p101 phosphoinositide 3-kinase gamma," J Cell Biol., 2003, 160(1):89-99.
Camps et al., "Blockade of PI3Kγ suppresses joint inflammation and damage in mouse models of rheumatoid arthritis," Nat Medicine, 2005, 11(9):936-943.
Cantley, "The phosphoinositide 3-kinase pathway," Science, 2002, 296(5573):1655-1657.
Carter et al., "Prioritization of driver mutations in pancreatic cancer using cancer-specific high-throughput annotation of somatic mutations (CHASM)," Cancer Biol Ther., 2010, 10(6):582-587.
Comerford et al., "PI3Kγ drives priming and survival of autoreactive CD4(+) T cells during experimental autoimmune encephalomyelitis," PLOS one, 2012, 7(9):e45095.
Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther., 2009, 328(3):758-765.
Doukas et al., "Phosphoinositide 3-kinase gamma/delta inhibition limits infarct size after myocardial ischemia/reperfusion injury," Proc Natl Acad Sci USA., 2006, 103(52):19866-19871.
El Khoury et al., "Ccr2 deficiency impairs microglial accumulation and accelerates progression of Alzheimer-like disease," Nat Med., 2007, 13(4):432-438.
Falasca and Maffucci, "Targeting p110gamma in gastrointestinal cancers: attack on multiple fronts," Frontiers in Physiology, 2014, 5(391):1-10.

Gennaro, "Preformulation," Remington's Pharmaceutical Sciences, 17th ed., Mack Publishing Company, Easton, Pa., 1985, 66:1418.
Giri et al., "Mechanism of amyloid peptide induced CCR5 expression in monocytes and its inhibition by siRNA for Egr-1," Am J Physiol Cell Physiol., 2005, 289(2):C264-C276.
Gonzalez-Garcia et al., "Phosphatidylinositol 3-Kinase γ Inhibition Ameliorates Inflammation and Tumor Growth in a Model of Colitis-Associated Cancer," Gastroenterology, 2010, 138:1374-1383.
Hanahan and Weinberg, "Hallmarks of Cancer: The Next Generation," Cell, 2011, 144(5):646-674.
Hayer et al., "PI3Kgamma regulates cartilage damage in chronic inflammatory arthritis," FASB J., 2009, 23(12):4288-4298.
International Preliminary Report on Patentability in International Application No. PCT/US2018/066805, dated Mar. 2, 2020, 7 pages.
International Search Report and Written Opinion in International Application No. PCT/US2018/066805, dated Feb. 26, 2019, 13 pages.
Jimenez et al., "The p85 regulatory subunit controls sequential activation of phosphoinositide 3-kinase by Tyr kinases and Ras," J Biol Chem., 2002, 277(44):41556-41562.
Kaneda et al., "PI3-kinase gamma controls the macrophage M1-M2 switch, thereby promoting tumor immunosuppression and progression," Cancer Res., Oct. 1, 2014, 74(Suppl 19):3650.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Laffargue et al., "Phosphoinositide 3-kinase gamma is an essential amplifier of mast cell function," Immunity, 2002, 16(3):441-451.
Li et al., "PI3Kγ inhibition alleviates symptoms and increases axon number in experimental autoimmune encephalomyelitis mice," Neuroscience, 2013, 253:89-99.
Lupia et al., "Ablation of phosphoinositide 3-kinase-gamma reduces the severity of acute pancreatitis," Am J Pathology., 2004, 165(6):2003-2011.
Martin et al., "PI3Kγ mediates Kaposi's sarcoma-associated herpesvirus vGPCR-induced sarcomagenesis," Cancer Cell, 2011, 19(6):805-813.
Passos et al., "Involvement of phosphoinositide 3-kinase gamma in the neuro-inflammatory response and cognitive impairments induced by beta-amyloid 1-40 peptide in mice," Brain Behav Immun., 2010, 24(3):493-501.
Pinho et al., "Phosphoinositide-3 kinases critically regulate the recruitment and survival of eosinophils in vivo: importance for the resolution of allergic inflammation," J Leukocyte Biology., 2005, 77(5):800-810.
Prete et al., "Defective dendritic cell migration and activation of adaptive immunity in PI3Kgamma-deficient mice," The EMBO Journal, 2004, 23(17):3505-3515.
Randis et al., "Role of PI3Kdelta and PI3Kgamma in inflammatory arthritis and tissue localization of neutrophils," Eur J Immunol., 2008, 38(5):1215-1224.
Rodrigues et al., "Absence of PI3Kgamma leads to increased leukocyte apoptosis and diminished severity of experimental autoimmune encephalomyelitis," J Neuroimmunol., 2010, 222(1-2):90-94.
Ruckle et al., "PI3Kgamma inhibition: towards an 'aspirin of the 21st century'?" Nat Rev Drug Discovery, 2006, 5(11):903-918.
Schmid et al., "PI3 Kinase gamma control of Arginase-1 expression promotes tumor immunosuppression," Cancer Res. 2012, 72(Suppl 1):Abstract 411.
Schmid et al., "Receptor tyrosine kinases and TLR/IL1Rs unexpectedly activate myeloid cell PI3kγ, a single convergent point promoting tumor inflammation and progression," Cancer Cell, 2011, 19(6):715-727.
Sigma-Aldrich, "L-α-Phosphatidyl-D-myo-inositol 4,5-diphosphate, dioctanoyl," CAS Reference No. 204858-53-7, retrieved Sep. 14, 2020, 2 pages.
Subramanjam et al., "Targeting nonclassical oncogenes for therapy in T-ALL," Cancer Cell, 2012, 21:459-472.
Thomas et al., "Airway inflammation: chemokine-induced neutrophilia and the class I phosphoinositide 3-kinases," Eur J Immunol., 2005, 35:1283-1291.

(56) References Cited

OTHER PUBLICATIONS

Vanhaesebroeck et al., "Signalling by PI3K isoforms: insights from gene-targeted mice," Trends Biochem Sci., 2005, 30(4):194-204.

Vecchione et al., "Protection from angiotensin II-mediated vasculotoxic and hypertensive response in mice lacking PI3Kgamma," J Exp Med., 2005, 201(8):1217-1228.

Xu et al., "Design, synthesis and biological evaluation of deuterated nintedanib for improving pharmacokinetic properties," J Label Compd Radiopharm., 2015, 58(7):308-312.

3-(5-AMINO-PYRAZIN-2-YL)-BENZENESULFONAMIDE DERIVATIVES AND RELATED COMPOUNDS AS PI3K-GAMMA KINASE INHIBITORS

TECHNICAL FIELD

The present invention provides bridged cyclic compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinopohils to airways and degranulation of mast cells (see e.g. Laffargue et al., Immunity, 2002, 16, 441-451; Prete et al., The EMBO Journal, 2004, 23, 3505-3515; Pinho et al., L. Leukocyte Biology, 2005, 77, 800-810; Thomas et al., Eur. J. Immunol. 2005, 35, 1283-1291; Doukas et al., J. Pharmacol. Exp Ther. 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., Am. J Pathology, 2004, 165, 2003-2011). PI3Kγ$^{-/-}$ mice were largely protected in four different models of rheumatoid arthritis (CIA, α-CII-IA, K/BxN serum transfer and TNF transgenic) and PI3Kγ inhibition suppressed the progression of joint inflammation and damage in the CIA and α-CII-IA models (see e.g., Camps et al., Nat. Medicine, 2005, 11, 939-943; Randis et al., Eur. J. Immunol, 2008, 38, 1215-1224; Hayer et al., FASB J., 2009, 4288-4298). In the MRL-lpr mouse model of human systemic lupus erythematous, inhibition of PI3Kγ reduced glomerulonephritis and prolonged life span (Barber et al., Nat. Medicine, 2005, 9, 933-935).

There is evidence suggesting that chronic inflammation due to infiltration by myeloid-derived cells is a key component in the progression of neurodegeneration diseases, such as Alzheimer's disease (AD) (Giri et al., Am. J. Physiol. Cell Physiol., 2005, 289, C264-C276; El Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced congnitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., J Neuroimmunol. 2010, 222, 90-94; Berod et al., Euro. J Immunol. 2011, 41, 833-844; Comerford et al., PLOS one, 2012, 7, e45095; Li et al., Neuroscience, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b$^+$ myeloid cells can cause protumorigenic inflammation at tumor sites and PI3Kγ in the myeloid cells is critical in mediating signaling of various chemoattractants in bring the cells to the tumor (Schmid et al., Cancer Cell, 2011, 19, 715-727). Other studies suggest that PI3Kγ is also required for differentiation of naïve myeloid cells into M2 macrophges at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., *Cancer Res.* 2012, 72 (*Suppl* 1: *Abstract,* 411; Kaneda et al., *Cancer Res.,* 74 (*Suppl* 19: *Abstact* 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., *Cancer Cell,* 2011, 19, 805-813). PI3Kγ was also suggested to be required for growth of T-ALL (Subramanjam et al., *Cancer Cell,* 2012, 21, 459-472), PDAC and HCC cells (Falasca and Maffucci, *Frontiers in Physiology,* 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., *Cancer Biol. Ther.* 2010, 10, 582-587).

Finally, PI3Kγ deficiency also has been reported to offer protection to experimental animals in different cardiovascular disease models. For examples, lack of PI3Kγ would reduce angiotension-evoked smooth muscle contraction and, therefore, protect mice from angiotension-induced hypertension (Vecchione et al., *J. Exp. Med.* 2005, 201, 1217-1228). In rigorous animal myocardial infarction models, PI3Kγ inhibition provided potent cardioprotection, reducing infarct development and preserving myocardial function (Doukas et al., *Proc. Nat. Acad. Sci. USA,* 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present invention related to, inter alia, compounds of Formula (I):

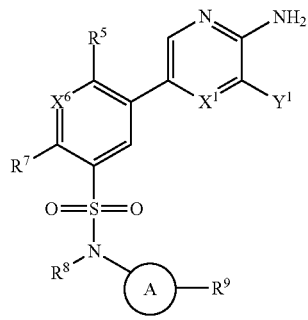

or pharmaceutically acceptable salts, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting an activity of PI3Kγ kinase comprising contacting the kinase with a compound of Formula (I), or a pharmaceutically acceptable salt thereof.

The present invention further provides methods of treating a disease or a disorder associated with abnormal PI3Kγ kinase expression or activity in a patient by administering to a patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

The present application provides, inter alia, a compound of Formula (I):

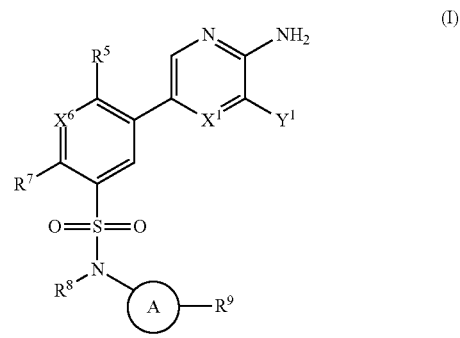

or a pharmaceutically acceptable salt thereof, wherein:

$X^1$ is N or $CR^1$;

$X^6$ is N or $CR^6$;

Ring A is a $C_{5-10}$ bridged bicycloalkyl or a 5-14 membered bridged biheterocycloalkyl, each of which is optionally substituted by 1, 2, 3, or 4 independently selected $R^2$ groups;

$Y^1$ is a $C_{6-10}$ aryl, $C_{3-10}$ cycloalkyl, 5-14 membered heteroaryl, or 4-14 membered heterocycloalkyl, wherein the $C_{6-10}$ aryl, $C_{3-10}$ cycloalkyl, 5-14 membered heteroaryl and 4-14 membered heterocycloalkyl of $Y^1$ are each optionally substituted with 1, 2, 3, or 4 independently selected $R^b$ substituents;

$R^1$, $R^5$, $R^6$, and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aC(O)R^a$, $NR^aC(O)OR^a$, $NR^aC(O)NR^aR^a$, $C(=NR^k)R^a$, $C(=NR^k)NR^aR^a$, $NR^aC(=NR^k)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)(=NR^k)R^a$, $SF_5$, —$P(O)R^aR^a$, —$P(O)(OR^a)(OR^a)$, $B(OR^a)_2$ and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 5-14 membered heterocycloalkyl-$C_{1-4}$ alkyl- of $R^1$, $R^5$, $R^6$ and $R^7$ are each optionally substituted with 1, 2, 3, or 4 independently selected $R^b$ substituents;

each $R^2$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{4-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^8$ is selected from H, D, CN, OH, $C_{1-6}$ alkyl, $C_{1-6}$ alkoxy, $C_{2-6}$ alkenyl, $C_{2-6}$ alkynyl, and $C_{1-6}$ haloalkyl;

$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, OR″, SR″, NHOR″, C(O)R″, C(O)NR″R″, C(O)OR″, OC(O)R″, OC(O)NR″R″, NR″R″, NR″C(O)R″, NR″C(O)OR″, NR″C(O)NR″R″, C(=$NR^k$)R″, C(=$NR^k$)NR″R″, NR″C(=$NR^k$)NR″R″, NR″C(=NOH)NR″R″, NR″C(=NCN)NR″R″, NR″S(O)R″, NR″S(O)$_2$R″, NR″S(O)$_2$NR″R″, S(O)R″, S(O)NR″R″, S(O)$_2$R″, S(O)(=$NR^k$)R″, $SF_5$, —P(O)R″R″, —P(O)(OR″)(OR″), B(OR″)$_2$ and S(O)$_2$NR″R″, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^9$ are each optionally substituted with 1, 2, 3, or 4 independently selected $R^m$ substituents;

each $R^a$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^k)R^c$, $C(=NR^k)NR^cR^c$, $NR^cC(=NR^k)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2 NR^cR^c$, $S(O)R^c$, $S(O)NR^cR^c$, $S(O)_2R^c$, $S(O)(=NR^k)R^c$, $SF_5$, —$P(O)R^cR^c$, —$P(O)(OR^c)(OR^c)$, $B(OR^c)_2$ and $S(O)_2 NR^cR^c$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^b$ is each optionally substituted with 1, 2, 3, or 4 independently selected $R^d$ substituents;

each $R^c$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^k)R^e$, $C(=NR^k)NR^eR^e$, $NR^eC(=NR^k)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2 NR^eR^e$, $S(O)R^e$, $S(O)NR^eR^e$, $S(O)_2R^e$, $S(O)(=NR^k)R^e$, $SF_5$, —$P(O)R^eR^e$, —$P(O)(OR^e)(OR^e)$, $B(OR^e)_2$ and $S(O)_2 NR^eR^e$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^d$ is each optionally substituted with 1, 2, 3, or 4 independently selected $R^f$ substituents;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^e$ is each optionally substituted with 1, 2, 3, or 4 independently selected $R^f$ substituents;

each $R^f$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^g$, $SR^g$, $NHOR^g$, $C(O)R^g$, $C(O)NR^gR^g$, $C(O)OR^g$, $OC(O)R^g$, $OC(O)NR^gR^g$, $NR^gR^g$, $NR^gC(O)R^g$, $NR^gC(O)OR^g$, $NR^gC(O)NR^gR^g$, $C(=NR^k)R^g$, $C(=NR^k)NR^gR^g$, $NR^gC(=NR^k)NR^gR^g$, $NR^gC(=NOH)NR^gR^g$, $NR^gC(=NCN)NR^gR^g$, $NR^gS(O)R^g$, $NR^gS(O)_2R^g$, $NR^gS(O)_2NR^gR^g$, $S(O)R^g$, $S(O)NR^gR^g$, $S(O)_2R^g$, $S(O)(=NR^k)R^g$, $SF_5$, —$P(O)R^gR^g$, —$P(O)(OR^g)(OR^g)$, $B(OR^g)_2$ and S(O)$_2$NR$^g$R$^g$, wherein the C$_{1-6}$ alkyl, C$_{1-6}$ alkoxy, C$_{2-6}$ alkenyl, C$_{2-6}$ alkynyl, C$_{1-6}$ haloalkyl, C$_{1-6}$haloalkoxy, C$_{6-10}$ aryl, C$_{3-10}$ cycloalkyl, 5-14 membered heteroaryl, 4-14 membered heterocycloalkyl, C$_{6-10}$ aryl-C$_{1-6}$ alkyl-, C$_{3-10}$ cycloalkyl-C$_{1-6}$ alkyl-, 5-14 membered heteroaryl-C$_{1-6}$ alkyl-, and 4-14 membered heterocycloalkyl-C$_{1-4}$ alkyl- of R$^f$ is each optionally substituted with 1, 2, 3, or 4 independently selected R$^h$ substituents;

each R$^g$ is independently selected from H, D, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-14 membered heterocycloalkyl, C$_{6-10}$ aryl-C$_{1-6}$ alkyl-, C$_{3-10}$ cycloalkyl-C$_{1-6}$ alkyl-, 5-14 membered heteroaryl-C$_{1-6}$ alkyl-, and 4-14 membered heterocycloalkyl-C$_{1-6}$ alkyl-, wherein the C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5+-14 membered heteroaryl, 4-14 membered heterocycloalkyl, C$_{6-10}$ aryl-C$_{1-6}$ alkyl-, C$_{3-10}$ cycloalkyl-C$_{1-4}$ alkyl-, 5-14 membered heteroaryl-C$_{1-6}$ alkyl- and 4-14 membered heterocycloalkyl-C$_{1-6}$ alkyl- of R$^g$ is each optionally substituted with 1, 2, 3m or 4 independently selected R$^h$ substituents;

each R$^h$ is independently selected from H, D, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-14 membered heterocycloalkyl, C$_{6-10}$ aryl-C$_{1-6}$ alkyl-, C$_{3-10}$ cycloalkyl-C$_{1-6}$ alkyl-, 5-14 membered heteroaryl-C$_{1-6}$ alkyl-, and 4-14 membered heterocycloalkyl-C$_{1-6}$ alkyl-, wherein the C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-14 membered heterocycloalkyl, C$_{6-10}$ aryl-C$_{1-6}$ alkyl-, C$_{3-10}$ cycloalkyl-C$_{1-4}$ alkyl-, 5-14 membered heteroaryl-C$_{1-6}$ alkyl- and 4-14 membered heterocycloalkyl-C$_{1-6}$ alkyl- of R$^h$ is each optionally substituted with 1 or 2 independently selected R$^i$ substituents;

each R$^i$ is independently selected from H, D, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-6}$ alkyl-, C$_{3-10}$ cycloalkyl-C$_{1-6}$ alkyl-, 5-14 membered heteroaryl-C$_{1-6}$ alkyl-, and 4-14 membered heterocycloalkyl-C$_{1-6}$ alkyl-;

each R$^k$ is independently selected from H, CN, OH, C$_{1-4}$ alkyl, and C$_{1-4}$ alkoxy;

each R$^m$ is independently selected from D, OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-10}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, —O-carbamyl, —O—C$_{1-6}$ alkylcarbamyl, —O-di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{4-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and each R$''$ is independently selected from H, D, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, phenyl, C$_{3-6}$ cycloalkyl, 5-6 membered heteroaryl, and 4-6 membered heterocycloalkyl;

or any two R$''$ substituents, together with the atom to which they attached form a 4-, 5-, 6-, or 7-membered heterocycloalkyl group, wherein said heterocycloalkyl group is optionally substituted by 1, 2, 3, or 4 independently selected R$^m$ groups.

In some embodiments:

X$^1$ is N or CR$^1$;

X$^6$ is N or CR$^6$;

Ring A is a 5-14 membered bridged biheterocycloalkyl which is optionally substituted by 1, 2, 3, or 4 independently selected R$^2$ groups;

Y$^1$ is a C$_{6-10}$ aryl, C$_{3-10}$ cycloalkyl, 5-14 membered heteroaryl, or 4-14 membered heterocycloalkyl, wherein the C$_{6-10}$ aryl, C$_{3-10}$ cycloalkyl, 5-14 membered heteroaryl and 4-14 membered heterocycloalkyl of Y$^1$ are each optionally substituted with 1, 2, 3, or 4 independently selected R$^b$ substituents;

R$^1$, R$^5$, R$^6$, and R$^7$ are each independently selected from H, D, halo, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-14 membered heterocycloalkyl, C$_{6-10}$ aryl-C$_{1-6}$ alkyl-, C$_{3-10}$ cycloalkyl-C$_{1-6}$ alkyl-, 5-14 membered heteroaryl-C$_{1-6}$ alkyl-, 4-14 membered heterocycloalkyl-C$_{1-6}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NR$^a$C(O)R$^a$, NR$^a$C(O)OR$^a$, NR$^a$C(O)NR$^a$R$^a$, C(=NR$^k$)R$^a$, C(=NR$^k$)NR$^a$R$^a$, NR$^a$C(=NR$^k$)NR$^a$R$^a$, NR$^a$C(=NOH)NR$^a$R$^a$, NR$^a$C(=NCN)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, S(O)(=NR$^k$)R$^a$, SF$_5$, —P(O)R$^a$R$^a$, —P(O)(OR$^a$)(OR$^a$), B(OR$^a$)$_2$ and S(O)$_2$NR$^a$R$^a$, wherein the C$_{1-6}$ alkyl, C$_{1-6}$ alkoxy, C$_{2-6}$ alkenyl, C$_{2-6}$ alkynyl, C$_{1-6}$ haloalkyl, C$_{1-6}$haloalkoxy, C$_{6-10}$ aryl, C$_{3-10}$ cycloalkyl, 5-14 membered heteroaryl, 4-14 membered heterocycloalkyl, C$_{6-10}$ aryl-C$_{1-6}$ alkyl-, C$_{3-10}$ cycloalkyl-C$_{1-6}$ alkyl-, 5-14 membered heteroaryl-C$_{1-6}$ alkyl-, and 5-14 membered heterocycloalkyl-C$_{1-4}$ alkyl- of R$^1$, R$^5$, R$^6$ and R$^7$ are each optionally substituted with 1, 2, 3, or 4 independently selected R$^b$ substituents;

each R$^2$ is independently selected from D, OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-10}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, —O-carbamyl, —O—C$_{1-6}$ alkylcarbamyl, —O-di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{4-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

R$^8$ is selected from H, D, CN, OH, C$_{1-6}$ alkyl, C$_{1-6}$ alkoxy, C$_{2-6}$ alkenyl, C$_{2-6}$ alkynyl, and C$_{1-6}$ haloalkyl;

R$^9$ is selected from H, D, halo, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-14 membered heteroaryl, 4-14 membered heterocycloalkyl, C$_{6-10}$ aryl-C$_{1-6}$ alkyl-, C$_{3-10}$ cycloalkyl-C$_{1-6}$ alkyl-, 5-14 membered heteroaryl-C$_{1-6}$ alkyl-, 4-14 membered heterocycloalkyl-C$_{1-6}$ alkyl-, CN, NO$_2$, OR$''$, SR$''$, NHOR$''$, C(O)R$''$, C(O)NR$''$R$''$, C(O)OR$''$, OC(O)R$''$, OC(O)NR$''$R$''$, NR$''$R$''$, NR$''$C(O)R$''$, NR$''$C(O)OR$''$, NR$''$C(O)NR$''$R$''$, C(=NR$^k$)R$''$, C(=NR$^k$)NR$''$R$''$, NR$''$C(=NR$^k$)NR$''$R$''$, NR$''$C(=NOH)NR$''$R$''$, NR$''$C(=NCN)NR$''$R$''$, NR$''$S(O)R$''$, NR$''$S(O)$_2$R$''$, NR$''$S(O)$_2$NR$''$R$''$, S(O)R$''$, S(O)NR$''$R$''$, S(O)$_2$R$''$, S(O)(=NR$^k$)R$''$, SF$_5$, —P(O)R$''$R$''$, —P(O)(OR$''$)(OR$''$), B(OR$''$)$_2$ and S(O)$_2$NR$''$R$''$, wherein the C$_{1-6}$ alkyl, C$_{1-6}$ alkoxy, C$_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^9$ are each optionally substituted with 1, 2, 3, or 4 independently selected $R^m$ substituents;

each $R^a$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^k)R^c$, $C(=NR^k)NR^cR^c$, $NR^cC(=NR^k)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2 NR^cR^c$, $S(O)R^c$, $S(O)NR^cR^c$, $S(O)_2R^c$, $S(O)(=NR^k)R^c$, $SF_5$, —$P(O)R^cR^c$, —$P(O)(OR^c)(OR^c)$, $B(OR^c)_2$ and $S(O)_2 NR^cR^c$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^b$ is each optionally substituted with 1, 2, 3, or 4 independently selected $R^d$ substituents;

each $R^c$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^k)R^e$, $C(=NR^k)NR^eR^e$, $NR^eC(=NR^k)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, $S(O)(=NR^k)R^e$, $SF_5$, —$P(O)R^eR^e$, —$P(O)(OR^e)(OR^e)$, $B(OR^e)_2$ and $S(O)_2 NR^eR^e$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^d$ is each optionally substituted with 1, 2, 3, or 4 independently selected $R^f$ substituents;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^e$ is each optionally substituted with 1, 2, 3, or 4 independently selected $R^f$ substituents;

each $R^f$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^g$, $SR^g$, $NHOR^g$, $C(O)R^g$, $C(O)NR^gR^g$, $C(O)OR^g$, $OC(O)R^g$, $OC(O)NR^gR^g$, $NR^gR^g$, $NR^gC(O)R^g$, $NR^gC(O)OR^g$, $NR^gC(O)NR^gR^g$, $C(=NR^k)R^g$, $C(=NR^k)NR^gR^g$, $NR^gC(=NR^k)NR^gR^g$, $NR^gC(=NOH)NR^gR^g$, $NR^gC(=NCN)NR^gR^g$, $NR^gS(O)R^g$, $NR^gS(O)_2R^g$, $NR^gS(O)_2NR^gR^g$, $S(O)R^g$, $S(O)NR^gR^g$, $S(O)_2R^g$, $S(O)(=NR^k)R^g$, $SF_5$, —$P(O)R^gR^g$, —$P(O)(OR^g)(OR^g)$, $B(OR^g)_2$ and $S(O)_2NR^gR^g$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^f$ is each optionally substituted with 1, 2, 3, or 4 independently selected $R^h$ substituents;

each $R^g$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5+-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^g$ is each optionally substituted with 1, 2, 3m or 4 independently selected $R^h$ substituents;

each $R^h$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^h$ is each optionally substituted with 1 or 2 independently selected $R^i$ substituents;

each $R^i$ is independently selected from H, D, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-;

each $R^k$ is independently selected from H, CN, OH, $C_{1-4}$ alkyl, and $C_{1-4}$ alkoxy;

each $R^m$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{4-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two $R^n$ substituents, together with the atom to which they attached form a 4-, 5-, 6-, or 7-membered heterocycloalkyl group, wherein said heterocycloalkyl group is optionally substituted by 1, 2, 3, or 4 independently selected $R^m$ groups.

In some embodiments:

$X^1$ is N or $CR^1$;

$X^6$ is N or $CR^6$;

Ring A is a $C_{5-10}$ bridged bicycloalkyl which is optionally substituted by 1, 2, 3, or 4 independently selected $R^2$ groups;

$Y^1$ is a $C_{6-10}$ aryl, $C_{3-10}$ cycloalkyl, 5-14 membered heteroaryl, or 4-14 membered heterocycloalkyl, wherein the $C_{6-10}$ aryl, $C_{3-10}$ cycloalkyl, 5-14 membered heteroaryl and 4-14 membered heterocycloalkyl of $Y^1$ are each optionally substituted with 1, 2, 3, or 4 independently selected $R^b$ substituents;

$R^1$, $R^5$, $R^6$, and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aC(O)R^a$, $NR^aC(O)OR^a$, $NR^aC(O)NR^aR^a$, $C(=NR^k)R^a$, $C(=NR^k)NR^aR^a$, $NR^aC(=NR^k)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)(=NR^k)R^a$, $SF_5$, —$P(O)R^aR^a$, —$P(O)(OR^a)(OR^a)$, $B(OR^a)_2$ and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 5-14 membered heterocycloalkyl-$C_{1-4}$ alkyl- of $R^1$, $R^5$, $R^6$ and $R^7$ are each optionally substituted with 1, 2, 3, or 4 independently selected $R^b$ substituents;

each $R^2$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{4-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^8$ is selected from H, D, CN, OH, $C_{1-6}$ alkyl, $C_{1-6}$ alkoxy, $C_{2-6}$ alkenyl, $C_{2-6}$ alkynyl, and $C_{1-6}$ haloalkyl;

$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR''$, $SR''$, $NHOR''$, $C(O)R''$, $C(O)NR''R''$, $C(O)OR''$, $OC(O)R''$, $OC(O)NR''R''$, $NR''R''$, $NR''C(O)R''$, $NR''C(O)OR''$, $NR''C(O)NR''R''$, $C(=NR^k)R''$, $C(=NR^k)NR''R''$, $NR''C(=NR^k)NR''R''$, $NR''C(=NOH)NR''R''$, $NR''C(=NCN)NR''R''$, $NR''S(O)R''$, $NR''S(O)_2R''$, $NR''S(O)_2NR''R''$, $S(O)R''$, $S(O)NR''R''$, $S(O)_2R''$, $S(O)(=NR^k)R''$, $SF_5$, —$P(O)R''R''$, —$P(O)(OR'')(OR'')$, $B(OR'')_2$ and $S(O)_2NR''R''$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^9$ are each optionally substituted with 1, 2, 3, or 4 independently selected $R^m$ substituents;

each $R^a$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^k)R^c$, $C(=NR^k)NR^cR^c$, $NR^cC(=NR^k)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2 NR^cR^c$, $S(O)R^c$, $S(O)NR^cR^c$, $S(O)_2R^c$, $S(O)(=NR^k)$ $R^c$, $SF_5$, —$P(O)R^cR^c$, —$P(O)(OR^c)(OR^c)$, $B(OR^c)_2$ and $S(O)_2NR^cR^c$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^b$ is each optionally substituted with 1, 2, 3, or 4 independently selected $R^d$ substituents;

each $R^c$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^k)R^e$, $C(=NR^k)NR^eR^e$, $NR^eC(=NR^k)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, $S(O)(=NR^k)R^e$, $SF_5$, —$P(O)R^eR^e$, —$P(O)(OR^e)(OR^e)$, $B(OR^e)_2$ and $S(O)_2NR^eR^e$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^d$ is each optionally substituted with 1, 2, 3, or 4 independently selected $R^f$ substituents;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^e$ is each optionally substituted with 1, 2, 3, or 4 independently selected $R^f$ substituents;

each $R^f$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^g$, $SR^g$, $NHOR^g$, $C(O)R^g$, $C(O)NR^gR^g$, $C(O)OR^g$, $OC(O)R^g$, $OC(O)NR^gR^g$, $NR^gR^g$, $NR^gC(O)R^g$, $NR^gC(O)OR^g$, $NR^gC(O)NR^gR^g$, $C(=NR^k)R^g$, $C(=NR^k)$ $NR^gR^g$, $NR^gC(=NR^k)NR^gR^g$, $NR^gC(=NOH)NR^gR^g$, $NR^gC(=NCN)NR^gR^g$, $NR^gS(O)R^g$, $NR^gS(O)_2R^g$, $NR^gS(O)_2NR^gR^g$, $S(O)R^g$, $S(O)NR^gR^g$, $S(O)_2R^g$, $S(O)(=NR^k)$ $R^g$, $SF_5$, —$P(O)R^gR^g$, —$P(O)(OR^g)(OR^g)$, $B(OR^g)_2$ and $S(O)_2NR^gR^g$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^f$ is each optionally substituted with 1, 2, 3, or 4 independently selected $R^h$ substituents;

each $R^g$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5+-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^g$ is each optionally substituted with 1, 2, 3m or 4 independently selected $R^h$ substituents;

each $R^h$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^h$ is each optionally substituted with 1 or 2 independently selected $R^i$ substituents;

each $R^i$ is independently selected from H, D, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-;

each $R^k$ is independently selected from H, CN, OH, $C_{1-4}$ alkyl, and $C_{1-4}$ alkoxy;

each $R^m$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, phenyl, $C_{3-6}$ cycloalkyl, 5-6 membered heteroaryl, and 4-6 membered heterocycloalkyl;

or any two R''' substituents, together with the atom to which they attached form a 4-, 5-, 6-, or 7-membered heterocycloalkyl group, wherein said heterocycloalkyl group is optionally substituted by 1, 2, 3, or 4 independently selected R''' groups.

In some embodiments, Ring A is a $C_{5-10}$ bridged bicycloalkyl or a 5-10 membered bridged biheterocycloalkyl.

In some embodiments, Ring A is a 5-10 membered bridged biheterocycloalkyl.

In some embodiments, Ring A is a 8-10 membered bridged biheterocycloalkyl.

In some embodiments, Ring A is a 8 membered bridged biheterocycloalkyl.

In some embodiments, Ring A is a 9 membered bridged biheterocycloalkyl.

In some embodiments, Ring A is a 10 membered bridged biheterocycloalkyl.

In some embodiments, Ring A is a $C_{5-10}$ bridged bicycloalkyl.

In some embodiments, Ring A is selected from bicyclo[1.1.1]pentanylene, bicyclo[2.1.1]hexanylene, bicyclo[2.2.1]heptanylene, bicyclo[2.2.2]octanylene, azabicyclo[2.1.1]hexanylene, azabicyclo[2.2.1]heptanylene, azabicyclo[2.2.2]octanylene, oxabicyclo[2.1.1]hexanylene, oxabicyclo[2.2.1]heptanylene, and oxabicyclo[2.2.2]octanylene, each of which is optionally substituted by 1, 2, or 3 independently selected $R^2$ groups.

In some embodiments, Ring A is selected from bicyclo[1.1.1]pentanylene, bicyclo[2.1.1]hexanylene, bicyclo[2.2.1]heptanylene, bicyclo[2.2.2]octanylene, azabicyclo[2.1.1]hexanylene, azabicyclo[2.2.1]heptanylene, oxabicyclo[2.1.1]hexanylene, and oxabicyclo[2.2.2]octanylene, each of which is optionally substituted by 1, 2, or 3 independently selected $R^2$ groups.

In some embodiments, Ring A is selected from azabicyclo[2.1.1]hexanylene, azabicyclo[2.2.1]heptanylene, azabicyclo[2.2.2]octanylene, oxabicyclo[2.1.1]hexanylene, oxabicyclo[2.2.1]heptanylene, and oxabicyclo[2.2.2]octanylene, each of which is optionally substituted by 1, 2, or 3 independently selected $R^2$ groups.

In some embodiments, Ring A is selected from azabicyclo[2.1.1]hexanylene, azabicyclo[2.2.1]heptanylene, oxabicyclo[2.1.1]hexanylene, and oxabicyclo[2.2.2]octanylene.

In some embodiments, Ring A is selected from

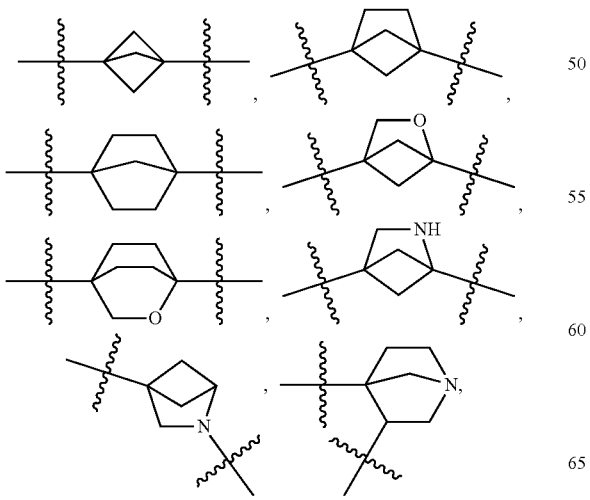

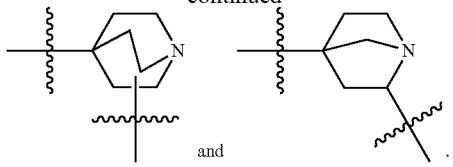

In some embodiments, Ring A is selected from

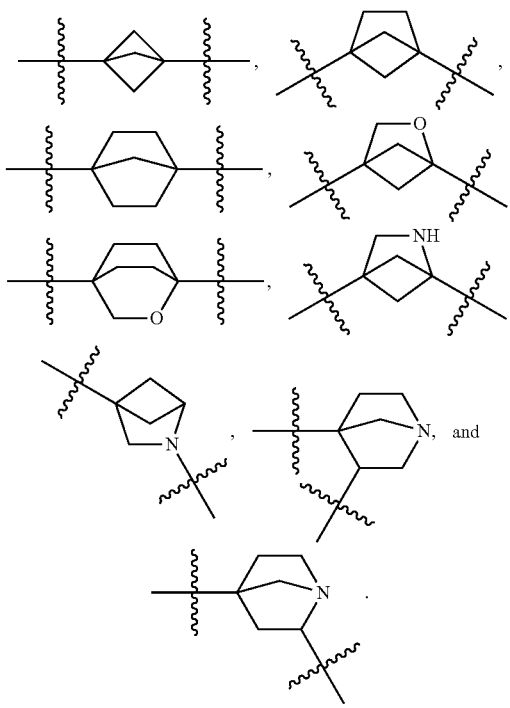

In some embodiments, Ring A is selected from

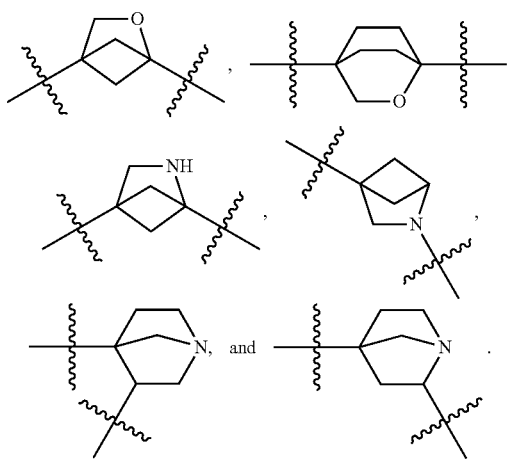

In some embodiments, Ring A is selected from bicyclo[1.1.1]pentanylene, bicyclo[2.1.1]hexanylene, bicyclo[2.2.1]heptanylene, and bicyclo[2.2.2]octanylene, each of which is optionally substituted by 1, 2, or 3 independently selected $R^2$ groups.

In some embodiments, Ring A is selected from

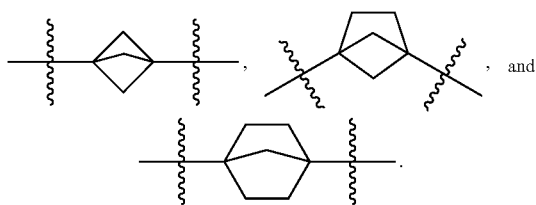

In some embodiments, Ring A is

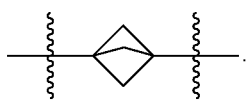 [SMILES: *C12CC(*)(C1)C2]

In some embodiments, Ring A is

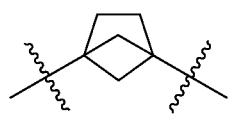

In some embodiments, Ring A is

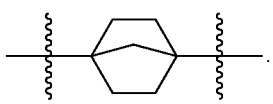 [SMILES: *C12CCC(*)(CC1)C2]

In some embodiments, $X^1$ is N.
In some embodiments, $X^1$ is $CR^1$.
In some embodiments, $X^1$ is CH.
In some embodiments, $X^1$ is N or CH.
In some embodiments, $R^5$ is selected from H, D, and $C_{1-6}$ alkyl.
In some embodiments, $R^5$ is $C_{1-6}$ alkyl or $CD_3$.
In some embodiments, $R^5$ is methyl or —$CD_3$.
In some embodiments, $X^6$ is N.
In some embodiments, $X^6$ is $CR^6$.
In some embodiments, $R^6$ is H or halo.
In some embodiments, $R^6$ is H or fluoro.
In some embodiments, $R^7$ is selected from H, D, and $C_{1-6}$ alkyl.
In some embodiments, $R^7$ is H or D.
In some embodiments, $R^7$ is H.
In some embodiments, $R^8$ is selected from H, D, and $C_{1-6}$ alkyl.
In some embodiments, $R^8$ is H or D.
In some embodiments, $R^8$ is H.
In some embodiments, $R^7$ is selected from H, D, and $C_{1-6}$ alkyl and $R^8$ is H.
In some embodiments, $R^7$ is H or D, and $R^8$ is H.
In some embodiments, $R^7$ and $R^8$ are each H.
In some embodiments, $Y^1$ is phenyl, $C_{3-7}$ cycloalkyl, 5-6 membered heteroaryl, or 4-7 membered heterocycloalkyl, wherein the phenyl, $C_{3-7}$ cycloalkyl, 5-6 membered heteroaryl, or 4-7 membered heterocycloalkyl are each optionally substituted with 1, 2, 3, or 4 independently selected $R^b$ substituents.

In some embodiments, $Y^1$ is phenyl, $C_{3-7}$ cycloalkyl, 5-6 membered heteroaryl, or 4-7 membered heterocycloalkyl, wherein the phenyl, $C_{3-7}$ cycloalkyl, 5-6 membered heteroaryl, or 4-7 membered heterocycloalkyl are each optionally substituted with 1 or 2 independently selected $R^b$ substituents.

In some embodiments, $Y^1$ is a 5-6 membered heteroaryl group which is optionally substituted by 1, 2, 3, or 4 independently selected $R^b$ substituents.

In some embodiments, $Y^1$ is selected from thiazolyl, pyrazolyl, triazolyl, tetrazolyl, oxazolyl, pyridyl, pyrimidinyl, isothiazolyl, pyrrolyl, and pyridazinyl wherein the thiazolyl, pyrazolyl, triazolyl, tetrazolyl, oxazolyl, pyridyl, pyrimidinyl, isothiazolyl, pyrrolyl, and pyridazinyl are each optionally substituted by 1 or 2 independently selected $R^b$ substituents.

In some embodiments, $Y^1$ is selected from thiazolyl, pyrazolyl, triazolyl, tetrazolyl, oxazolyl, pyridyl, and pyrimidinyl, wherein the thiazolyl, pyrazolyl, triazolyl, tetrazolyl, oxazolyl, pyridyl, and pyrimidinyl are each optionally substituted by 1 or 2 independently selected $R^b$ substituents.

In some embodiments, $Y^1$ is selected from thiazolyl, pyrazolyl, triazolyl, oxazolyl, pyridyl, and pyrimidinyl, wherein the thiazolyl, pyrazolyl, triazolyl, oxazolyl, pyridyl, and pyrimidinyl are each optionally substituted by 1 or 2 independently selected $R^b$ substituents.

In some embodiments, the $R^b$ substituents on $Y^1$ are each independently selected from halo, $C_{1-6}$ alkyl, $C_{1-6}$ haloalkyl, $C_{3-10}$ cycloalkyl, CN, $NR^cR^c$, and $SR^c$.

In some embodiments, the $R^b$ substituents on $Y^1$ are each independently selected from $C_{1-6}$ alkyl, $NR^cR^c$, and $SR^c$.

In some embodiments, the $R^b$ substituents on $Y^1$ are each independently selected from fluoro, methyl, $CD_3$, trifluoromethyl, cyclopropyl, CN, dimethylamino, and methylthio.

In some embodiments, the $R^b$ substituents on $Y^1$ are each independently selected from fluoro, methyl, trifluoromethyl, cyclopropyl, CN, dimethylamino, and methylthio.

In some embodiments, the $R^b$ substituents on $Y^1$ are each independently selected from fluoro, methyl, $CD_3$, trifluoromethyl, cyclopropyl, and CN.

In some embodiments, the $R^b$ substituents on $Y^1$ are each independently selected from methyl, dimethylamino, and methylthio.

In some embodiments, $Y^1$ is selected from 2-methylthiazol-5-yl, 2-cyclopropylthiazol-5-yl, oxazol-2-yl, oxazol-5-yl, 2-methyloxazol-5-yl, 1H-pyrazol-1-yl, 1-methyl-1H-pyrazol-3-yl, 1,3-dimethyl-1H-pyrazol-4-yl, 1H-1,2,4-triazol-1-yl, 1H-1,2,3-triazol-1-yl, 2H-1,2,3-triazol-2-yl, 1-methyl-1H-1,2,4-triazol-3-yl, 2H-tetrazol-5-yl, pyridin-3-yl, pyridin-4-yl, 2-methylpyridin-4-yl, 2-cyanopyridin-4-yl, 3-fluoropyridin-4-yl, 2-(trifluoromethyl)pyridin-4-yl, 3-cyanopyridin-4-yl, pyrimidin-2-yl, pyrimidin-4-yl, pyrimidin-5-yl, 2-(methylthio)pyrimidin-4-yl, and 2-(dimethylamino)pyrimidin-5-yl, wherein each can be optionally substituted by 1 or 2 independently selected $R^b$ substituents.

In some embodiments, $Y^1$ is selected from 2-methylthiazol-5-yl, 2-cyclopropylthiazol-5-yl, oxazol-2-yl, oxazol-5-yl, 2-methyloxazol-5-yl, 1H-pyrazol-1-yl, 1-methyl-1H-pyrazol-3-yl, 1,3-dimethyl-1H-pyrazol-4-yl, 1H-1,2,4-triazol-1-yl, 1H-1,2,3-triazol-1-yl, 2H-1,2,3-triazol-2-yl, 1-methyl-1H-1,2,4-triazol-3-yl, 2H-tetrazol-5-yl, pyridin-3-yl, pyridin-4-yl, 2-methylpyridin-4-yl, 2-cyanopyridin-4-yl, 3-fluoropyridin-4-yl, 2-(trifluoromethyl)pyridin-4-yl, 3-cyanopyridin-4-yl, pyrimidin-2-yl, pyrimidin-4-yl, pyrimidin-5-yl, 2-(methylthio)pyrimidin-4-yl, and 2-(dimethylamino)pyrimidin-5-yl.

In some embodiments, $Y^1$ is selected from 1H-pyrazol-1-yl, 1-methyl-1H-pyrazol-3-yl, 1,3-dimethyl-1H-pyrazol-4-yl, 1H-1,2,3-triazol-1-yl, 2H-1,2,3-triazol-2-yl, 1H-1,2,4-triazol-1-yl, 1-methyl-1H-1,2,4-triazol-3-yl, 2H-tetrazol-5-yl, oxazol-2-yl, oxazol-5-yl, 2-methyloxazol-5-yl, 2-methylthiazol-5-yl, pyridin-3-yl, pyridin-4-yl, pyrimidin-2-yl, pyrimidin-4-yl, 2-(methylthio)pyrimidin-4-yl, pyrimidin-5-yl, and 2-(dimethylamino)pyrimidin-5-yl.

In some embodiments, $Y^1$ is selected from 1H-pyrazol-1-yl, 1,3-dimethyl-1H-pyrazol-4-yl, 1H-1,2,4-triazol-1-yl, 2H-1,2,3-triazol-2-yl, 1-methyl-1H-1,2,4-triazol-3-yl, 1H-1,2,3-triazol-1-yl, 1-(methyl-d$_3$)-1H-1,2,4-triazol-3-yl, oxazol-5-yl, 2-methylthiazol-5-yl, 2-cyclopropylthiazol-5-yl, 2-methylpyridin-4-yl, 3-fluoropyridin-4-yl, 2-cyanopyridin-4-yl, 3-cyanopyridin-4-yl, 2-(trifluoromethyl)pyridin-4-yl, and pyrimidin-4-yl.

In some embodiments, $R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OR'', C(O)R'', C(O)NR''R'', C(O)OR'', OC(O)R'', OC(O)NR''R'', NR''R'', NR''C(O)R'', NR''C(O)OR'', and NR''C(O)NR''R'', wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of $R^9$ are each optionally substituted with 1, 2, 3 or 4 independently selected $R'''$ substituents.

In some embodiments, $R^9$ is selected from H, $C_{1-6}$ alkyl, $C_{1-6}$ alkoxy, CN, OR'', C(O)R'', C(O)NR''R'', NR''C(O)R'', and NR''C(O)OR'', wherein the $C_{1-6}$ alkyl and $C_{1-6}$ alkoxy are each optionally substituted with 1 or 2 independently selected $R'''$ substituents.

In some embodiments, $R^9$ is selected from H, $C_{1-6}$ alkyl, $C_{1-6}$ alkoxy, CN, OR'', C(O)R'', C(O)NR''R'', NR''C(O)R'', and NR''C(O)OR'', wherein the $C_{1-6}$ alkyl are each optionally substituted with 1 or 2 $R'''$ groups selected from OH and —O—$C_{1-6}$ alkylcarbamyl, and each R'' is independently selected from H, $C_{1-6}$ alkyl, and $C_{1-6}$ haloalkyl; or two R'' substituents, together with the nitrogen atom to which they attached form a 4-, 5-, 6-, or 7-membered heterocycloalkyl group.

In some embodiments, $R^9$ is selected from H, CN, OH, methyl, 2-isopropyl, hydroxymethyl, 1-hydroxyethyl, 2-hydroxypropan-2-yl, —CH$_2$OC(O)NHCH$_3$, C(O)NHCH$_3$, C(O)N(CH$_3$)$_2$, C(O)-azetidin-1-yl, C(O)NHCH$_2$CF$_3$, NHC(O)OCH$_2$CH$_3$, and NHC(O)CH$_3$.

In some embodiments, $R^9$ is selected from H, CN, OH, hydroxymethyl, 2-hydroxypropan-2-yl, —CH$_2$OC(O)NHCH$_3$, C(O)NHCH$_3$, C(O)N(CH$_3$)$_2$, C(O)-azetidin-1-yl, C(O)NHCH$_2$CF$_3$, NHC(O)OCH$_2$CH$_3$, and NHC(O)CH$_3$.

In some embodiments, $R^9$ is selected from H, methyl, 2-isopropyl, hydroxymethyl, and 1-hydroxyethyl.

In some embodiments:

$X^1$ is N or CH;

$X^6$ is N or CR$^6$;

Ring A is a $C_{5-10}$ bridged bicycloalkyl or a 5-10 membered bridged biheterocycloalkyl each of which is optionally substituted by 1, 2, 3, or 4 independently selected $R^2$ groups;

$R^2$ is selected from D, OH, NO$_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxy carbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^5$ is $C_{1-6}$ alkyl;

$R^6$ is H or halo;

$R^7$ is H;

$R^8$ is H;

$Y^1$ is phenyl, $C_{3-7}$ cycloalkyl, 5-10 membered heteroaryl, or 4-10 membered heterocycloalkyl, wherein the phenyl, C3-7 cycloalkyl, 5-10 membered heteroaryl, or 4-10 membered heterocycloalkyl are each optionally substituted with 1, 2, 3, or 4 independently selected $R^b$ substituents;

$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OR'', C(O)R'', C(O)NR''R'', C(O)OR'', OC(O)R'', OC(O)NR''R'', NR''R'', NR''C(O)R'', NR''C(O)OR'', and NR''C(O)NR''R'', wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of $R^9$ are each optionally substituted with 1, 2, 3 or 4 independently selected $R'''$ substituents;

each $R^b$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, NO$_2$, OR$^c$, SR$^c$, NHOR$^c$, C(O)R$^c$, C(O)NR$^c$R$^c$, C(O)OR$^c$, OC(O)R$^c$, OC(O)NR$^c$R$^c$, NR$^c$R$^c$, NR$^c$C(O)R$^c$, NR$^c$C(O)OR$^c$, NR$^c$C(O)NR$^c$R$^c$, C(=NR$^k$)R$^c$, C(=NR$^k$)NR$^c$R$^c$, NR$^c$C(=NR$^k$)NR$^c$R$^c$, NR$^c$C(=NOH)NR$^c$R$^c$, NR$^c$C(=NCN)NR$^c$R$^c$, NR$^c$S(O)R$^c$, NR$^c$S(O)$_2$R$^c$, NR$^c$S(O)$_2$ NR$^c$R$^c$, S(O)R$^c$, S(O)NR$^c$R$^c$, S(O)$_2$R$^c$, S(O)(=NR$^k$)R$^c$, SF$_5$, —P(O)R$^c$R$^c$, —P(O)(OR$^c$)(OR$^c$), B(OR$^c$)$_2$ and S(O)$_2$ NR$^c$R$^c$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^b$ is each optionally substituted with 1, 2, 3, or 4 independently selected $R^d$ substituents;

each $R^c$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, NO$_2$, OR$^e$, SR$^e$, NHOR$^e$, C(O)R$^e$, C(O)NR$^e$R$^e$, C(O)OR$^e$, OC(O)R$^e$, OC(O)NR$^e$R$^e$, NR$^e$R$^e$, NR$^e$C(O)R$^e$, NR$^e$C(O)OR$^e$, NR$^e$C(O)NR$^e$R$^e$, C(=NR$^k$)R$^e$, C(=NR$^k$)NR$^e$R$^e$, NR$^e$C(=NR$^k$)NR$^e$R$^e$, NR$^e$C(=NOH)NR$^e$R$^e$, NR$^e$C(=NCN)NR$^e$R$^e$, NR$^e$S(O)R$^e$, NR$^e$S(O)$_2$R$^e$, NR$^e$ S(O)₂NRᵉRᵉ, S(O)Rᵉ, S(O)NRᵉRᵉ, S(O)₂Rᵉ, S(O)(=NRᵏ)Rᵉ, SF₅, —P(O)RᵉRᵉ, —P(O)(ORᵉ)(ORᵉ), B(ORᵉ)₂ and S(O)₂NRᵉRᵉ;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-;

each $R^k$ is independently selected from H, CN, OH, $C_{1-4}$ alkyl, and $C_{1-4}$ alkoxy;

each $R^m$ is independently selected from D, OH, NO₂, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{4-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two $R^n$ substituents, together with the atom to which they attached form a 4-, 5-, 6-, or 7-membered heterocycloalkyl group.

In some embodiments:

$X^1$ is N or CH;

$X^6$ is N or $CR^6$;

Ring A is selected from bicyclo[1.1.1]pentanylene, bicyclo[2.1.1]hexanylene, bicyclo[2.2.1]heptanylene, bicyclo[2.2.2]octanylene, azabicyclo[2.1.1]hexanylene, azabicyclo[2.2.1]heptanylene, oxabicyclo[2.1.1]hexanylene, and oxabicyclo[2.2.2]octanylene;

$R^5$ is $C_{1-6}$ alkyl;

$R^6$ is H or halo;

$R^7$ is H;

$R^8$ is H;

$Y^1$ is a 5-6 membered heteroaryl group which is optionally substituted by 1, 2, 3, or 4 independently selected $R^b$ substituents;

$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OR″, C(O)R″, C(O)NR″R″, C(O)OR″, OC(O)R″, OC(O)NR″R″, NR″R″, NR″C(O)R″, NR″C(O)OR″, and NR″C(O)NR″R″, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of $R^9$ are each optionally substituted with 1, 2, 3 or 4 independently selected $R^m$ substituents;

each $R^b$ is independently selected from halo, $C_{1-6}$ alkyl, $C_{1-6}$ haloalkyl, $C_{3-10}$ cycloalkyl, CN, $NR^cR^c$, and $SR^c$;

each $R^c$ is independently selected from H, D, and $C_{1-6}$ alkyl;

each $R^m$ is independently selected from D, OH, NO₂, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{4-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two $R^n$ substituents, together with the atom to which they attached form a 4-, 5-, 6-, or 7-membered heterocycloalkyl group.

In some embodiments:

$X^1$ is N or CH;

$X^6$ is N or $CR^6$;

Ring A is selected from

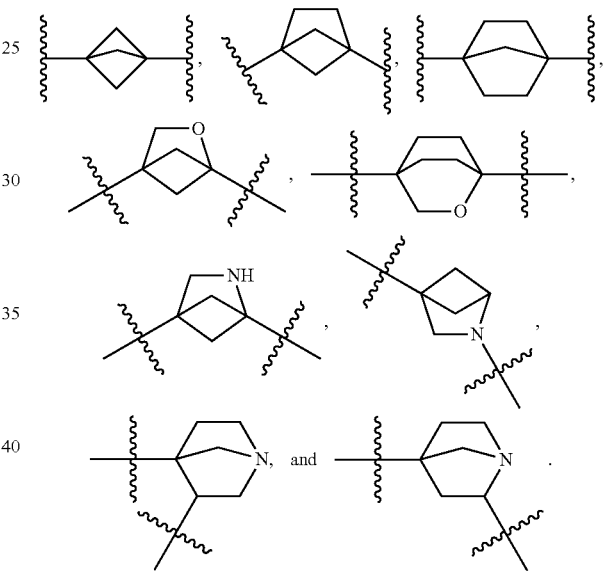

$R^5$ is $C_{1-6}$ alkyl;

$R^6$ is H or halo;

$R^7$ is H;

$R^8$ is H;

$Y^1$ is selected from thiazolyl, pyrazolyl, triazolyl, tetrazolyl, oxazolyl, pyridyl, and pyrimidinyl, wherein the thiazolyl, pyrazolyl, triazolyl, tetrazolyl, oxazolyl, pyridyl, and pyrimidinyl are each optionally substituted by 1 or 2 independently selected $R^b$ substituents;

$R^9$ is selected from H, $C_{1-6}$ alkyl, $C_{1-6}$ alkoxy, CN, OR″, C(O)R″, C(O)NR″R″, NR″C(O)R″, and NR″C(O)OR″, wherein the $C_{1-6}$ alkyl and $C_{1-6}$ alkoxy are each optionally substituted with 1 or 2 $R^m$ substituents;

each $R^b$ is independently selected from halo, $C_{1-6}$ alkyl, $C_{1-6}$ haloalkyl, $C_{3-10}$ cycloalkyl, CN, $NR^cR^c$, and $SR^c$;

each $R^c$ is independently selected from H, D, and $C_{1-6}$ alkyl;

each $R^m$ is independently selected from OH and —O—$C_{1-6}$ alkylcarbamyl; and each $R^n$ is independently selected from H, $C_{1-6}$ alkyl, and $C_{1-6}$ haloalkyl;

or any two R″ substituents, together with the atom to which they attached form a 4-, 5-, 6-, or 7-membered heterocycloalkyl group.

In some embodiments:

$X^1$ is N or CH;

$X^6$ is N or $CR^6$;

Ring A is a 5-10 membered bridged biheterocycloalkyl which is optionally substituted by 1, 2, 3, or 4 independently selected $R^2$ groups;

$R^2$ is selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^5$ is $C_{1-6}$ alkyl;

$R^6$ is H or halo;

$R^7$ is H;

$R^8$ is H;

$Y^1$ is phenyl, $C_{3-7}$ cycloalkyl, 5-10 membered heteroaryl, or 4-10 membered heterocycloalkyl, wherein the phenyl, $C_{3-7}$ cycloalkyl, 5-10 membered heteroaryl, or 4-10 membered heterocycloalkyl are each optionally substituted with 1, 2, 3, or 4 independently selected $R^b$ substituents;

$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OR″, C(O)R″, C(O)NR″R″, C(O)OR″, OC(O)R″, OC(O)NR″R″, NR″R″, NR″C(O)R″, NR″C(O)OR″, and NR″C(O)NR″R″, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of $R^9$ are each optionally substituted with 1, 2, 3 or 4 independently selected $R^m$ substituents;

each $R^b$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^k)R^e$, $C(=NR^k)NR^eR^e$, $NR^eC(=NR^k)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2 NR^eR^e$, $S(O)R^e$, $S(O)NR^eR^e$, $S(O)_2R^e$, $S(O)(=NR^k)R^e$, $SF_5$, —$P(O)R^eR^e$, —$P(O)(OR^e)(OR^e)$, $B(OR^e)_2$ and $S(O)_2 NR^eR^e$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^b$ is each optionally substituted with 1, 2, 3, or 4 independently selected $R^d$ substituents;

each $R^c$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^k)R^e$, $C(=NR^k)NR^eR^e$, $NR^eC(=NR^k)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2 NR^eR^e$, $S(O)R^e$, $S(O)NR^eR^e$, $S(O)_2R^e$, $S(O)(=NR^k)R^e$, $SF_5$, —$P(O)R^eR^e$, —$P(O)(OR^e)(OR^e)$, $B(OR^e)_2$ and $S(O)_2 NR^eR^e$;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-;

each $R^k$ is independently selected from H, CN, OH, $C_{1-4}$ alkyl, and $C_{1-4}$ alkoxy;

each $R^m$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{4-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two R″ substituents, together with the atom to which they attached form a 4-, 5-, 6-, or 7-membered heterocycloalkyl group.

In some embodiments:

$X^1$ is N or CH;

$X^6$ is N or $CR^6$;

Ring A is selected from azabicyclo[2.1.1]hexanylene, azabicyclo[2.2.1]heptanylene, oxabicyclo[2.1.1]hexanylene, and oxabicyclo[2.2.2]octanylene;

$R^5$ is $C_{1-6}$ alkyl;

$R^6$ is H or halo;

$R^7$ is H;

$R^8$ is H;

$Y^1$ is a 5-6 membered heteroaryl group which is optionally substituted by 1, 2, 3, or 4 independently selected $R^b$ substituents;

R⁹ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, CN, OR″, C(O)R″, C(O)NR″R″, C(O)OR″, OC(O)R″, OC(O)NR″R″, NR″R″, NR″C(O)R″, NR″C(O)OR″, and NR″C(O)NR″R″, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of R⁹ are each optionally substituted with 1, 2, 3 or 4 independently selected $R^m$ substituents;

each $R^b$ is independently selected from halo, $C_{1-6}$ alkyl, $C_{1-6}$ haloalkyl, $C_{3-10}$ cycloalkyl, CN, $NR^cR^c$, and $SR^c$;

each $R^c$ is independently selected from H, D, and $C_{1-6}$ alkyl;

each $R^m$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each R″ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two R″ substituents, together with the atom to which they attached form a 4-, 5-, 6-, or 7-membered heterocycloalkyl group.

In some embodiments:
X¹ is N or CH;
X⁶ is N or CR⁶;
Ring A is selected from

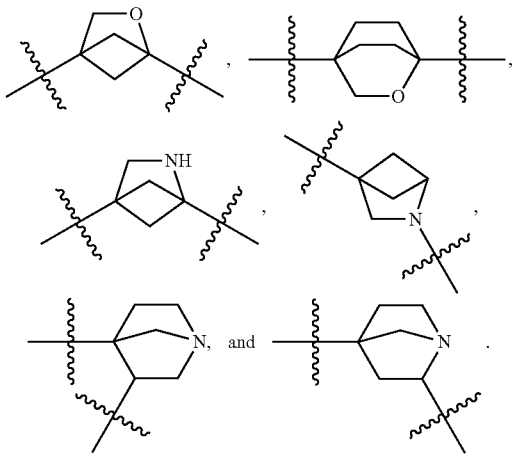

R⁵ is $C_{1-6}$ alkyl;
R⁶ is H or halo;
R⁷ is H;
R⁸ is H;
Y¹ is selected from thiazolyl, pyrazolyl, triazolyl, tetrazolyl, oxazolyl, pyridyl, and pyrimidinyl, wherein the thiazolyl, pyrazolyl, triazolyl, tetrazolyl, oxazolyl, pyridyl, and pyrimidinyl are each optionally substituted by 1 or 2 independently selected $R^b$ substituents;

R⁹ is selected from H, $C_{1-6}$ alkyl, $C_{1-6}$ alkoxy, CN, OR″, C(O)R″, C(O)NR″R″, NR″C(O)R″, and NR″C(O)OR″, wherein the $C_{1-6}$ alkyl and $C_{1-6}$ alkoxy are each optionally substituted with 1 or 2 $R^m$ substituents;

each $R^b$ is independently selected from halo, $C_{1-6}$ alkyl, $C_{1-6}$ haloalkyl, $C_{3-10}$ cycloalkyl, CN, $NR^cR^c$, and $SR^c$;

each $R^c$ is independently selected from H, D, and $C_{1-6}$ alkyl;

each $R^m$ is independently selected from OH and —O—$C_{1-6}$ alkylcarbamyl; and each R″ is independently selected from H, $C_{1-6}$ alkyl, and $C_{1-6}$ haloalkyl;

or any two R″ substituents, together with the atom to which they attached form a 4-, 5-, 6-, or 7-membered heterocycloalkyl group.

In some embodiments:
X¹ is N or CH;
X⁶ is N or CR⁶;
Ring A is a $C_{5-10}$ bridged bicycloalkyl which is optionally substituted by 1, 2, 3, or 4 independently selected R² groups;

R² is selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxy carbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

R⁵ is $C_{1-6}$ alkyl;
R⁶ is H or halo;
R⁷ is H;
R⁸ is H;
Y¹ is phenyl, $C_{3-7}$ cycloalkyl, 5-10 membered heteroaryl, or 4-10 membered heterocycloalkyl, wherein the phenyl, $C_{3-7}$ cycloalkyl, 5-10 membered heteroaryl, or 4-10 membered heterocycloalkyl are each optionally substituted with 1, 2, 3, or 4 independently selected $R^b$ substituents;

R⁹ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, CN, OR″, C(O)R″, C(O)NR″R″, C(O)OR″, OC(O)R″, OC(O)NR″R″, NR″R″, NR″C(O)R″, NR″C(O)OR″, and NR″C(O)NR″R″, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of R⁹ are each optionally substituted with 1, 2, 3 or 4 independently selected $R^m$ substituents;

each $R^b$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^k)R^c$, $C(=NR^k)NR^cR^c$, $NR^cC(=NR^k)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2 NR^cR^c$, $S(O)R^c$, $S(O)NR^cR^c$, $S(O)_2R^c$, $S(O)(=NR^k)R^c$, $SF_5$, —$P(O)R^cR^c$, —$P(O)(OR^c)(OR^c)$, $B(OR^c)_2$ and $S(O)_2 NR^cR^c$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^b$ is each optionally substituted with 1, 2, 3, or 4 independently selected $R^d$ substituents;

each $R^c$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^k)R^e$, $C(=NR^k)NR^eR^e$, $NR^eC(=NR^k)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2 NR^eR^e$, $S(O)R^e$, $S(O)NR^eR^e$, $S(O)_2R^e$, $S(O)(=NR^k)R^e$, $SF_5$, —$P(O)R^eR^e$, —$P(O)(OR^e)(OR^e)$, $B(OR^e)_2$ and $S(O)_2 NR^eR^e$;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-;

each $R^k$ is independently selected from H, CN, OH, $C_{1-4}$ alkyl, and $C_{1-4}$ alkoxy;

each $R^m$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{4-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two $R^n$ substituents, together with the atom to which they attached form a 4-, 5-, 6-, or 7-membered heterocycloalkyl group.

In some embodiments:
$X^1$ is N or CH;
$X^6$ is N or $CR^6$;
Ring A is bicyclo[1.1.1]pentanylene, bicyclo[2.1.1]hexanylene, bicyclo[2.2.1]heptanylene, or bicyclo[2.2.2]octanylene;
$R^5$ is $C_{1-6}$ alkyl;
$R^6$ is H or halo;
$R^7$ is H;
$R^8$ is H;
$Y^1$ is a 5-6 membered heteroaryl group which is optionally substituted by 1, 2, 3, or 4 independently selected $R^b$ substituents;
$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, CN, $OR''$, $C(O)R''$, $C(O)NR''R''$, $C(O)OR''$, $OC(O)R''$, $OC(O)NR''R''$, $NR''R''$, $NR''C(O)R''$, $NR''C(O)OR''$, and $NR''C(O)NR''R''$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of $R^9$ are each optionally substituted with 1, 2, 3 or 4 independently selected $R^m$ substituents;

each $R^b$ is independently selected from halo, $C_{1-6}$ alkyl, $C_{1-6}$ haloalkyl, $C_{3-10}$ cycloalkyl, CN, $NR^cR^c$, and $SR^c$;

each $R^c$ is independently selected from H, D, and $C_{1-6}$ alkyl;

each $R^m$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{4-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two $R^n$ substituents, together with the atom to which they attached form a 4-, 5-, 6-, or 7-membered heterocycloalkyl group.

In some embodiments:
$X^1$ is N or CH;
$X^6$ is N or $CR^6$;
Ring A is

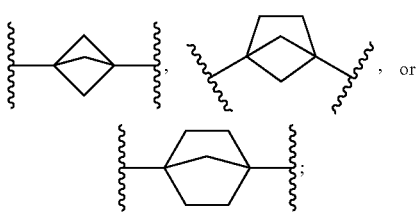

$R^5$ is $C_{1-6}$ alkyl;
$R^6$ is H or halo;
$R^7$ is H;
$R^8$ is H;

$Y^1$ is selected from thiazolyl, pyrazolyl, triazolyl, tetrazolyl, oxazolyl, pyridyl, and pyrimidinyl, wherein the thiazolyl, pyrazolyl, triazolyl, tetrazolyl, oxazolyl, pyridyl, and pyrimidinyl are each optionally substituted by 1 or 2 independently selected $R^b$ substituents;

$R^9$ is selected from H, $C_{1-6}$ alkyl, $C_{1-6}$ alkoxy, CN, $OR''$, $C(O)R''$, $C(O)NR''R''$, $NR''C(O)R''$, and $NR''C(O)OR''$, wherein the $C_{1-6}$ alkyl and $C_{1-6}$ alkoxy are each optionally substituted with 1 or 2 $R^m$ substituents;

each $R^b$ is independently selected from halo, $C_{1-6}$ alkyl, $C_{1-6}$ haloalkyl, $C_{3-10}$ cycloalkyl, CN, $NR^cR^c$, and $SR^c$;

each $R^c$ is independently selected from H, D, and $C_{1-6}$ alkyl;

each $R^m$ is independently selected from OH and —O—$C_{1-6}$ alkylcarbamyl; and each $R''$ is independently selected from H, $C_{1-6}$ alkyl, and $C_{1-6}$ haloalkyl;

or any two $R''$ substituents, together with the atom to which they attached form a 4-, 5-, 6-, or 7-membered heterocycloalkyl group.

In some embodiments, the compound of Formula (I) is a compound of Formula (II):

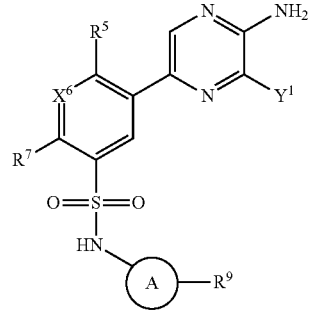

or a pharmaceutically acceptable salt thereof.

In some embodiments, the compound of Formula (I) is a compound of Formula (III):

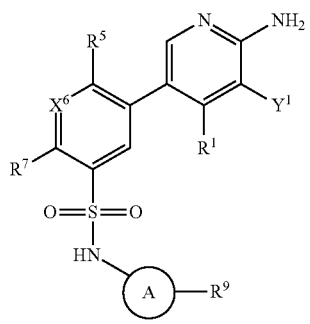

or a pharmaceutically acceptable salt thereof.

In some embodiments, the compound of Formula (I) is a compound of Formula (IV):

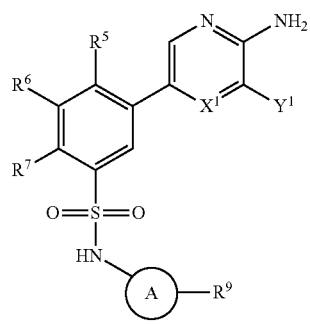

or a pharmaceutically acceptable salt thereof.

In some embodiments, the compound of Formula (I) is a compound of Formula (V):

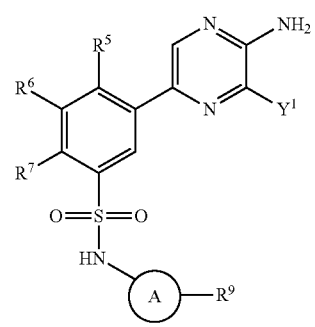

or a pharmaceutically acceptable salt thereof.

In some embodiments, the compound of Formula (I) is a compound of Formula (VI):

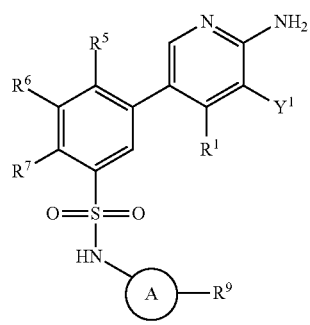

or a pharmaceutically acceptable salt thereof.

In some embodiments, the compound of Formula (I) is a compound of Formula (VII):

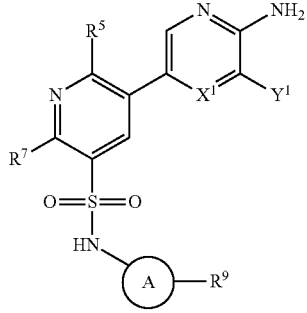

(VII)

or a pharmaceutically acceptable salt thereof.

In some embodiments, the compound of Formula (I) is a compound of Formula (VIII):

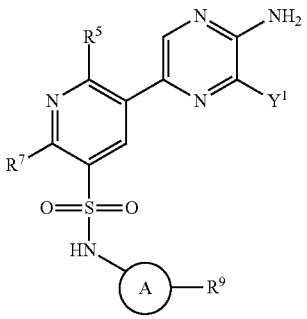

(VIII)

or a pharmaceutically acceptable salt thereof.

In some embodiments, the compound of Formula (I) is a compound of Formula (IX):

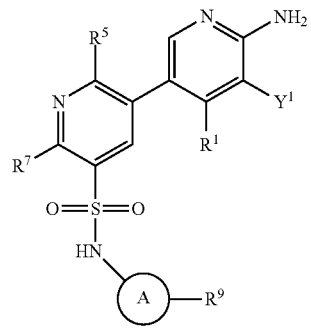

(IX)

or a pharmaceutically acceptable salt thereof.

In some embodiments, the compound of Formula (I) is a compound of Formula (Xa), (Xb), or (Xc):

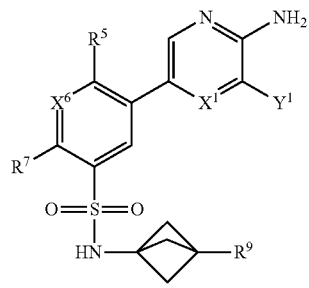

(Xa)

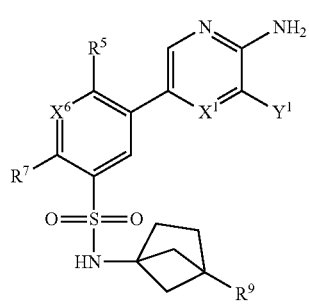

(Xb)

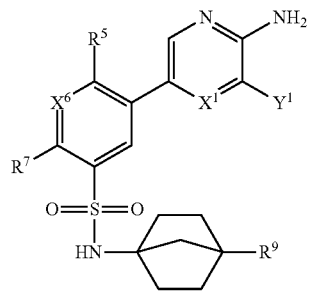

(Xc)

or a pharmaceutically acceptable salt thereof.

In some embodiments, the compound of Formula (I) is a compound of Formula (Xd), (Xe), (Xf), (Xg), (Xh), or (Xi):

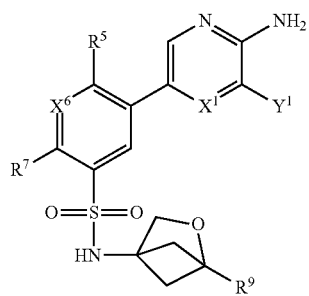

(Xd)

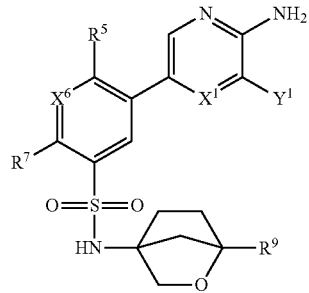

(Xe)

-continued
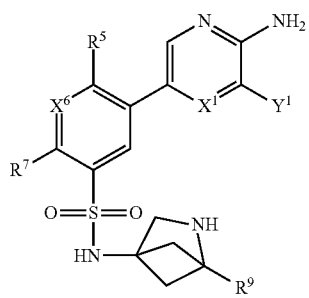
(Xf)
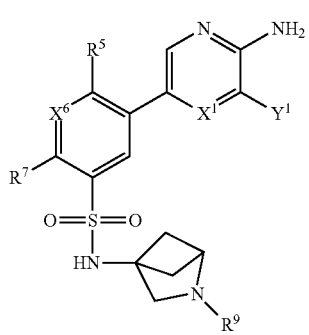
(Xg)
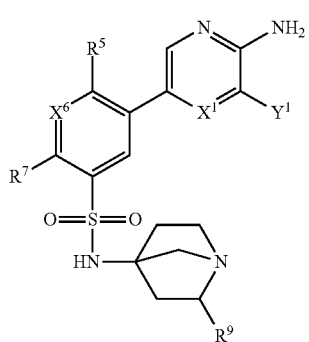
(Xh)
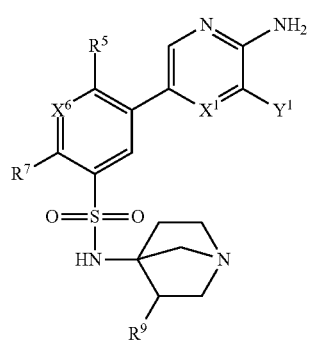
(Xi)
or a pharmaceutically acceptable salt thereof.
In some embodiments, the compound of Formula (I) is a compound of Formula (XIa), (XIb), or (XIc):
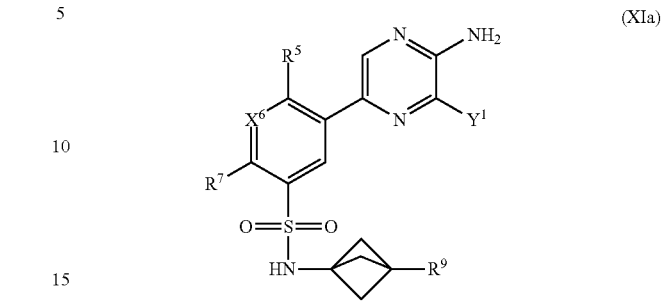
(XIa)
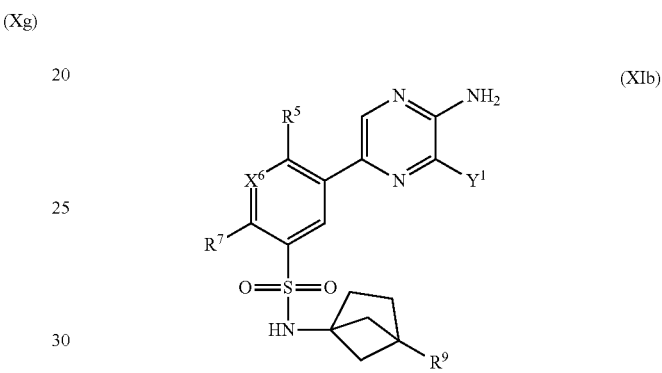
(XIb)
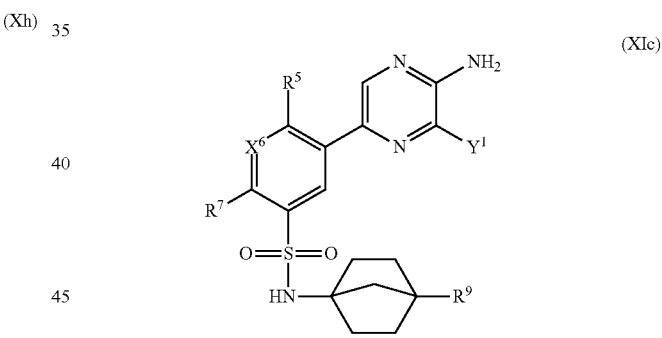
(XIc)
or a pharmaceutically acceptable salt thereof.
In some embodiments, the compound of Formula (I) is a compound of Formula (XId), (XIe), (XIf), (XIg), (XIh), or (XIi):
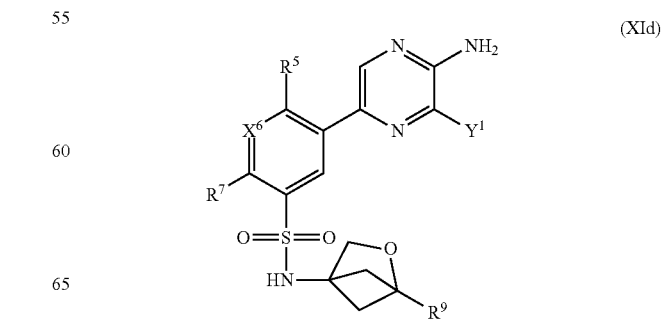
(XId)

-continued
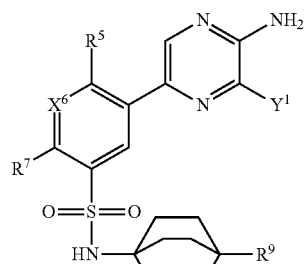
(XIe)
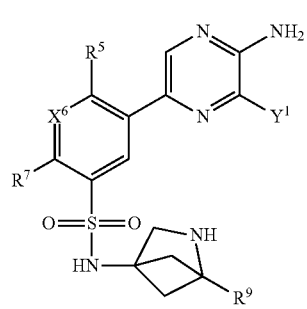
(XIf)
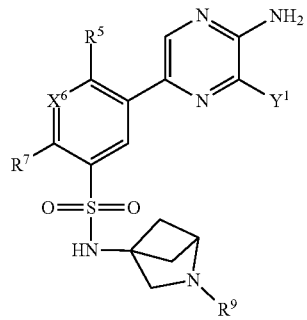
(XIg)
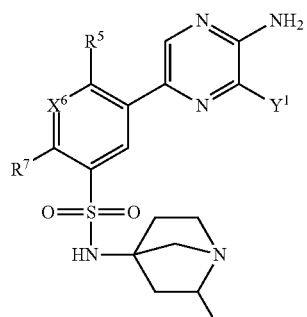
(XIh)
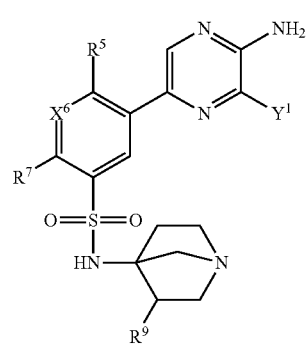
(XIi)
or a pharmaceutically acceptable salt thereof.
In some embodiments, the compound of Formula (I) is a compound of Formula (XIIa), (XIIb), or (XIIc):
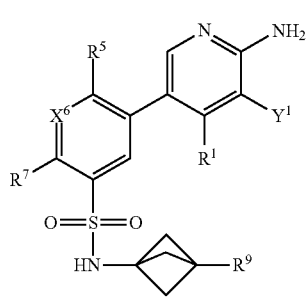
(XIIa)
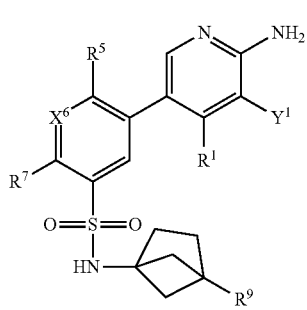
(XIIb)
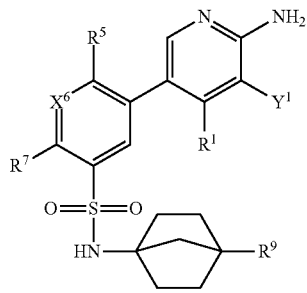
(XIIc)
or a pharmaceutically acceptable salt thereof.
In some embodiments, the compound of Formula (I) is a compound of Formula (XIId), (XIIe), (XIIf), (XIIg), (XIIh), or (XIIi):
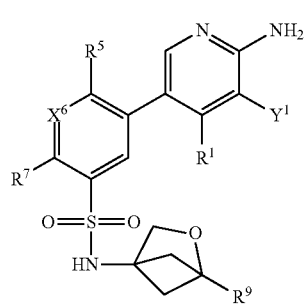
(XIId)

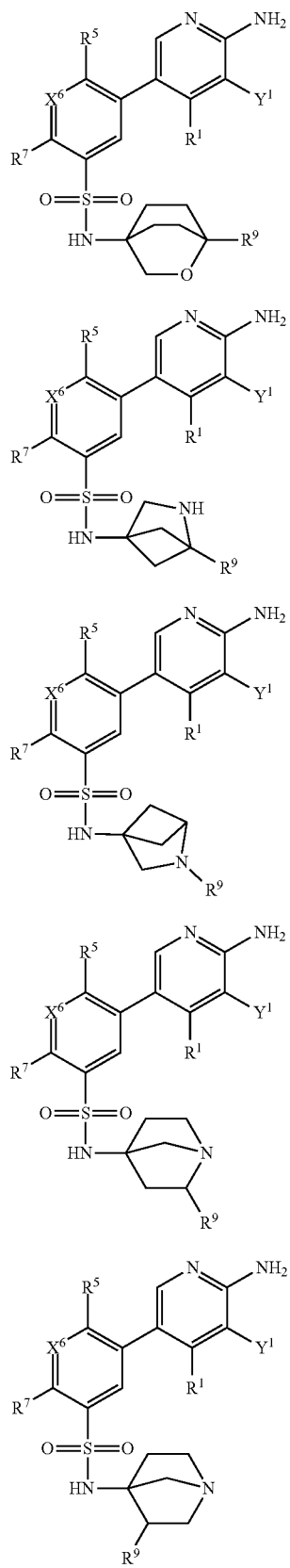
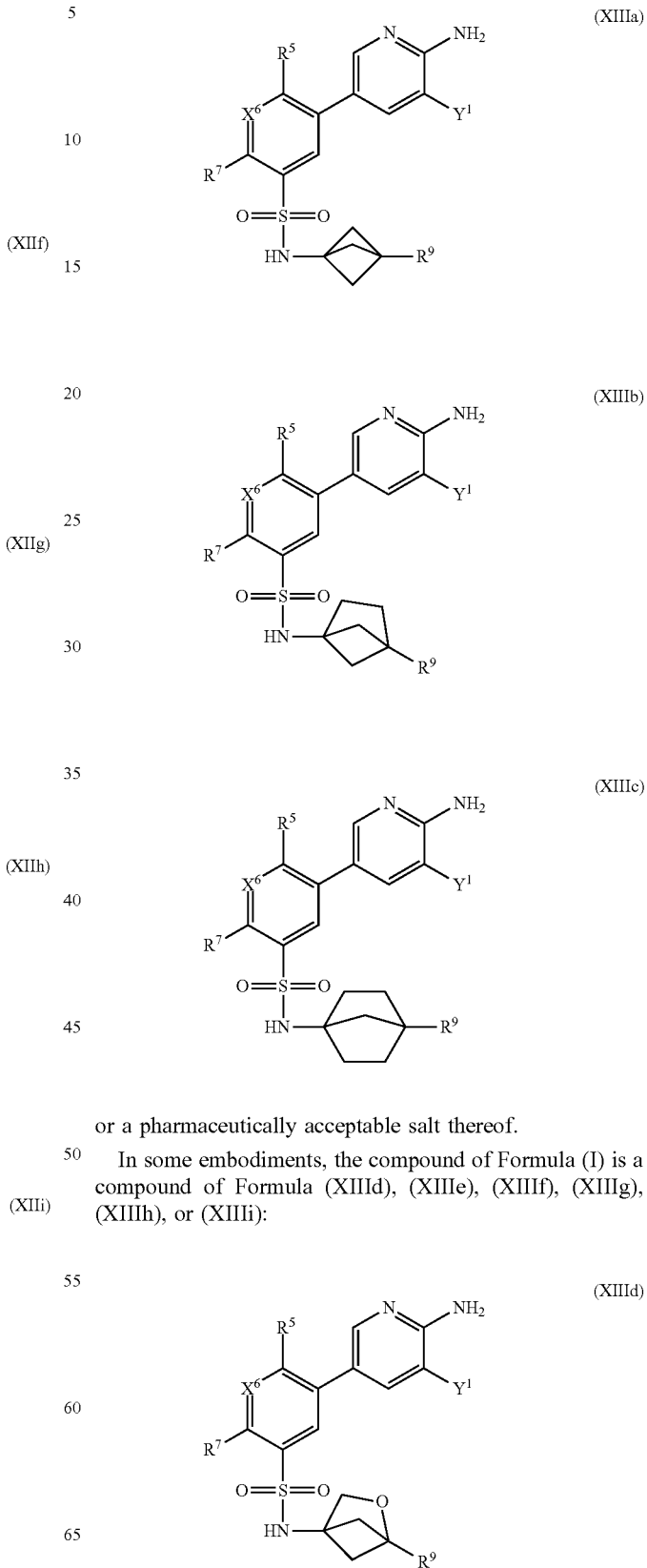
or a pharmaceutically acceptable salt thereof.
In some embodiments, the compound of Formula (I) is a compound of Formula (XIIIa), (XIIIb), or (XIIIc):
or a pharmaceutically acceptable salt thereof.
In some embodiments, the compound of Formula (I) is a compound of Formula (XIIId), (XIIIe), (XIIIf), (XIIIg), (XIIIh), or (XIIIi):

-continued

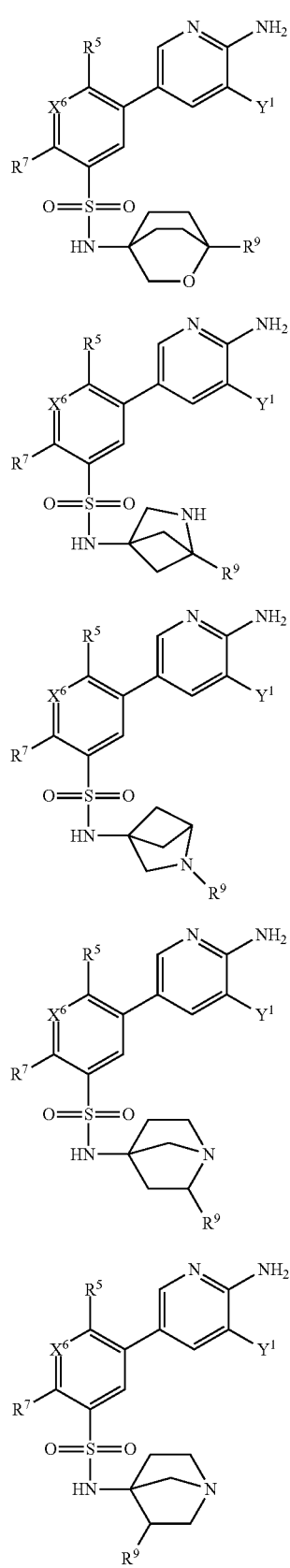

(XIIIe)

(XIIIf)

(XIIIg)

(XIIIh)

(XIIIi)

or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 14 carbon atoms. In some embodiments, the aryl group has from 5 to 10 carbon atoms. In some embodiments, the aryl group is phenyl or naphthyl.

As used herein, "halo" refers to F, Cl, Br, or I. In some embodiments, a halo is F, Cl, or Br. In some embodiments, a halo is F or Cl.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxy carbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbamyl" to a group of formula —C(O)NH$_2$.

As used herein, the term "carbonyl", employed alone or in combination with other terms, refers to a —C(O)— group.

As used herein, the term "cyano-$C_{1-3}$ alkyl" refers to a group of formula —($C_{1-6}$ alkylene)-CN.

As used herein, the term "HO—$C_{1-6}$ alkyl" refers to a group of formula —($C_{1-6}$ alkylene)-OH.

As used herein, the term "$C_{1-6}$ alkoxy-$C_{1-6}$ alkyl" refers to a group of formula —($C_{1-6}$ alkylene)-O($C_{1-3}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13 or 14 ring-forming carbons ($C_{3-14}$). In some embodiments, the cycloalkyl is a $C_{3-14}$ monocyclic or bicyclic cycloalkyl. In some embodiments, the cycloalkyl is a $C_{3-7}$ monocyclic cyclocalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from N, O, S or B. In some embodiments, the heteroaryl ring has 1, 2, 3, or 4 heteroatom ring members independently selected from N, O, S or B. In some embodiments, any ring-forming N in a heteroaryl moiety can be an N-oxide. In some embodiments, the heteroaryl is a 5-14 membered monocyclic or bicyclic heteroaryl having 1, 2, 3 or 4 heteroatom ring members independently selected from N, O, S or B. In some embodiments, the heteroaryl is a 5-6 monocyclic heteroaryl having 1 or 2 heteroatom ring members independently selected from N, O, S or B. In some embodiments, the heteroaryl is a five-membered or six-membereted heteroaryl ring. A five-membered heteroaryl ring is a heteroaryl with a ring having five ring atoms wherein one or more (e.g., 1, 2, or 3) ring atoms are independently selected from N, O, S or B. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine. A six-membered heteroaryl ring is a heteroaryl with a ring having six ring atoms wherein one or more (e.g., 1, 2, or 3) ring atoms are independently selected from N, O, S or B. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from N, O, S or B. Included in heterocycloalkyl are monocyclic 4-14-membered heterocycloalkyl groups. Heterocycloalkyl groups can also include spirocycles and bridged rings (e.g., a 5-14 membered bridged biheterocycloalkyl ring optionally substituted with 0 to 2 additional heteroatoms independently selected from N, O, S or B). Example heterocycloalkyl groups include pyrrolidin-2-one, 1,3-isoxazolidin-2-one, pyranyl, tetrahydropuran, oxetanyl, azetidinyl, morpholine, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from N, O, S or B and having one or more oxidized ring members. In some embodiments, the heterocycloalkyl is a monocyclic or bicyclic 4-10 membered heterocycloalkyl having 1, 2, 3, or 4 heteroatoms independently selected from N, O, S or B and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O), or attached to a nitrogen or sulfur heteroatom forming a nitroso, sulfinyl or sulfonyl group.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention, Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. Formulas (I)-(XIIIi) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluene sulfonic acid, 4-nitrobenzoic acid, methane sulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated, the compounds provided herein, including salts and stereoisomers thereof, can be prepared using known organic synthesis techniques and can be synthesized according to any of numerous possible synthetic routes.

Compounds of Formula I can be prepared via treatment of sulfonyl chlorides 1-1 with amines 1-2 in the presence of base and an appropriate solvent (such as N,N-diisopropylethylamine in DMA or sodium carbonate in DCM/MeCN/$H_2O$) (Scheme 1). Compounds of Formula I can also be prepared by coupling of intermediates 1-3 (wherein X is a substituent capable of undergoing a cross-coupling reaction such as Cl, Br, I, or OTf) with Y-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene] dichloropalladium (II)). Alternatively, displacement of the halogen in 1-3 with nucleophiles Y—H also provides compounds of Formula I.

Scheme 1.

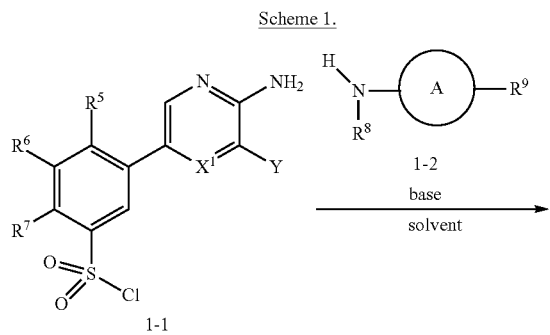

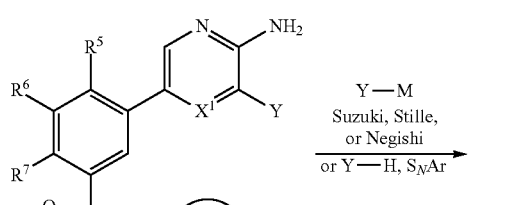

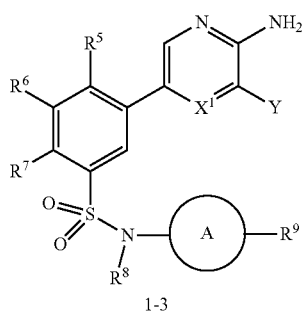

Intermediates 1-1 wherein $X^1$=N can be prepared starting from the commercially available aminopyrazine 2-1 (Scheme 2). Selective cross coupling of the bromide in 2-1 with Y-M provides 2-2. Subsequent cross coupling of the chloride in 2-2 with compounds of the formula 2-3 then provides intermediates 2-4. Chlorosulfonation (e.g., using chlorosulfonic acid in DCM) then affords sulfonyl chlorides 1-1, which can be used for preparing compounds of Formula I, as shown in Scheme 1.

Scheme 2.

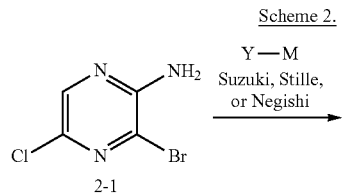

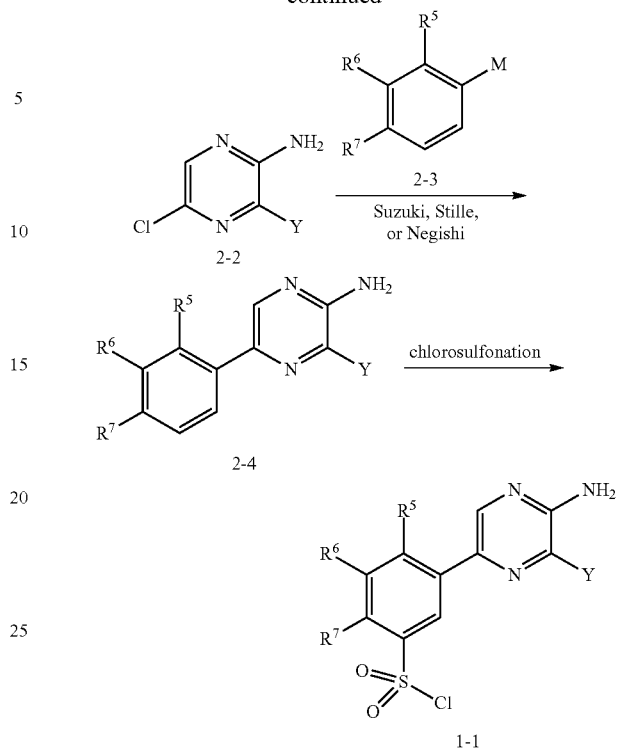

Intermediates 1-1 wherein $X^1$=N can also be prepared starting from the commercially available aminopyrazine 3-1 (Scheme 3). Selective substitution of the chloride with a nucleophile Y—H affords bromide 3-2, which can undergo cross-coupling with 2-3 to furnish intermediates 3-3. Chlorosulfonation of 3-3 then provides sulfonyl chlorides 1-1, which can be used for preparing compounds of Formula I, as shown in Scheme 1.

Scheme 3.

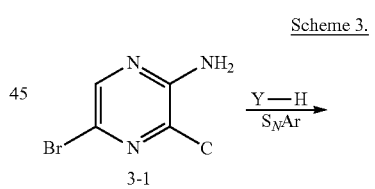

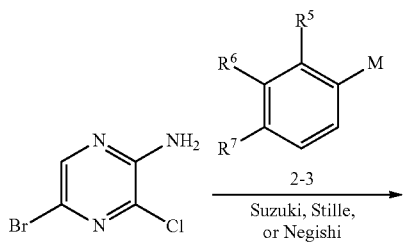

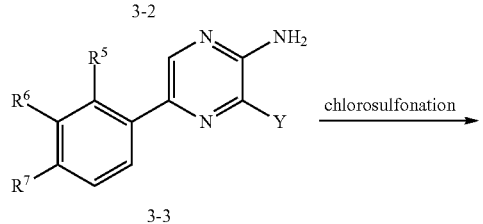

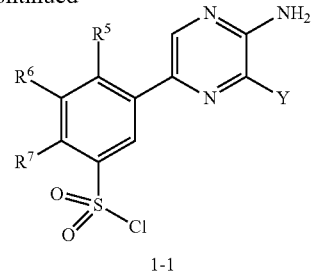

Intermediates 1-3, wherein $X^1$=N and X=Cl can be prepared from the commercially available aminopyrazine 3-1, as shown in Scheme 4. Selective cross-coupling of the bromide with 2-3 affords chloride 4-1. Chlorosulfonation provides sulfonyl chlorides 4-2, which can undergo sulfonamide formation with amines 1-2 to furnish intermediates 1-3, which can be used for preparing compounds of Formula I, as shown in Scheme 1.

Compounds of formula 5-7 (Formula I wherein $X^1$=N and Y is triazolyl) can be synthesized as outlined in Scheme 5. Cross coupling of commercially available pyrazine 5-1 with 2-3 affords nitrile 5-2. Reaction with hydrazine gives the intermediate 5-3, which can be cyclized to form triazoles 5-4 utilizing several methods such as heating with a carboxylic acid (e.g., formic acid, reflux). Alkylation of 5-4 can be achieved by deprotonation with base (e.g., $Cs_2CO_3$), followed by treatment with an electrophile $R^{11}$—X (wherein X is a leaving group) such as an alkyl halide or epoxide. Chlorosulfonation of 5-5 then affords intermediates 5-6, which can react with amines 1-2 under suitable conditions (Scheme 1) to furnish compounds 5-7.

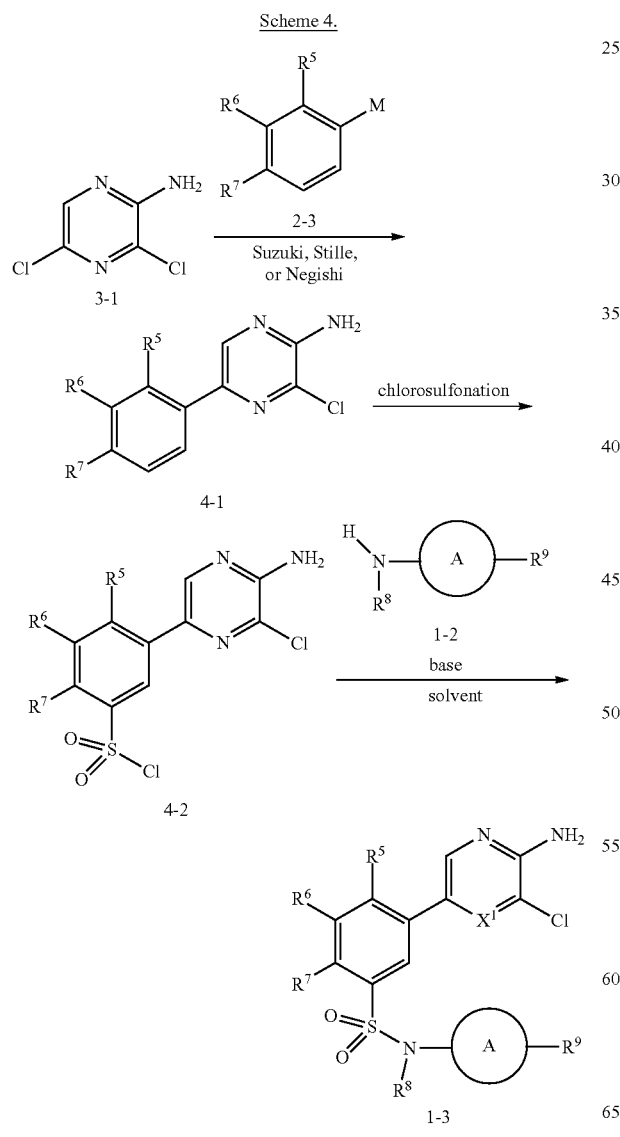

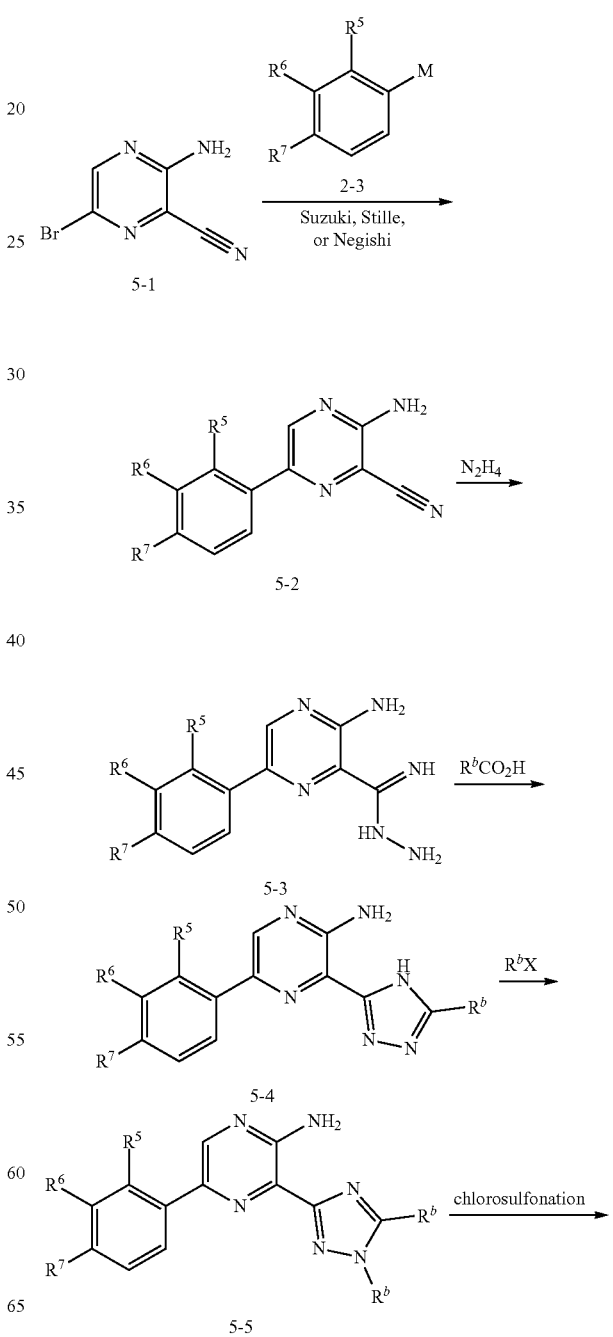

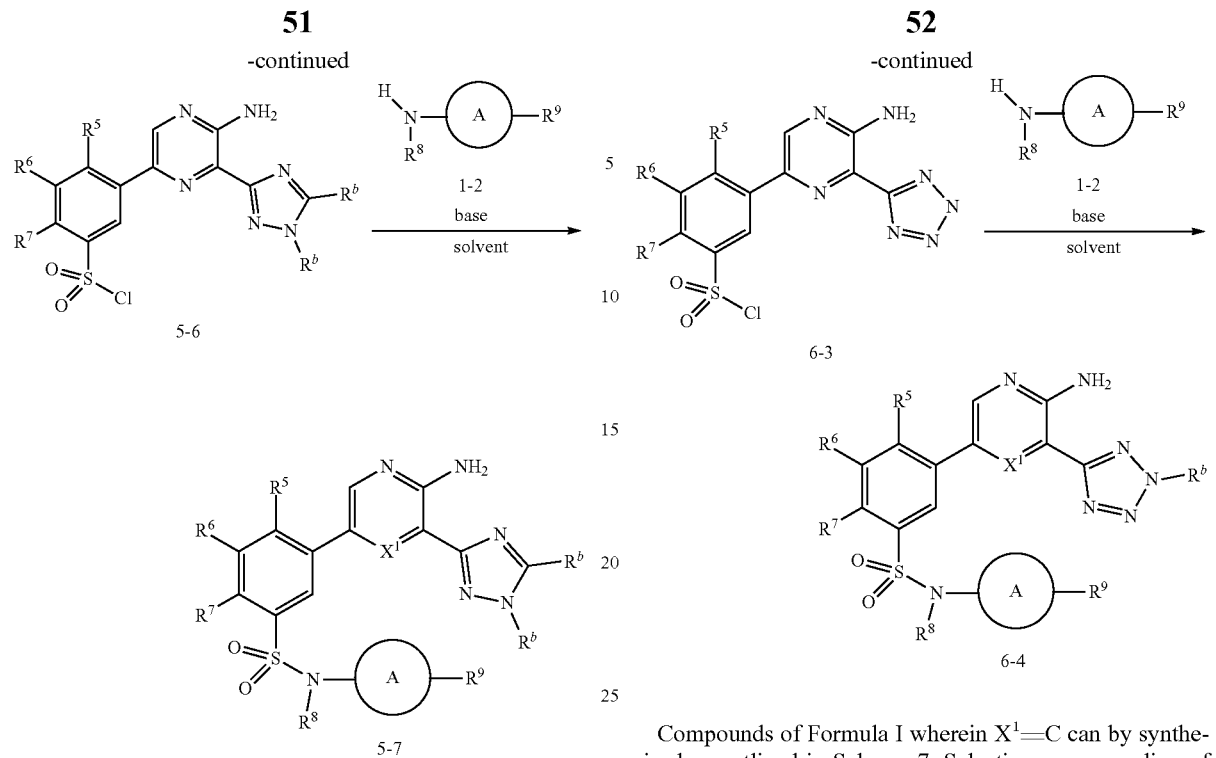

Compounds of formula 6-4 (Formula I wherein X¹=N and Y is tetrazolyl) can be synthesized as outlined in Scheme 6. Reaction of 5-2 with an azide source (e.g., NaN₃) provides tetrazoles 6-1. Alkylation of 6-1 can be achieved by deprotonation with base (e.g., Cs₂CO₃), followed by treatment with an electrophile (such as an alkyl halide or epoxide). Chlorosulfonation of 6-2 then affords intermediates 6-3, which can react with amines 1-2 under suitable conditions (Scheme 1) to furnish compounds of the formula 6-4.

Compounds of Formula I wherein X¹=C can by synthesized as outlined in Scheme 7. Selective cross-coupling of the bromide or iodide with Y-M in the commercially available pyridines 7-1 or 7-2 affords intermediates 7-3. Subsequent cross-coupling of the chloride in 7-3 with 2-3 affords the polycyclic compounds 7-4. Chlorosulfonation (e.g., chlorosulfonic acid in DCM) then furnishes the sulfonyl chlorides 7-5, which upon reaction with amines 1-2 utilizing an appropriate base and solvent (e.g., Na₂CO₃ in DCM/MeCN/H₂O) then provides compounds of Formula I wherein X¹=C.

Scheme 6.

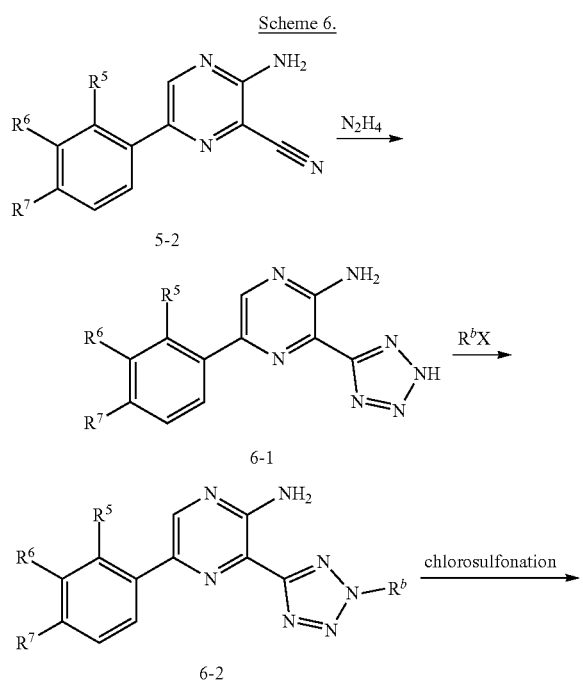

Scheme 7.

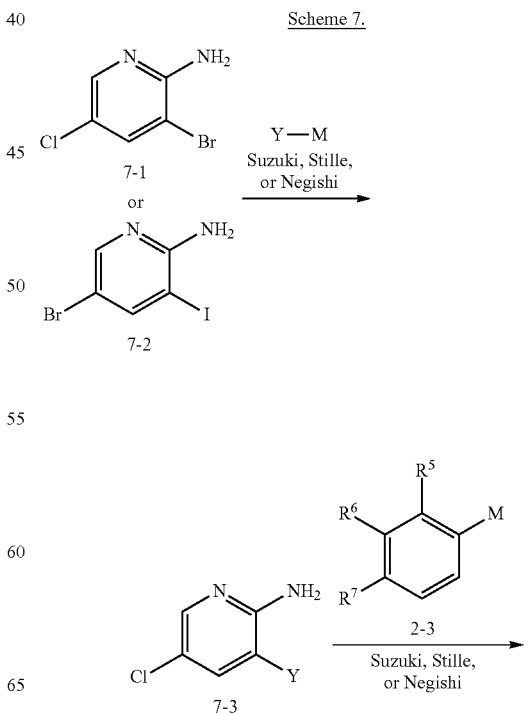

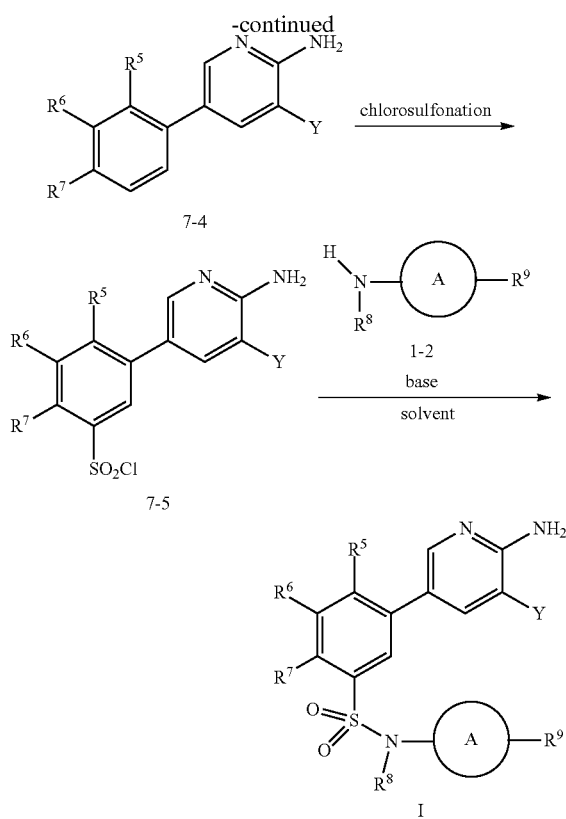

matography (TEC). Compounds can be purified by those skilled in the art by a variety of methods, including high performance liquid chromatography (HPLC) and normal phase silica chromatography.

Methods of Use

The compounds, salts or stereoisomers thereof described herein inhibit activity of PI3Kγ kinase. Accordingly, the compounds, salts or stereoisomers described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual/patient in need of the inhibition by administering an effective amount of a compound or salt of described herein. In some embodiments, modulating is inhibiting. In some embodiments, the contacting is in vivo. In some embodiments, the contacting is ex vivo. Advantageously, the compounds as described herein demonstrate better efficacy and favorable safety and toxicity profiles in animal studies.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds of the disclosure are selective inhibitors of PI3Kγ over PI3Kδ, PI3Kα, and PI3Kβ. In some embodiments, the compounds of the disclosure are selective inhibitors of PI3Kγ over PI3Kα and PI3Kβ. In some embodiments, selectivity can be at least about 2-fold, 3-fold, 5-fold, 10-fold, at or 20-fold over PI3Kδ as measured by the assays described herein. In some embodiments, selectivity can be tested at the 2 μM ATP concentration of each enzyme. In some embodiments, the selectivity of compounds of the disclosure can be determined by cellular assays associated with particular PI3K kinase activity.

Another aspect of the present disclosure pertains to methods of treating a kinase PI3Kγ-associated disease or disorder in an individual (e.g., patient) by administering to the individual in need of such treatment a therapeutically effective amount or dose of one or more compounds of the present disclosure or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chon- The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^{1}$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chrodrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is acute myeloid leukemia (e.g., acute monocytic leukemia), small lymphocytic lymphoma, chronic lymphocytic leukemia (CEL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xenoderoma pigmentosum, keratoctanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the non-Hodgkin's lymphoma (NHL) is relapsed NHL, refractory NHL, recucurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma.

In some embodiments, the Burkitt's lymphoma is endemic Burkitt's lymphoma, sporadic Burkitt's lymphoma, or Burkitt's-like lymphoma.

In some embodiments, the disease or disorder is rheumatoid arthritis, multiple sclerosis, systemic lupus erythematous, asthma, allergy (e.g, allergic rhinitis), pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, the disease or disorder is heart hypertropy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), idiopathic pulmonary fibrosis, autoimmune hemolytic anemia, vasculitis, lupus nephritis, pemphigus, or membranous nephropathy.

In some embodiments, disease or disorder is heart hypertropy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or anti-neutrophil cytoplasm antibody associated (ANCA) systemic vasculitis (AASV).

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the disclosure includes the administration of a compound of the present disclosure to an individual or patient, such as a human, having a PI3K, as well as, for example, introducing a compound of the disclosure into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein. Examples of cancers include solid tumors and liquid tumors, such as blood cancers.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF and FAK kinase inhibitors such as, for example, those described in WO 2006/056399. Other agents such as therapeutic antibodies can be used in combination with the compounds of the present disclosure for treatment of PI3K-associated diseases, disorders or conditions. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABE, ALK and B-Raf. Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSFIR inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGER, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumortargeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfdgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEF), and bendamustine. In some embodiments, the proteasome inhibitor is carfdzomib. In some embodiments, the corticosteroid is dexamethasone (DEX). In some embodiments, the immunomodulatory agent is lenalidomide (FEN) or pomalidomide (POM). Additive or synergistic effects are desirable outcomes of combining a PI3K inhibitor of the present disclosure with an additional agent.

In some embodiments, PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTFA, CTFA-4, FAG3, TIM3, VISTA, PD-1, PD-F1 and PD-F2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTFA, CTFA-4, IDO, KIR, FAG3, PD-1, TIM3, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD 1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD 1 antibody is pembrolizumab. In some embodiments, the anti-PD 1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO 1, TDO, or arginase. Examples of IDO 1 inhibitors include epacadostat and NGL919.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, comovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasibensis, Coccidioides immitis* and *Histoplasma capsulatum*. Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma* gondi, and *Nippostrongylus brasibensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g, by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Substitution of one or more of the atoms of the compounds of the present disclosure can also be useful in generating differentiated ADME (Adsorption, Distribution, Metabolism and Extretion.) Accordingly, the present disclosure includes PI3K assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$).

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1, 2, 3, 4, 5, 6, 7, 8, 9, 10, 11, 12, 13, 14, 15, 16, 17, 18, 19, 20, 21, 22, 23 or 24 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances, (see e.g., A. Kerekes et. al. *J Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of PI3K-associated diseases or disorders, such as cancer, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 30×100 mm or Waters XBridge™ $C_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 μm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Intermediate 1. 1-(4-amino-2-oxabicyclo[2.1.1]hexan-1-yl)ethanol

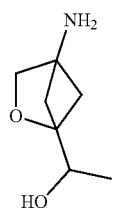

Step 1. Benzyl 1-formyl-2-oxabicyclo[2.1.1]hexan-4-ylcarbamate

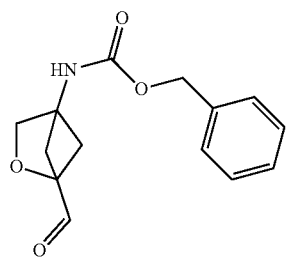 [SMILES: O=CC12CC(NC(=O)OCc3ccccc3)(CO1)C2]

To a solution of benzyl 1-(hydroxymethyl)-2-oxabicyclo[2.1.1]hexan-4-ylcarbamate (25 mg, 0.095 mmol, Intermediate 2) in DCM (3.0 ml) was added sodium bicarbonate (15.9 mg, 0.19 mmol) and Dess-Martin periodinane (81 mg, 0.19 mmol). The reaction mixture was stirred at room temperature until TLC indicated complete consumption of starting material (1 h). The reaction mixture was diluted with DCM, quenched with saturated $Na_2S_2O_3$ and saturated $NaHCO_3$ (1 mL each), and vigorously stirred until two clear layers were obtained (10 min). The layers were separated and the organic layer was dried over $MgSO_4$, filtered, and concentrated. The residue was used without purification.

Step 2. Benzyl 1-(1-hydroxyethyl)-2-oxabicyclo[2.1.1]hexan-4-ylcarbamate

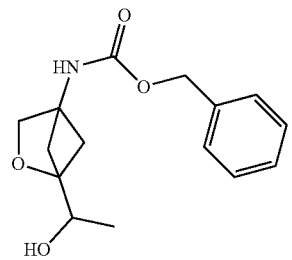 [SMILES: CC(O)C12CC(NC(=O)OCc3ccccc3)(CO1)C2]

To a solution of benzyl (1-formyl-2-oxabicyclo[2.1.1]hexan-4-yl)carbamate (25 mg, 0.09 mmol) in THF (2.0 ml) at 0° C. was added methylmagnesium bromide (96 μl, 0.29 mmol), and the reaction mixture was allowed to warm to room temperature, at which time the reaction was complete as indicated/judged by TLC. The reaction was quenched with water and extracted with EtOAc. The organic layer was washed with brine, dried over $MgSO_4$, filtered, and concentrated. The residue was used without purification.

Step 3. 1-(4-Amino-2-oxabicyclo[2.1.1]hexan-1-yl)ethanol

To a solution of benzyl 1-(1-hydroxyethyl)-2-oxabicyclo[2.1.1]hexan-4-ylcarbamate (25 mg, 0.09 mmol) in MeOH (3 mL) was added a small spatula tip of $Pd(OH)_2$. The vessel was sealed and a hydrogen balloon was attached. The atmosphere was replaced with hydrogen and the reaction mixture was vigorously stirred for 30 min. The reaction mixture was filtered through a pad of Celite®, which was rinsed with MeOH. The volatiles were removed in vacuo and the residue was used without purification. LCMS calculated for $C_7H_{14}NO_2$ $(M+H)^+$: m/z=144.1, found: 144.1.

Intermediate 2. Benzyl 1-(hydroxymethyl)-2-oxabicyclo[2.1.1]hexan-4-ylcarbamate

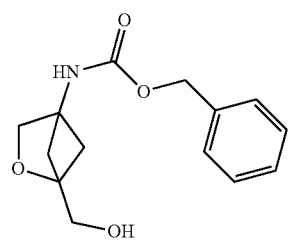 [SMILES: O=C(NC12COC(CO)(C1)C2)OCc1ccccc1]

Step 1. (4-(Hydroxymethyl)-2-oxabicyclo[2.1.1]hexan-1-yl)methyl Acetate

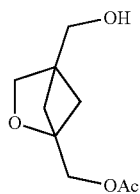 [SMILES: CC(=O)OCC12CC(CO)(CO1)C2]

To a solution of (1-(iodomethyl)-2-oxabicyclo[2.1.1]hexan-4-yl)methanol (874 mg, 3.4 mmol, Intermediate 11, Step 2) in DMF (6.0 mL) was added cesium acetate (990 mg, 5.2 mmol), and the reaction mixture was heated to 100° C. for 2 h. The reaction mixture was partitioned between water and EtOAc and the layers were separated. The organic layer was washed with brine, dried over MgSO$_4$, filtered and concentrated. The residue was purified by flash chromatography (0-100% EtOAc/hexanes, followed by 15% MeOH/DCM) to afford the title compound (326 mg, 51%). $^1$H NMR (400 MHz, CDCl$_3$) δ 4.34 (s, 2H), 3.90 (s, 2H), 3.75 (s, 2H), 2.10 (s, 3H), 1.74 (dd, J=4.6, 1.3 Hz, 2H), 1.64 (dd, J=4.6, 1.5 Hz, 2H). LCMS calculated for C$_9$H$_{15}$O$_4$ (M+H)$^+$: m/z=187.1; found: 187.0.

Step 2. 1-(Acetoxymethyl)-2-oxabicyclo[2.1.1]hexane-4-carboxylic Acid

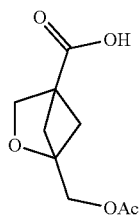 [SMILES: CC(=O)OCC12CC(C(=O)O)(CO1)C2]

A solution of (4-(hydroxymethyl)-2-oxabicyclo[2.1.1]hexan-1-yl)methyl acetate (329 mg, 1.8 mmol) in CH$_2$Cl$_2$ (3 mL)/acetonitrile (3.00 mL)/water (3.00 mL) at 0° C. was stirred rapidly while sodium periodate (1.13 g, 5.30 mmol) and ruthenium(III) chloride hydrate (40 mg, 0.18 mmol) were added. The ice bath was removed, and the solution was stirred at room temperature for 4 h. The reaction was diluted with EtOAc and stirred while 1M HCl was added until all solids dissolved. The layers were separated and the aqueous layer was extracted with EtOAc. The combined extracts were washed with 10% NaHSO$_3$ solution, brine, dried over MgSO$_4$, filtered, and concentrated. The residue was purified by flash chromatography (0-20% MeOH/DCM) to afford the title compound as a white solid (340 mg, 96%). LCMS calculated for C$_9$H$_{13}$O$_5$ (M+H)$^+$: m/z=201.1; found: 201.1.

Step 3. (4-(Benzyloxycarbonylamino)-2-oxabicyclo[2.1.1]hexan-1-yl)methyl Acetate

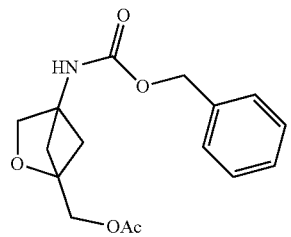 [SMILES: CC(=O)OCC12CC(NC(=O)OCc3ccccc3)(CO1)C2]

To a solution of 1-(acetoxymethyl)-2-oxabicyclo[2.1.1]hexane-4-carboxylic acid (350 mg, 1.75 mmol) in toluene (5.0 mL) was added triethylamine (0.49 mL, 3.50 mmol), followed by diphenylphosphoryl azide (0.56 mL, 2.62 mmol). The reaction mixture was stirred at room temperature for 1 h, then heated to reflux for 2 h. The reaction mixture was then cooled to room temperature and benzyl alcohol (0.36 mL, 3.50 mmol) was added. The resulting solution was heated to reflux overnight. After cooling to room temperature, the reaction mixture was concentrated in vacuo and purified by flash chromatography (0-50% EtOAc/hexanes) to afford the desired product as a colorless oil (391 mg, 73%). LCMS calculated for C$_{16}$H$_{20}$NO$_5$ (M+H)$^+$: m/z=306.1; found: 306.1.

Step 4. Benzyl 1-(hydroxymethyl)-2-oxabicyclo[2.1.1]hexan-4-ylcarbamate

To a solution of (4-(((benzyloxy)carbonyl)amino)-2-oxabicyclo[2.1.1]hexan-1-yl)methyl acetate (391 mg, 1.28 mmol) in MeOH (6.0 mL) was added potassium carbonate (230 mg, 1.67 mmol) at 0° C. The reaction mixture was warmed to room temperature and stirred for 30 min. The reaction mixture was partitioned between water and EtOAc, and the layers were separated. The aqueous layer was extracted with EtOAc and the combined organic layers were washed with brine, dried over MgSO$_4$, filtered, and concentrated. The resulting white solid was used without purification (316 mg, 94%). LCMS calculated for C$_{14}$H$_{18}$NO$_4$ (M+H)$^+$: m/z=264.1; found: 264.2.

Intermediate 3. 3-Aminobicyclo[1.1.1]pentane-1-carbonitrile, Hydrochloric Acid Salt

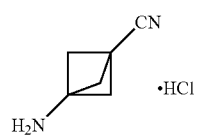

Step 1. 3-((tert-Butoxycarbonyl)amino)bicyclo[1.1.1]pentane-1-carboxylic Acid

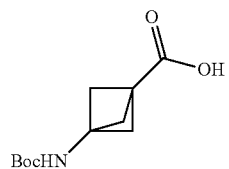 [SMILES: CC(C)(C)OC(=O)NC12CC(C(=O)O)(C1)C2]

A mixture of 3-aminobicyclo[1.1.1]pentane-1-carboxylic acid, HCl (500.0 mg, 3.06 mmol, PharmaBlock) and N,N-diisopropylethylamine (1.0 mL, 6.1 mmol) in THF (10 mL) and water (10 mL) was treated with di-tert-butyl dicarbonate (667 mg, 3.06 mmol). After stirring overnight, the reaction was treated with 1 N HCl to achieve pH 2 and was extracted with EtOAc. The combined organic extracts were washed with water, brine, dried over $Na_2SO_4$, filtered and concentrated to afford a white solid (665 mg, 96%). LCMS for $C_{11}H_{17}NO_4Na$ $(M+Na)^+$: calculated m/z=250.1; found 250.1.

Step 2. tert-Butyl 3-carbamoylbicyclo[1.1.1]pentan-1-ylcarbamate

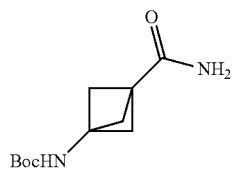 [SMILES: CC(C)(C)OC(=O)NC12CC(C(N)=O)(C1)C2]

A solution of 3-((tert-butoxycarbonyl)amino)bicyclo[1.1.1]pentane-1-carboxylic acid (660 mg, 2.90 mmol) in THF (15 mL) was treated with triethylamine (0.49 mL, 3.5 mmol). The resulting mixture was cooled to −15° C. and ethyl chloroformate (0.31 mL, 3.2 mmol) was added and the mixture was stirred for 1 h. To the mixture was added ammonium hydroxide (19.5 mL, 145 mmol) solution. After stirring for 3 hours, THF was evaporated and to the white crude solid was added water. The aqueous suspension was extracted with EtOAc (3×). The combined organic extracts (fine suspension) were dried over $Na_2SO_4$, and decanted (rather than filtered). The liquid decanted was concentrated to afford a white solid (0.65 g, 100%). LCMS for $C_{11}H_{18}N_2O_3Na$ $(M+Na)^+$: calculated m/z=249.1, found 249.2. $^1H$ NMR (400 MHz, DMSO-$d_6$) δ 7.50 (br s, 1H), 7.21 (s, 1H), 6.91 (s, 1H), 2.02 (s, 6H), 1.38 (s, 9H).

Step 3. tert-Butyl 3-cyanobicyclo[7.7.7]pentan-1-ylcarbamate

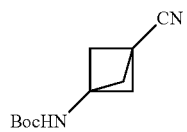 [SMILES: CC(C)(C)OC(=O)NC12CC(C#N)(C1)C2]

tert-Butyl (3-carbamoylbicyclo[1.1.1]pentan-1-yl)carbamate (200.0 mg, 0.884 mmol) in DCM and triethylamine (0.370 mL, 2.65 mmol) at 0° C. was treated with trichloroacetyl chloride (0.15 mL, 1.3 mmol). After 30 minutes, additional triethylamine (0.37 mL, 3.0 eq) and trichloroacetyl chloride (0.15 mL, 1.5 eq) were added. After 30 minutes, the reaction was quenched by the addition of sat'd. $NaHCO_3$ solution and the aqueous mixture was extracted with EtOAc. The combined organic extracts were dried over $Na_2SO_4$, filtered and concentrated. The residue was purified by flash chromatography, eluting with a gradient from 0-100% EtOAc in hexanes and ELSD was used to detect the product which was isolated as a white solid (107 mg, 58%). $^1H$ NMR (400 MHz, CDCl$_3$) δ 5.08 (s, 1H), 2.49 (s, 6H), 1.46 (s, 9H).

Step 4. 3-Aminobicyclo[1.1.1]pentane-1-carbonitrile Hydrochloric Acid Salt tert-Butyl (3-cyanobicyclo[1.1.1]pentan-1-yl)carbamate (0.050 g, 0.24 mmol) was stirred for 2 hours in 4 M HCl in dioxane (3.0 mL, 12.0 mmol). Volatiles were removed in vacuo to afford product (32 mg, 92%). $^1H$ NMR (400 MHz, $CD_3OD$) δ 2.61 (s, 6H).

Intermediate 4. 4-Aminobicyclo[2.1.1]hexane-1-carbonitrile Hydrochloric Acid Salt

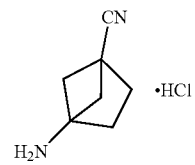

Step 1. 3-((tert-butoxycarbonyl)amino)bicyclo[1.1.1]pentane-1-carboxylic Acid

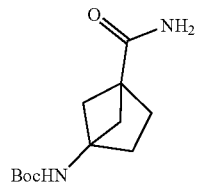 [SMILES: CC(C)(C)OC(=O)NC12CCC(C(N)=O)(C1)C2]

A solution of 4-((tert-butoxycarbonyl)amino)bicyclo[2.1.1]hexane-1-carboxylic acid (250 mg, 1.04 mmol) (Spirochem catalog #SPC-a643) and triethylamine (0.17 mL, 1.2 mmol) in THF (5 mL) at −15° C. was treated with ethyl chloroformate (0.109 mL, 1.14 mmol) and the reaction was stirred for 1 hour. To the mixture was added ammonium hydroxide (14.8 M, 7.0 mL, 52 mmol) in one portion. The reaction mixture was stirred at room temperature overnight. THF was evaporated, and to the white crude solid was added water. The aqueous suspension was extracted with EtOAc (3×). The combined organic extracts were dried over $Na_2SO_4$, filtered and concentrated to afford product as a white solid (219 mg, 88%). LCMS for $C_{12}H_{21}N_2O_3$ $(M+H)^+$: calculated m/z=241.2, found 241.3. $^1H$ NMR (400

MHz, DMSO-$d_6$) δ 7.30 (br s, 1H), 7.07 (s, 1H), 6.83 (s, 1H), 1.93 (br, 2H), 1.70 (s, 4H), 1.49 (s, 2H), 1.38 (s, 9H).

Step 2. tert-Butyl (4-cyanobicyclo[2.1.1]hexan-1-yl)carbamate

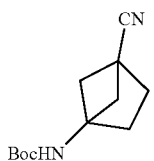

tert-Butyl (4-carbamoylbicyclo[2.1.1]hexan-1-yl)carbamate (290 mg, 1.21 mmol) in DCM (20 mL) containing triethylamine (1.35 mL, 9.65 mmol) at 0° C. was treated with trichloroacetyl chloride (0.54 mL, 4.8 mmol). After 40 minutes, the reaction was quenched with saturated NaHCO$_3$ at 0° C. and the aqueous mixture was extracted with DCM. The organic extract was dried over MgSO$_4$, filtered and concentrated, and the residue was purified by flash chromatography (eluting with a gradient from 0-20% EtOAc/hexanes) to afford product as a white solid (230 mg, 86%). LCMS for $C_{12}H_{19}N_2O_2$ (M+H)$^+$: calculated m/z=223.1, found 223.1. $^1$H NMR (400 MHz, CD$_3$OD) δ 2.35 (br, 2H), 2.06-1.98 (m, 2H), 1.90-1.82 (m, 2H), 1.82-1.78 (m, 2H), 1.45 (s, 9H).

Step 3. 4-Aminobicyclo[2.1.1]hexane-1-carbonitrile, Hydrochloric Acid Salt tert-Butyl (4-cyanobicyclo[2.1.1]hexan-1-yl)carbamate (0.99 g, 4.45 mmol, prepared as in Step 2) was dissolved in DCM (50 mL) and 4 N HCl in dioxane (11.1 mL, 44 mmol) was added. The mixture was stirred overnight and volatiles were removed in vacuo to afford product as a white solid (0.7 g, 100%). LCMS for $C_7H_{11}N_2$ (M+H)$^+$: calculated m/z=123.1, found 123.2. $^1$H NMR (500 MHz, DMSO-$d_6$) δ 9.03 (s, 3H), 2.26-2.20 (m, 2H), 2.11-2.06 (m, 2H), 1.89-1.82 (m, 4H).

Intermediate 5. (3-aminobicyclo[1.1.1]pentan-1-yl)methanol

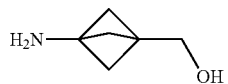

Step 1. 3-(((Benzyloxy)carbonyl)amino)bicyclo[1.1.1]pentane-1-carboxylic Acid

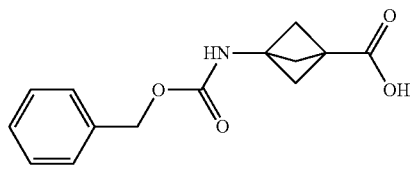 [SMILES: O=C(NC12CC(C(=O)O)(C1)C2)OCc1ccccc1]

A mixture of 3-aminobicyclo[1.1.1]pentane-1-carboxylic acid, HCl (100. mg, 0.611 mmol, PharmaBlock) and NaOH (49 mg, 1.22 mmol) in THF (2 mL) and water (2 mL) at 0° C. was treated with benzyl chloroformate (0.096 mL, 0.672 mmol). The reaction was allowed to warm to room temperature and stir overnight. The reaction mixture was acidified with 4N HCl to achieve pH 4. Additional water was added, and the mixture was extracted with EtOAc. The combined organic extracts were washed with brine, dried over MgSO$_4$, filtered and concentrated. The product was purified by flash chromatography, eluting with a gradient from 0-100% EtOAc in hexanes to afford a colorless oil (60.0 mg, 38%). LCMS calculated for $C_{14}H_{15}NNaO_4$ (M+Na)$^+$: 284.1, found 283.9.

Step 2. Benzyl (3-(hydroxymethyl)bicyclo[1.1.1]pentan-1-yl)carbamate

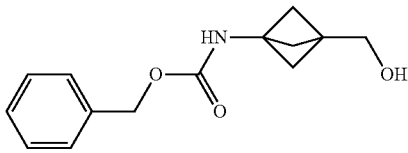 [SMILES: O=C(NC12CC(CO)(C1)C2)OCc1ccccc1]

Ethyl chloroformate (0.024 mL, 0.25 mmol) was added dropwise to a solution of 3-(((benzyloxy)carbonyl)amino)bicyclo[1.1.1]pentane-1-carboxylic acid (60.0 mg, 0.230 mmol) and triethylamine (0.035 mL, 0.25 mmol) in THF (2 mL) at −5° C. The reaction was stirred for 30 minutes at this temperature. The solid formed was removed from the mixture by filtration, and the solid was washed with 2 mL THF. The pooled washings and filtrate were cooled to 0° C. and treated with sodium borohydride (26.1 mg, 0.689 mmol), which was added in one portion, followed by the dropwise addition of MeOH (1 mL). After stirring for 30 minutes at 0° C., the reaction mixture was quenched by the addition of water, followed by 2N HCl. The mixture was transferred to a separatory funnel and the layers were separated. The aqueous layer was extracted several times with EtOAc. The combined organic extracts were dried over MgSO$_4$, filtered and concentrated. The product was used without further purification. Crude yield: 30.0 mg, 52%. LCMS calculated for $C_{14}H_{17}NNaO_3$ (M+Na)$^+$: 270.1, found 270.2.

Step 3. (3-Aminobicyclo[1.1.1]pentan-1-yl)methanol

A degassed solution of benzyl (3-(hydroxymethyl)bicyclo[1.1.1]pentan-1-yl)carbamate (30.0 mg, 0.121 mmol) in MeOH (2 mL) was treated with palladium on carbon (10 wt %, 6.5 mg, 0.0061 mmol) and stirred under 1 atm of H$_2$ for 2 hours. The reaction was filtered, and solvent was removed from the filtrate in vacuo to afford product, which was used without further purification. Theoretical yield was assumed.

Intermediate 6. (4-Amino-2-oxabicyclo[2.1.1]hexan-1-yl)methanol

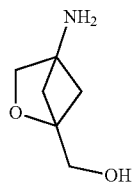

To a solution of Intermediate 2 (40 mg, 0.152 mmol) in MeOH (3 mL) was added palladium hydroxide on carbon (20 wt %, 10.7 mg, 0.02 mmol). The atmosphere was replaced with hydrogen and the reaction mixture was vigorously stirred under 1 atm of hydrogen for 1 h. The reaction mixture was filtered through a pad of Celite®, concentrated in vacuo, and the residue was used without purification. LCMS calculated for $C_6H_{12}NO_2$ $(M+H)^+$: m/z=130.1; found: 130.1.

Intermediate 7. (4-Aminobicyclo[2.1.1]hexan-1-yl)methanol Trifluoroacetate Salt

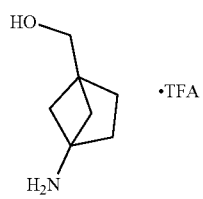

Ethyl chloroformate (0.131 mL, 1.37 mmol) was added dropwise to a solution of 4-((tert-butoxycarbonyl)amino)bicyclo[2.1.1]hexane-1-carboxylic acid (0.300 g, 1.24 mmol, Enamine catalog #EN300-70833) and triethylamine (0.26 mL, 1.9 mmol) in THF (5 mL) at −5° C. The reaction was stirred for 30 minutes at this temperature. The solid formed was filtered and washed with 2 mL THF. The pooled washings and filtrate were cooled to 0° C. and treated with sodium borohydride (141 mg, 3.73 mmol) in one portion followed by MeOH (2 mL), added dropwise. After 30 minutes, the reaction mixture was quenched by the addition of water and 2N HCl. The layers were separated, and the aqueous layer was extracted several times with EtOAc. The combined organic extracts were dried over MgSO₄, filtered and concentrated. LCMS for $C_8H_{14}NO_3$ $(M-^tBu+H)^+$: calculated m/z=172.1, found 172.1. The product, tert-butyl (4-(hydroxymethyl)bicyclo[2.1.1]hexan-1-yl)carbamate (0.28 g, 1.23 mmol) was dissolved in DCM (1 mL), and trifluoroacetic acid (0.96 mL, 12 mmol) was added. The reaction was stirred for 2 hours and solvent was removed in vacuo to obtain the title compound (0.15 g, 95%). LCMS for $C_7H_{14}NO$ $(M+H)^+$: calculated m/z=128.1, found 128.1.

Intermediate 8. (4-Amino-2-oxabicyclo[2.2.2]octan-1-yl)methanol Trifluoroacetate Salt

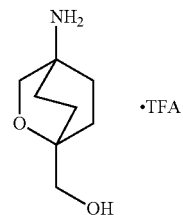

To a solution of tert-butyl 1-formyl-2-oxabicyclo[2.2.2]octan-4-ylcarbamate (30 mg, 0.12 mmol, Advanced Chemblocks) in EtOH (1.0 mL) at 0° C. was added sodium borohydride (22 mg, 0.59 mmol). The reaction mixture was warmed to room temperature and stirred for 0.5 h. The reaction mixture was diluted with EtOAc and water, and the layers were separated. The organic layer was washed with brine, dried over MgSO₄, filtered, and concentrated. The residue was dissolved in DCM (2.0 mL) and treated with TFA (0.5 mL, 6.49 mmol). After stirring for 0.5 h, the volatiles were removed in vacuo, the residue was dissolved in 1:1 MeCN/H₂O, and lyophilized. The product was used without purification. LCMS calculated for $C_8H_{16}NO_2$ $(M+H)^+$: m/z=158.1; found: 158.2.

Intermediate 9. 4-Aminobicyclo[2.2.1]heptan-1-ol Hydrochloride Salt

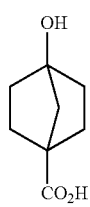

Step 1. 4-Hydroxybicyclo[2.2.1]heptan-1-carboxylic Acid

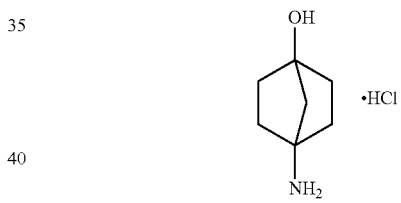

To a solution of methyl 4-hydroxybicyclo[2.2.1]heptane-1-carboxylate (487 mg, 2.86 mmol, Advanced Chemblocks, L13452) in MeOH (5 mL) was added sodium hydroxide (572 mg, 14.3 mmol) in water (5.0 mL) and the reaction mixture was stirred at room temperature. After 1 h, the reaction mixture was acidified with 1 M HCl to pH 1 and extracted with three portions of EtOAc. The organic extracts were washed with brine, dried over MgSO₄, filtered and concentrated to afford a tan solid (257 mg, 58%) that was used without purification.

Step 2. 4-aminobicyclo[2.2.1]heptan-1-ol Hydrochloride Salt

To a solution of 4-hydroxybicyclo[2.2.1]heptane-1-carboxylic acid (257 mg, 1.65 mmol) and triethylamine (0.28 mL, 1.98 mmol) in toluene (6.0 mL) was added diphenylphosphoryl azide (0.43 mL, 1.98 mmol) and the reaction mixture was heated to reflux for 2 h. The reaction mixture was diluted with EtOAc, washed with water and brine, dried over MgSO$_4$ and concentrated. The residue was taken up in a 1:1 mixture of AcOH and 15% HCl (1 mL each) and stirred at room temperature for 1 h. The reaction mixture was washed with EtOAc and the aqueous layer was concentrated to dryness to afford the title compound, which was used without purification.

Intermediate 10. 3-Bromo-5-fluoro-4-methylbenzenesulfonyl Chloride

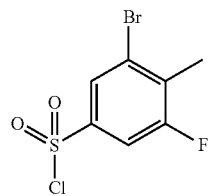

A round-bottom flask was charged with water (80 mL) and placed in an ice bath. To this was added thionyl chloride (13.2 mL, 180 mmol) over 35 min using an addition funnel. The reaction mixture was warmed to room temperature with the aid of a room temperature water bath, treated with copper(I) chloride (0.194 g, 1.96 mmol), and placed in a brine-ice bath. Concurrently in a separate round-bottom flask, 3-bromo-5-fluoro-4-methylaniline (8.00 g, 39.2 mmol, Oxchem, AX8258142) was added dropwise to concentrated hydrochloric acid (98 mL) (the aniline was melted using a 50° C. oil bath before addition) which gave a free-flowing but thick slurry. The reaction mixture was placed in a brine-ice bath and the slurry became thicker but stirring was maintained with a very large stir bar. The reaction mixture was treated with a solution of sodium nitrite (2.98 g, 43.1 mmol) in water (5.58 mL) over 5 mins at −3 to 0° C. which led to dissolution of most of the solids and a much thinner orange slurry. After stirring for 5 mins, the reaction mixture was added to the chilled thionyl chloride solution dropwise in portions by pipette over 15 mins with gas evolution observed and temperature ranging between −7 to −6° C. The reaction mixture was stirred for 2.5 h, warmed to room temperature and stirred for 1 hr. The reaction mixture was diluted with water (250 mL) and extracted with ethyl acetate (3×200 mL). The combined organic extracts were washed with brine (100 mL), dried with magnesium sulfate, filtered, and concentrated to give the desired product (9.79 g, 87%) as an amber oil that was used without further purification.

Intermediate 11. 1-Methyl-2-oxabicyclo[2.1.1]hexan-4-amine Hydrochloride

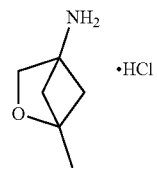

Step 1. (3-Methylenecyclobutane-1,1-diyl)dimethanol

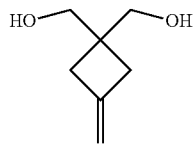

To a suspension of methyltriphenylphosphonium bromide (970 mg, 2.72 mmol) in THF (8 mL) at 0° C. was added potassium tert-butoxide (1.0 M/THF) (2.72 mL, 2.72 mmol). The ice bath was removed and the reaction mixture was stirred at room temperature for 1 h. The resulting yellow solution was cooled to 0° C. and a solution of diisopropyl 3-oxocyclobutane-1,1-dicarboxylate (506 mg, 2.09 mmol, Synthonix) in THF (4 mL) was added dropwise via cannula. The ice bath was removed and the reaction mixture was stirred at room temperature for 1.5 h. The reaction was quenched with saturated NH$_4$Cl and extracted with EtOAc. The organic extracts were washed with brine, dried over MgSO$_4$, filtered, and concentrated. The residue was purified by flash chromatography (0-50% EtOAc/hexanes). The product was not dried under high vacuum due to volatility.

To a solution of diisopropyl 3-methylenecyclobutane-1,1-dicarboxylate (502 mg, 2.09 mmol) in THF (6 mL) at 0° C. was added a solution of lithium aluminum hydride (2.0 M/THF, 3.13 mL, 6.27 mmol) dropwise. The reaction mixture was warmed to room temperature and stirred for 0.5 h. The reaction mixture was diluted with ether and cooled to 0° C. The reaction was quenched by the careful addition of 0.24 mL H$_2$O, followed by 0.24 mL 15% NaOH, and finally 0.72 mL H$_2$O. The resulting mixture was warmed to room temperature and stirred for 15 min. Magnesium sulfate was added and the solids were filtered off. The filter cake was washed with ether and the filtrate was concentrated to afford the product as a colorless oil (180 mg, 67%) that was used without purification.

Step 2. (1-(Iodomethyl)-2-oxabicyclo[2.1.1]hexan-4-yl)methanol

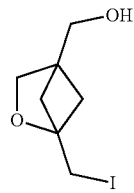

To a solution of (3-methylenecyclobutane-1,1-diyl)dimethanol (1.66 g, 12.95 mmol) in MeCN (50 mL) was added sodium bicarbonate (1.63 g, 19.4 mmol) and N-iodosuccinimide (3.50 g, 15.5 mmol) sequentially. The reaction mixture was stirred at room temperature for 1 h. The reaction was quenched with sat. $NaS_2O_3$, partitioned between water and EtOAc, and the layers were separated. The organic layer was washed with brine, dried over $MgSO_4$, filtered and concentrated. The residue was purified by flash chromatography (0-100% EtOAc/hexanes) to afford the product as a yellow semi-solid (1.97 g, 60%) contaminated with succinimide. $^1$H NMR (400 MHz, $CDCl_3$) δ 3.91 (s, 2H), 3.77 (s, 2H), 3.48 (s, 2H), 1.79-1.70 (m, 2H), 1.70-1.61 (m, 2H). LCMS calculated for $C_7H_{12}IO_2$ (M+H)$^+$: m/z=255.0; found: 255.0.

Step 3. 1-Methyl-2-oxabicyclo[2.1.1]hexane-4-carboxylic Acid

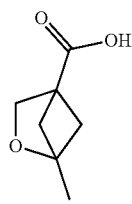

To a solution of (1-(iodomethyl)-2-oxabicyclo[2.1.1]hexan-4-yl)methanol (500 mg, 1.97 mmol) in methanol (6.0 mL) was added Pd—C (10 wt %, 105 mg, 0.098 mmol), followed by triethylamine (0.41 mL, 2.95 mmol). The atmosphere was replaced with hydrogen and the reaction mixture was vigorously stirred under 1 atm of hydrogen for 5 h. The reaction mixture was filtered through a pad of Celite®, concentrated, and the residue was used without further purification.

A solution of (1-methyl-2-oxabicyclo[2.1.1]hexan-4-yl)methanol (250 mg, 1.95 mmol) in $CH_2Cl_2$ (3 mL)/acetonitrile (3.00 mL)/water (3.00 mL) was cooled to 0° C. and stirred rapidly while sodium periodate (1.25 g, 5.9 mmol) and ruthenium(III) chloride hydrate (44.0 mg, 0.20 mmol) were added. The ice bath was removed and the solution was stirred at room temperature for 4 h. The reaction mixture was diluted with EtOAc and stirred while 1 N HCl was added until all solids dissolved. The layers were separated and the aqueous layer was extracted with EtOAc. The combined extracts were washed with 10% $NaHSO_3$ solution, brine, dried over $MgSO_4$, filtered, and concentrated. The residue was purified by flash chromatography (0-20% MeOH/DCM) to afford the title compound (142 mg, 51%).

Step 4. Benzyl 1-methyl-2-oxabicyclo[2.1.1]hexan-4-ylcarbamate

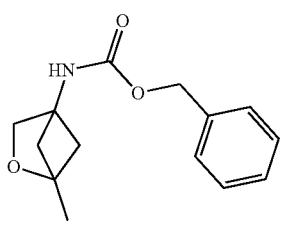 [SMILES: CC12CC(NC(=O)OCc3ccccc3)(CO1)C2]

To a solution of 1-methyl-2-oxabicyclo[2.1.1]hexane-4-carboxylic acid (142 mg, 1.0 mmol) in toluene (3.0 mL) was added triethylamine (0.28 mL, 2.00 mmol), followed by diphenylphosphoryl azide (0.32 mL, 1.50 mmol). The reaction mixture was stirred at room temperature for 1 h, then heated to reflux for 2 h. The reaction mixture was then cooled to room temperature and benzyl alcohol (0.208 mL, 2.0 mmol) was added. The resulting solution was heated to reflux overnight. After cooling to room temperature, the reaction mixture was concentrated in vacuo and purified by flash chromatography (0-50% EtOAc/hexanes) to afford the product as a light yellow solid (contaminated with some benzyl alcohol). $^1$H NMR (400 MHz, $CDCl_3$) δ 7.42-7.35 (m, 5H, overlapped with benzyl alcohol), 5.12 (s, 2H), 3.80 (s, 2H), 2.03-1.87 (m, 3H), 1.75 (m, 1H), 1.46 (s, 3H). LCMS calculated for $C_{14}H_{18}NO_3$ (M+H)$^+$: m/z=248.1; found: 248.1.

Step 5. 1-Methyl-2-oxabicyclo[2.1.1]hexan-4-amine Hydrochloride

To a solution of benzyl (1-methyl-2-oxabicyclo[2.1.1]hexan-4-yl)carbamate (145 mg, 0.59 mmol) in MeOH (4.0 mL) was added Pd—C (10 wt %, 31.2 mg, 29 μmol). The atmosphere was replaced with hydrogen and the reaction mixture was vigorously stirred under 1 atm of hydrogen for 1 h. The reaction mixture was filtered through a pad of Celite®, treated with 4 M HCl/dioxane (to form the hydrochloride salt), concentrated, and the residue was used without purification. LCMS calculated for $C_6H_{12}NO$ (M+H)$^+$: m/z=114.1; found: 114.1.

Intermediate 12. 4,4,5,5-Tetramethyl-2-(2-(methyl-d$_3$)phenyl)-1,3,2-dioxaborolane

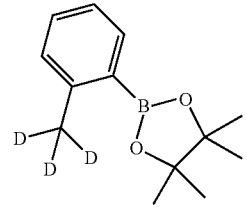

A degassed mixture of 1-bromo-2-(methyl-d$_3$)benzene (0.57 g, 3.3 mmol, Combiphos catalog #032D), 4,4,4',4',5,5,5',5'-octamethyl-2,2'-bi(1,3,2-dioxaborolane) (1.25 g, 4.91 mmol, Aldrich), potassium acetate (1.06 g, 10.8 mmol) and 1,1'-bis(diphenylphosphino)ferrocene-palladium(II)dichloride dichloromethane complex (0.214 g, 0.262 mmol, Aldrich) in dioxane (16.4 mL) was heated to 110° C. for 3 hours. The reaction mixture was cooled to room temperature, diluted with DCM and filtered through Celite®, and the filtrate was concentrated. Purification via flash chromatography, eluting with a gradient of 0-10% EtOAc in hexanes afforded product (647 mg, 89%). LCMS for $C_{13}H_{17}D_3BO_2$ (M+H)$^+$: calculated m/z=222.2, found 222.2.

Intermediate 13. 2-(3-Aminobicyclo[1.1.1]pentan-1-yl)propan-2-ol, Trifluoroacetate Salt

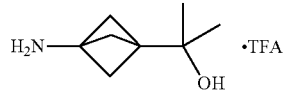

Methyl 3-((tert-butoxycarbonyl)amino)bicyclo[1.1.1]pentane-1-carboxylate (50.0 mg, 0.207 mmol, SpiroChem) in anhydrous THF (3 mL) under $N_2$ and at 0° C. was treated dropwise with methylmagnesium bromide (3.0M in ether, 0.345 mL, 1.04 mmol). After complete addition, the ice bath was removed, and the solution was stirred with warming to room temperature overnight. The reaction was quenched by the addition of sat. $NH_4Cl$ solution (5 mL). The mixture was extracted with two portions of EtOAc. The combined organic extracts were dried over $MgSO_4$, filtered and concentrated. To the crude mixture in DCM (2 mL) was added TFA (0.160 mL, 2.07 mmol), and the reaction was stirred for 1 hour. Solvent was removed in vacuo to afford a clear oil which was used without further purification. Theoretical yield was assumed.

Intermediate 14. 3-Aminobicyclo[1.1.1]pentane-1-carbonitrile Trifluoroacetate Salt

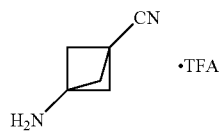

Step 1. 3-((tert-Butoxycarbonyl)amino)bicyclo[1.1.1]pentane-1-carboxylic Acid

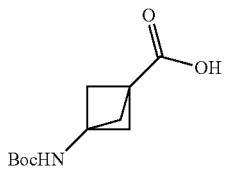 [SMILES: CC(C)(C)OC(=O)NC12CC(C(=O)O)(C1)C2]

A mixture of 3-aminobicyclo[1.1.1]pentane-1-carboxylic acid, HCl (500.0 mg, 3.06 mmol, PharmaBlock) and N,N-diisopropylethylamine (1.0 mL, 6.1 mmol) in THF (10 mL) and water (10 mL) was treated with di-tert-butyl dicarbonate (667 mg, 3.06 mmol). After stirring overnight, the reaction was treated with 1 N HCl to achieve pH 2 and the mixture was extracted with EtOAc. The combined organic extracts were washed with water, followed by brine, dried over $Na_2SO_4$, filtered and concentrated to afford a white solid (665 mg, 96%). LCMS for $C_{11}H_{17}NO_4Na$ (M+Na)$^+$: calculated m/z=250.1; found 250.1.

Step 2. tert-Butyl 3-carbamoylbicyclo[1 J A]pentan-1-ylcarbamate

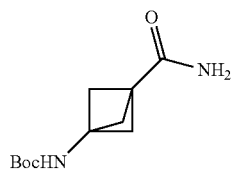 [SMILES: CC(C)(C)OC(=O)NC12CC(C(N)=O)(C1)C2]

A solution of 3-((tert-butoxycarbonyl)amino)bicyclo[1.1.1]pentane-1-carboxylic acid (660 mg, 2.90 mmol) in THF (15 mL) was treated with triethylamine (0.49 mL, 3.5 mmol). The resulting mixture was cooled to −15° C. and ethyl chloroformate (0.31 mL, 3.2 mmol) was added and the mixture was stirred for 1 hour. To the mixture was added ammonium hydroxide solution (19.5 mL). After stirring for 3 hours, volatiles were removed in vacuo, and to the white crude solid was added water. The aqueous suspension was extracted with three portions of EtOAc. The combined organic extracts (containing a fine suspension of product) were dried over $Na_2SO_4$, and the liquid was decanted. Solvent was removed in vacuo to afford a white solid (0.65 g, 100%). LCMS for $C_{11}H_{18}N_2O_3Na$ (M+Na)$^+$: calculated m/z=249.1, found 249.2. $^1$H NMR (400 MHz, DMSO-$d_6$) δ 7.50 (br s, 1H), 7.21 (s, 1H), 6.91 (s, 1H), 2.02 (s, 6H), 1.38 (s, 9H).

Step 3. tert-Butyl 3-cyanobicyclo[7.7.7]pentan-1-ylcarbamate

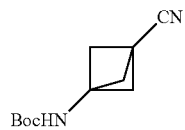

A solution of tert-butyl (3-carbamoylbicyclo[1.1.1]pentan-1-yl)carbamate (200.0 mg, 0.884 mmol) and triethylamine (0.370 mL, 2.65 mmol) in DCM at 0° C. was treated with trichloroacetyl chloride (0.15 mL, 1.3 mmol). After 30 minutes, additional triethylamine (0.37 mL, 3.0 eq) and trichloroacetyl chloride (0.15 mL, 1.5 eq) were added. After an additional 30 minutes, the reaction was quenched by the addition of sat'd. $NaHCO_3$ solution and the aqueous mixture was extracted with EtOAc. The combined organic extracts were dried over $Na_2SO_4$, filtered and concentrated. The residue was purified by flash chromatography, eluting with a gradient from 0-100% EtOAc in hexanes and ELSD was used to detect the product, which was isolated as a white solid (107 mg, 58%). $^1$H NMR (400 MHz, CDCl$_3$) δ 5.08 (s, 1H), 2.49 (s, 6H), 1.46 (s, 9H).

Step 4. 3-Aminobicyclo[7.7.7]pentane-1-carbonitrile Trifluoroacetate Salt tert-Butyl (3-cyanobicyclo[1.1.1]pentan-1-yl)carbamate (40.0 mg, 0.192 mmol) in DCM (2.0 mL) was treated with trifluoroacetic acid (1 mL) and the reaction mixture was stirred for 4 hours. Volatiles were removed in vacuo and the product was used without further purification. Theoretical yield was assumed.

Example 1. 3-(5-Amino-6-(2-methylthiazol-5-yl)pyrazin-2-yl)-N-(3-cyanobicyclo[1.1.1]pentan-1-yl)-4-methylbenzenesulfonamide Trifluoroacetate Salt

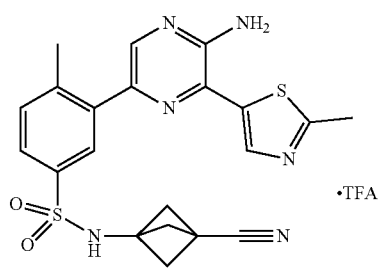 [SMILES: Cc1ncc(-c2nc(-c3cc(S(=O)(=O)NC45CC(C#N)(C4)C5)ccc3C)cnc2N)s1]

Step 1. 5-Chloro-3-(2-methylthiazol-5-yl)pyrazin-2-amine

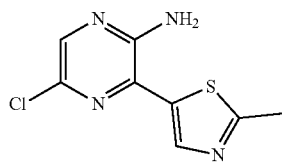

A 40 mL vial was charged with 3-bromo-5-chloropyrazin-2-amine (150 mg, 0.72 mmol, Ark Pharm), cesium fluoride (328 mg, 2.16 mmol), 2-methyl-5-(4,4,5,5-tetramethyl-1,3,2-dioxaborolan-2-yl)thiazole (178 mg, 0.79 mmol, Combi-blocks), bis(di-tert-butyl(4-dimethylaminophenyl)phosphine)dichloropalladium(II) (13 mg, 0.018 mmol), 1-butanol (3 mL), and water (0.75 mL). The mixture was sparged with $N_2$ for 5 min, then heated to 60° C. for 1 h. The reaction mixture was partitioned between water and EtOAc, and the layers were separated. The organic layer was washed with brine, dried over $MgSO_4$, filtered, and concentrated. The residue was purified by flash chromatography (0-100% EtOAc/hexanes) to afford the title compound as a tan solid (140 mg, 86%). LCMS calculated for $C_8H_8ClN_4S$ $(M+H)^+$: m/z=227.0, found: 227.0.

Step 2. 3-(2-Methylthiazol-5-yl)-5-o-tolylpyrazin-2-amine

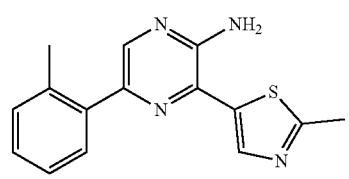 [SMILES: Cc1ncc(-c2nc(-c3ccccc3C)cnc2N)s1]

A 40 mL vial was charged with 5-chloro-3-(2-methylthiazol-5-yl)pyrazin-2-amine (227 mg, 1.00 mmol), o-tolylboronic acid (272 mg, 2.00 mmol), bis(di-tert-butyl(4-dimethylaminophenyl)phosphine)dichloropalladium(II) (17.7 mg, 0.025 mmol), and cesium fluoride (532 mg, 3.50 mmol). 1-Butanol (4 ml) and water (1 ml) were added, and nitrogen was bubbled through the mixture for 5 mins, then the reaction was heated to 90° C. for 1 h. The reaction mixture was partitioned between water and EtOAc, and the layers were separated. The aqueous layer was extracted with EtOAc and the combined organic layers were washed with brine, dried over $MgSO_4$, filtered, and concentrated. The residue was purified by flash chromatography (0-100% EtOAc/hexanes) to afford the title compound (236 mg, 83%). LCMS calculated for $C_{15}H_{15}N_4S$ $(M+H)^+$: m/z=283.1, found: 283.0.

Step 3. 3-(5-Amino-6-(2-methylthiazol-5-yl)pyrazin-2-yl)-4-methylbenzene-1-sulfonyl Chloride

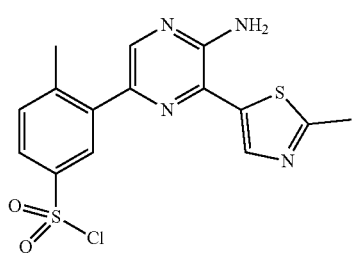 [SMILES: Cc1ncc(-c2nc(-c3cc(S(=O)(=O)Cl)ccc3C)cnc2N)s1]

To a solution of 3-(2-methylthiazol-5-yl)-5-(o-tolyl)pyrazin-2-amine (236 mg, 0.84 mmol) in DCM (4 ml) at 0° C. was added chlorosulfonic acid (0.56 ml, 8.36 mmol). The reaction mixture was allowed to warm to room temperature, and was then heated to 50° C. for 30 min. The reaction was carefully quenched by dropwise addition to a rapidly stirring mixture of DCM and ice. The precipitate that formed was filtered and the solid was washed with water and DCM. The filtrate was transferred to a separatory funnel and the layers were separated. The aqueous layer was extracted with DCM and the combined organic layers were dried over $MgSO_4$, filtered and concentrated to afford a tan solid, which was combined with the solid from the first filtration. The combined solids were triturated with ether to afford the title compound (245 mg, 77%). LCMS calculated for $C_{15}H_{14}ClN_4O_2S_2$ $(M+H)^+$: m/z=381.0, found: 381.0.

Step 4. 3-(5-Amino-6-(2-methylthiazol-5-yl)pyrazin-2-yl)-N-(3-cyanobicyclo[1.1.1]pentan-1-yl)-4-methylbenzenesulfonamide Trifluoroacetate Salt To a solution of 3-aminobicyclo[1.1.1]pentane-1-carbonitrile hydrochloride (6.83 mg, 0.047 mmol, Intermediate 3), and DIPEA (0.021 ml, 0.12 mmol) in DCM (2.0 ml) at 0° C. was added a solution of 3-(5-amino-6-(2-methylthiazol-5-yl)pyrazin-2-yl)-4-methylbenzenesulfonyl chloride (15 mg, 0.039 mmol) in DMA (0.5 mL) dropwise. The 0° C. bath was removed, and the reaction mixture was stirred at room temperature for 1 h. The reaction mixture was concentrated to remove DCM, diluted with MeOH, and purified by prep HPLC (pH 2) to afford the title compound (7.2 mg, 34%). $^1$H NMR (400 MHz, DMSO) δ 8.89 (s, 1H), 8.29 (s, 1H), 8.25 (s, 1H), 7.85 (d, J=2.0 Hz, 1H), 7.71 (dd, J=8.0, 2.0 Hz, 1H), 7.56 (d, J=8.1 Hz, 1H), 2.69 (s, 3H), 2.28 (s, 6H). LCMS calculated for $C_{21}H_{21}N_6O_2S_2$ $(M+H)^+$: m/z=453.1, found: 453.1.

Examples 2-8

Unless otherwise indicted, the compounds of Example 2-8 in Table 1 were synthesized according to the procedure described for Example 1, Step 4, utilizing Intermediates 1 (Example 8) and 4-9 (Examples 2-7).

TABLE 1

| Example No. | Compound Name / ¹H NMR | W | LCMS |
|---|---|---|---|
| 2 | 3-(5-Amino-6-(2-methylthiazol-5-yl)pyrazin-2-yl)-N-(4-cyanobicyclo[2.1.1]hexan-1-yl)-4-methylbenzenesulfonamide trifluoroacetate salt | (4-cyanobicyclo[2.1.1]hexan-1-yl) | Calculated for $C_{22}H_{23}N_6O_2S_2$ $(M+H)^+$: m/z = 467.1, found: 467.1 |
| | ¹H NMR (400 MHz, DMSO) δ 8.66 (s, 1H), 8.29 (s, 1H), 8.24 (s, 1H), 7.89 (d, J = 2.0 Hz, 1H), 7.74 (dd, J = 8.0, 2.0 Hz, 1H), 7.54 (d, J = 8.1 Hz, 1H), 2.69 (s, 3H), 2.50 (s, 3H), 1.99 (m, 2H), 1.94-1.83 (m, 2H), 1.77-1.65 (m, 2H), 1.60 (dd, J = 3.9, 1.8 Hz, 2H). | | |
| 3 | 3-(5-Amino-6-(2-methylthiazol-5-yl)pyrazin-2-yl)-N-(3-(hydroxymethyl)bicyclo[1.1.1]pentan-1-yl)-4-methylbenzenesulfonamide trifluoroacetate salt | (3-(hydroxymethyl)bicyclo[1.1.1]pentan-1-yl) | Calculated from $C_{21}H_{24}N_5O_3S_2$ $(M+H)^+$: m/z = 458.1, found: 458.1 |
| | ¹H NMR (400 MHz, DMSO) δ 8.48 (s, 1H), 8.29 (s, 1H), 8.21 (s, 1H), 7.87 (d, J = 1.8 Hz, 1H), 7.71 (dd, J = 8.0, 1.9 Hz, 1H), 7.53 (d, J = 8.1 Hz, 1H), 3.36 (s, 2H), 2.68 (s, 3H), 1.60 (s, 6H). | | |
| 4 | 3-(5-Amino-6-(2-methylthiazol-5-yl)pyrazin-2-yl)-N-(1-(hydroxymethyl)-2-oxabicyclo[2.1.1]hexan-4-yl)-4-methylbenzenesulfonamide trifluoroacetate salt | (1-(hydroxymethyl)-2-oxabicyclo[2.1.1]hexan-4-yl) | Calculated for $C_{21}H_{24}N_5O_4S_2$ $(M+H)^+$: m/z = 474.1, found: 474.1 |
| | ¹H NMR (400 MHz, DMSO) δ 8.71 (s, 1H), 8.29 (s, 1H), 8.22 (s, 1H), 7.91 (d, J = 1.8 Hz, 1H), 7.75 (dd, J = 8.0, 2.0 Hz, 1H), 7.54 (d, J = 8.1 Hz, 1H), 3.57 (s, 2H), 3.46 (s, 2H), 2.68 (s, 3H), 1.65 (d, J = 4.4 Hz, 2H), 1.41 (dd, J = 4.3, 1.4 Hz, 2H). | | |
| 5 | 3-(5-Amino-6-(2-methylthiazol-5-yl)pyrazin-2-yl)-N-(4-(hydroxymethyl)bicyclo[2.1.1]hexan-1-yl)-4-methylbenzenesulfonamide trifluoroacetate salt | (4-(hydroxymethyl)bicyclo[2.1.1]hexan-1-yl) | Calculated for $C_{22}H_{26}N_5O_3S_2$ $(M+H)^+$: m/z = 472.1, found: 472.1 |
| | ¹H NMR (400 MHz, DMSO) δ 8.29 (s, 2H overlapped), 8.21 (s, 1H), 7.89 (d, J = 1.9 Hz, 1H), 7.72 (dd, J = 8.0, 2.0 Hz, 1H), 7.51 (d, J = 8.1 Hz, 1H), 3.35 (s, 2H), 2.68 (s, 3H), 1.73-1.63 (m, 2H), 1.40 (m, 2H), 1.38-1.32 (m, 2H), 1.04 (dd, J = 3.6, 1.7 Hz, 2H). | | |
| 6 | 3-(5-Amino-6-(2-methylthiazol-5-yl)pyrazin-2-yl)-N-(1-(hydroxymethyl)-2-oxabicyclo[2.2.2]octan-4-yl)-4-methylbenzenesulfonamide trifluoroacetate salt | (1-(hydroxymethyl)-2-oxabicyclo[2.2.2]octan-4-yl) | Calculated for $C_{23}H_{28}N_5O_4S_2$ $(M+H)^+$: m/z = 502.1, found: 502.1 |
| | ¹H NMR (400 MHz, DMSO) δ 8.29 (s, 1H), 8.23 (s, 1H), 7.90 (d, J = 1.8 Hz, 1H), 7.73 (m, J = 3.9 Hz, 2H overlapped), 7.52 (d, J = 8.1 Hz, 1H), 3.62 (s, 2H), 3.09 (s, 2H), 2.69 (s, 3H), 1.81-1.78 (m, 2H), 1.69-1.62 (m, 4H), 1.55 (dt, J = 12.7, 6.8 Hz, 2H). | | |

TABLE 1-continued

| Example No. | Compound Name<br>$^1$H NMR | W | LCMS |
|---|---|---|---|
| 7 | 3-(5-Amino-6-(2-methylthiazol-5-yl)pyrazin-2-yl)-N-(4-hydroxybicyclo[2.2.1]heptan-1-yl)-4-methylbenzenesulfonamide trifluoroacetate salt | | Calculated for $C_{22}H_{26}N_5O_3S_2$ $(M + H)^+$: m/z = 472.1, found: 472.1 |

$^1$H NMR (400 MHz, DMSO) δ 8.29 (s, 1H), 8.22 (s, 1H), 7.95-7.88 (m, 2H), 7.72 (dd, J = 8.0, 1.8 Hz, 1H), 7.51 (d, J = 8.1 Hz, 1H), 2.69 (s, 3H), 1.78-1.74 (m, 2H), 1.55-1.50 (m, 4H), 1.43-1.39 (m, 4H).

| 8 | 3-(5-Amino-6-(2-methylthiazol-5-yl)pyrazin-2-yl)-N-(1-(1-hydroxyethyl)-2-oxabicyclo[2.1.1]hexan-4-yl)-4-methylbenzenesulfonamide trifluoroacetate salt | | Calculated for $C_{22}H_{26}N_5O_4S_2$ $(M + H)^+$: m/z = 488.1, found: 488.0 |

Example 9. 3-(5-Amino-6-(2-methylthiazol-5-yl)pyrazin-2-yl)-5-fluoro-N-(1-(hydroxymethyl)-2-oxabicyclo[2.1.1]hexan-4-yl)-4-methylbenzenesulfonamide trifluoroacetate Salt

Step 1. 3-Bromo-5-fluoro-N-(1-(hydroxymethyl)-2-oxabicyclo[2.1.1]hexan-4-yl)-4-methylbenzenesulfonamide

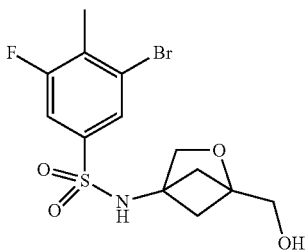 [SMILES: Cc1c(F)cc(S(=O)(=O)NC23COC(CO)(C2)C3)cc1Br]

To a mixture of (4-amino-2-oxabicyclo[2.1.1]hexan-1-yl)methanol (8.9 mg, 0.07 mmol, Intermediate 6) and DIPEA (36 μL, 0.21 mmol) in DCM (4.0 ml) at 0° C., a solution of 3-bromo-5-fluoro-4-methylbenzenesulfonyl chloride (20 mg, 0.07 mmol, Intermediate 10) in DMA (0.5 mL) was added dropwise. The 0° C. bath was removed, and the reaction mixture was stirred at room temperature for 1 h. The reaction mixture was diluted with DCM and washed with water. The organic layer was dried over MgSO$_4$, filtered and concentrated. The residue was purified by flash chromatography (0-100% EtOAc/hexanes) to afford the title compound (24 mg, 91%). LCMS calculated for $C_{13}H_{15}BrFNO_4SNa$ $(M+Na)^+$: m/z=402.0, found: 401.9.

Step 2. 3-Fluoro-N-(1-(hydroxymethyl)-2-oxabicyclo[2.1.1]hexan-4-yl)-4-methyl-5-(4,4,5,5-tetramethyl-1,3,2-dioxaborolan-2-yl)benzenesulfonamide

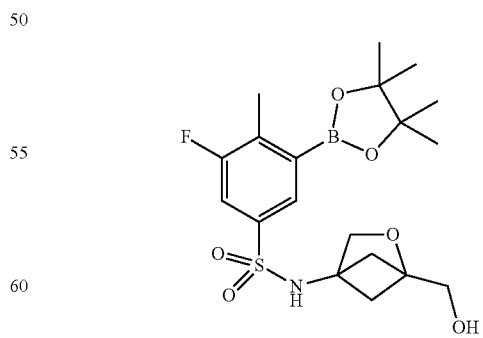

A 40 mL vial was charged with 3-bromo-5-fluoro-N-(1-(hydroxymethyl)-2-oxabicyclo[2.1.1]hexan-4-yl)-4-methylbenzenesulfonamide (24 mg, 0.063 mmol), bis(pinacolato)diboron (19 mg, 0.076 mmol), dichlorobis (triphenylphosphine)-palladium(II) (2.2 mg, 3.2 µmol), and potassium acetate (20 mg, 0.21 mmol). The mixture was placed under nitrogen and dioxane (3 ml) was added. The reaction mixture was sparged with nitrogen for 5 min., then heated to 100° C. for 2 h. After cooling to room temperature, ethyl acetate was added and the mixture was filtered through a pad of Celite®. The volatiles were removed in vacuo and the residue was purified by flash chromatography (0-100% EtOAc/hexanes) to afford the title compound (22 mg, 82%). LCMS calculated for $C_{19}H_{28}BFNO_6S$ (M+H)$^+$: m/z=428.2, found: 428.1.

Step 3. 3-(5-Amino-6-(2-methylthiazol-5-yl)pyrazin-2-yl)-5-fluoro-N-(1-(hydroxymethyl)-2-oxabicyclo[2.1.1]hexan-4-yl)-4-methylbenzenesulfonamide Trifluoroacetate Salt A 40 mL vial was charged with 5-chloro-3-(2-methylthiazol-5-yl)pyrazin-2-amine (11.7 mg, 0.051 mmol), 3-fluoro-N-(1-(hydroxymethyl)-2-oxabicyclo[2.1.1]hexan-4-yl)-4-methyl-5-(4,4,5,5-tetramethyl-1,3,2-dioxaborolan-2-yl)benzenesulfonamide (22 mg, 0.051 mmol), bis(di-tert-butyl(4-dimethylaminophenyl)phosphine)dichloropalladium(II) (1.8 mg, 2.5 µmol), and cesium fluoride (23.5 mg, 0.15 mmol). 1-Butanol (3 ml) and water (0.8 ml) were added, and nitrogen was bubbled through the mixture for 5 mins, then the reaction was heated to 90° C. for 1 h. The reaction mixture was partitioned between water and EtOAc, and the layers were separated. The aqueous layer was extracted with EtOAc and the combined organic layers were washed with brine, dried over MgSO$_4$, filtered, and concentrated. The residue was purified by prep HPLC (pH 2) to afford the title compound. LCMS calculated for $C_{21}H_{23}FN_5O_4S_2$ (M+H)+: m/z=492.1, found: 492.1.

Example 10. 3-(5-Amino-6-(1,3-dimethyl-1H-pyrazol-4-yl)pyrazin-2-yl)-N-(3-cyanobicyclo[1.1.1]pentan-1-yl)-4-methylbenzenesulfonamide Trifluoroacetate Salt

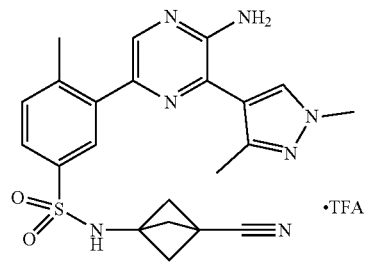 [SMILES: Cc1ccc(S(=O)(=O)NC23CC(C#N)(C2)C3)cc1-c1cnc(N)c(-c2cn(C)nc2C)n1]

This compound was synthesized according to the procedure described for Example 1, utilizing 1,3-dimethyl-4-(4,4,5,5-tetramethyl-1,3,2-dioxaborolan-2-yl)-1H-pyrazole instead of 2-methyl-5-(4,4,5,5-tetramethyl-1,3,2-dioxaborolan-2-yl)thiazole in Step 1. $^1$H NMR (500 MHz, DMSO) δ 8.88 (s, 1H), 8.09 (s, 1H), 8.07 (s, 1H), 7.86 (d, J=2.0 Hz, 1H), 7.69 (dd, J=8.0, 2.0 Hz, 1H), 7.53 (d, J=8.1 Hz, 1H), 3.83 (s, 3H), 2.48 (s, 3H), 2.30 (s, 3H), 2.23 (s, 6H). LCMS calculated for $C_{22}H_{24}N_7O_2S$ (M+H)$^+$: m/z=450.2, found: 450.2.

Examples 11-15

Unless otherwise indicated, the compounds of Examples 11-15 in Table 2 were synthesized by a procedure analogous to that described for Example 1, Step 4 utilizing 3-(5-amino-6-(1,3-dimethyl-1H-pyrazol-4-yl)pyrazin-2-yl)-4-methylbenzene-1-sulfonyl chloride and the appropriate amines. For Example 12, Intermediate 11 was utilized as the amine.

TABLE 2

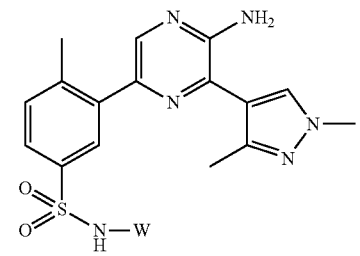

| Example No. | Compound Name / $^1$H NMR | W | LCMS |
|---|---|---|---|
| 11 | 3-(5-Amino-6-(1,3-dimethyl-1H-pyrazol-4-yl)pyrazin-2-yl)-N-(4-cyanobicyclo[2.1.1]hexan-1-yl)-4-methylbenzensulfonamide trifluoroacetate salt | ![structure with CN] | Calculated for $C_{23}H_{26}N_7O_2S$ (M + H)$^+$: m/z = 464.2, found: 464.2 |
| 12 | 3-(5-Amino-6-(1,3-dimethyl-1H-pyrazol-4-yl)pyrazin-2-yl)-4-methyl-N-(1-methyl-2-oxabicyclo[2.1.1]hexan-4-yl)benzenesulfonamide trifluoroacetate salt | ![structure with O and methyl] | Calculated for $C_{22}H_{27}N_6O_3S$ (M + H)$^+$: m/z = 455.2, found: 455.2 |
| 13 | 3-(5-Amino-6-(1,3-dimethyl-1H-pyrazol-4-yl)pyrazin-2-yl)-N-(4-(hydroxymethyl)bicyclo[2.1.1]hexan-1-yl)-4-methylbenzenesulfonamide trifluoroacetate salt | ![structure with OH] | Calculated for $C_{23}H_{29}N_6O_3S$ (M + H)$^+$: m/z = 469.2, found: 469.2 |

TABLE 2-continued

| Example No. | Compound Name | W | LCMS |
|---|---|---|---|
| 14 | 3-(5-Amino-6-(1,3-dimethyl-1H-pyrazol-4-yl)pyrazin-2-yl)-N-(1-(hydroxymethyl)-2-oxabicyclo[2.1.1]hexan-4-yl)-4-methylbenzenesulfonamide trifluoroacetate salt | | Calculated for $C_{22}H_{27}N_6O_4S$ $(M + H)^+$: m/z = 471.2, found: 471.2 |
| 15 | 3-(5-amino-6-(1,3-dimethyl-1H-pyrazol-4-yl)pyrazin-2-yl)-N-(3-(hydroxymethyl)bicyclo[1.1.1]pentan-1-yl)-4-methylbenzenesulfonamide trifluoroacetate salt | | Calculated for $C_{22}H_{27}N_6O_3S$ $(M + H)^+$: m/z = 455.2, found: 455.2 |

$^1$H NMR (400 MHz, DMSO) δ 8.47 (s, 1H), 8.09 (s, 1H), 8.04 (s, 1H), 7.87 (d, J = 1.9 Hz, 1H), 7.68 (dd, J = 8.0, 1.9 Hz, 1H), 7.50 (d, J = 8.1 Hz, 1H), 3.82 (s, 3H), 3.33 (s, 2H), 2.47 (s, 3H), 2.30 (s, 3H), 1.56 (s, 6H).

Example 16. 3-(5-Amino-6-(pyridin-3-yl)pyrazin-2-yl)-N-(4-hydroxybicyclo[2.2.1]heptan-1-yl)-4-methylbenzenesulfonamide Trifluoroacetate Salt

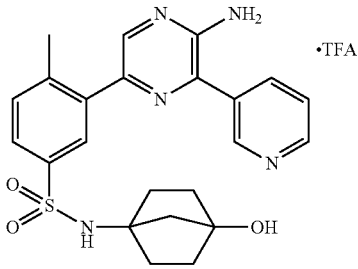 [SMILES: Cc1ccc(S(=O)(=O)NC23CCC(O)(CC2)C3)cc1-c1cnc(N)c(-c2cccnc2)n1]

Step 1. N-(4-Hydroxybicyclo[2.2.1]heptan-1-yl)-4-methyl-3-(4,4,5,5-tetramethyl-1,3,2-dioxaborolan-2-yl)benzenesulfonamide

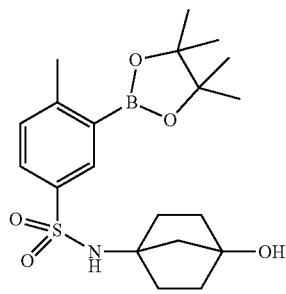 [SMILES: Cc1ccc(S(=O)(=O)NC23CCC(O)(CC2)C3)cc1B1OC(C)(C)C(C)(C)O1]

This compound was synthesized according to the procedure described for Example 9, Steps 1-2, utilizing 4-aminobicyclo[2.2.1]heptan-1-ol hydrochloride (Intermediate 9) and 3-bromo-4-methylbenzene-1-sulfonyl chloride instead of (4-amino-2-oxabicyclo[2.1.1]hexan-1-yl)methanol and 3-bromo-5-fluoro-4-methylbenzenesulfonyl chloride in Step 1. LCMS calculated for $C_{20}H_{31}BNO_5S$ $(M+H)^+$: m/z=408.2, found: 408.2.

Step 2. 3-(5-Amino-6-chloropyrazin-2-yl)-N-(4-hydroxybicyclo[2.2.1]heptan-1-yl)-4-methylbenzenesulfonamide

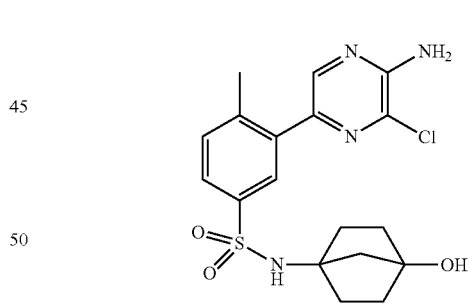

A 40 mL vial was charged with 5-bromo-3-chloropyrazin-2-amine (124 mg, 0.59 mmol), 7V-(4-hydroxybicyclo[2.2.1]heptan-1-yl)-4-methyl-3-(4,4,5,5-tetramethyl-1,3,2-dioxaborolan-2-yl)benzenesulfonamide (187 mg, 0.46 mmol), bis(di-tert-butyl(4-dimethylaminophenyl)phosphine)dichloropalladium(II) (16.3 mg, 0.023 mmol), and cesium fluoride (209 mg, 1.38 mmol). 1-Butanol (3 ml) and water (0.8 ml) were added, and nitrogen was bubbled through the mixture for 5 mins, then the reaction was heated to 60° C. for 1 h. The reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-100% EtOAc/hexanes) to afford the title compound (100 mg, 53%). LCMS calculated for $C_{18}H_{22}ClN_4O_3S$ (M+H)+: m/z=409.1, found: 409.1.

Step 3. 3-(5-Amino-6-(pyridin-3-yl)pyrazin-2-yl)-N-(4-hydroxybicyclo[2.2.1]heptan-1-yl)-4-methylbenzenesulfonamide Trifluoroacetate Salt A crimp-cap vial was charged with 3-(5-amino-6-chloropyrazin-2-yl)-N-(4-hydroxybicyclo[2.2.1]heptan-1-yl)-4-methylbenzenesulfonamide (10 mg, 0.024 mmol), 3-(4,4,5,5-tetramethyl-1,3,2-dioxaborolan-2-yl)pyridine (15 mg, 0.073 mmol), bis(di-tert-butyl(4-dimethylaminophenyl)phosphine)dichloropalladium(II) (0.9 mg, 1.2 μmol), and cesium fluoride (11 mg, 0.073 mmol). 1-Butanol (2 ml) and water (0.5 ml) were added, and nitrogen was bubbled through the mixture for 5 mins, then the reaction mixture was heated to 90° C. for 1 h. The reaction mixture was partitioned between water and EtOAc, and the layers were separated. The aqueous layer was extracted with EtOAc and the combined organic layers were washed with brine, dried over MgSO₄, filtered, and concentrated. The residue was purified by prep HPLC (pH 2) to afford the title compound. ¹H NMR (500 MHz, DMSO) δ 9.11 (d, J=1.8 Hz, 1H), 8.80 (dd, J=5.2, 1.4 Hz, 1H), 8.51 (dt, J=8.0, 1.7 Hz, 1H), 8.30 (s, 1H), 7.92 (app d, J=2.2 Hz, 2H), 7.84 (dd, J=8.0, 5.3 Hz, 1H), 7.72 (dd, J=8.0, 2.0 Hz, 1H), 7.51 (d, J=8.1 Hz, 1H), 1.76 (dt, J=14.4, 7.7 Hz, 2H), 1.51-1.47 (m, 4H), 1.44-1.34 (m, 4H). LCMS calculated for $C_{23}H_{26}N_5O_3S$ (M+H)+: m/z=452.2, found: 452.2.

Example 17. 3-(5-Amino-6-(pyridin-4-yl)pyrazin-2-yl)-N-(4-hydroxybicyclo[2.2.1]heptan-1-yl)-4-methylbenzenesulfonamide Trifluoroacetate Salt

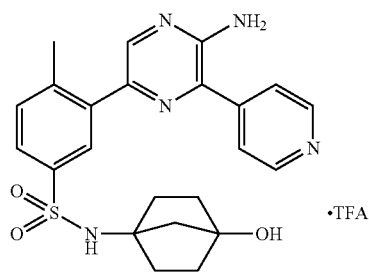 [SMILES: Cc1ccc(S(=O)(=O)NC23CCC(O)(CC2)C3)cc1-c1cnc(N)c(-c2ccncc2)n1]

This compound was synthesized according to the procedure described for Example 16, utilizing 4-(4,4,5,5-tetramethyl-1,3,2-dioxaborolan-2-yl)pyridine instead of 3-(4,4,5,5-tetramethyl-1,3,2-dioxaborolan-2-yl)pyridine in Step 3. ¹H NMR (500 MHz, DMSO) δ 8.90-8.87 (m, 1H), 8.38 (s, 1H), 8.22-8.17 (m, 1H), 7.93 (d, J=2.0 Hz, 1H), 7.92 (s, 1H), 7.74 (dd, J=8.0, 2.0 Hz, 1H), 7.52 (d, J=8.1 Hz, 1H), 1.79-1.73 (m, 2H), 1.55-1.45 (m, 4H), 1.45-1.34 (m, 4H). LCMS calculated for $C_{23}H_{26}N_5O_3S$ (M+H)+: m/z=452.2, found: 452.2.

Example 18. 3-(5-Amino-6-(2-methylpyridin-4-yl)pyrazin-2-yl)-N-(1-(hydroxymethyl)-2-oxabicyclo[2.2.2]octan-4-yl)-4-methylbenzenesulfonamide Trifluoroacetate Salt

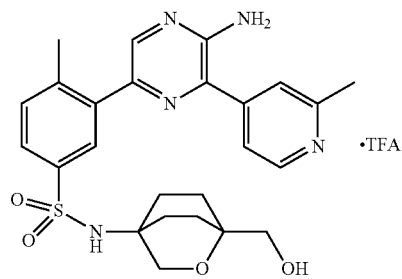 [SMILES: Cc1cc(-c2nc(-c3cc(S(=O)(=O)NC45CCC(CO)(CC4)OC5)ccc3C)cnc2N)ccn1]

Step 1. 3-Chloro-5-o-tolylpyrazin-2-amine

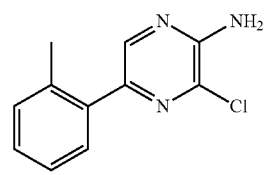

A crimp-cap vial was charged with 5-bromo-3-chloropyrazin-2-amine (200 mg, 0.96 mmol), o-tolylboronic acid (130 mg, 0.96 mmol), bis(di-tert-butyl(4-dimethylaminophenyl)phosphine)dichloropalladium(II) (17 mg, 0.024 mmol), and cesium fluoride (437 mg, 2.88 mmol). Butan-1-ol (3 ml) and water (0.8 ml) were added, and nitrogen was bubbled through the mixture for 5 mins, then the reaction was heated to 60° C. for 1 h. The reaction mixture was partitioned between water and EtOAc, and the layers were separated. The aqueous layer was extracted with EtOAc and the combined organic layers were washed with brine, dried over MgSO₄, filtered, and concentrated. The residue was purified by flash chromatography (0-100% EtOAc/hexanes) to afford the title compound (211 mg, quant.). LCMS calculated for $C_{11}H_{11}ClN_3$ (M+H)+: m/z=220.1, found: 220.1.

Step 2. 3-(5-amino-6-chloropyrazin-2-yl)-4-methylbenzene-1-sulfonyl Chloride

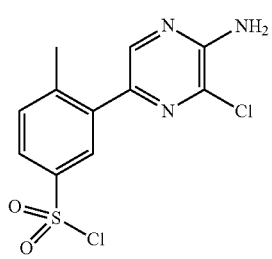 [SMILES: Cc1ccc(S(=O)(=O)Cl)cc1-c1cnc(N)c(Cl)n1]

To a solution of 3-chloro-5-(o-tolyl)pyrazin-2-amine (210 mg, 0.96 mmol) in DCM (4 ml) at 0° C. was added chlorosulfonic acid (0.64 ml, 9.56 mmol). The reaction mixture was allowed to warm to room temperature, and was then heated to 50° C. for 30 min. The reaction was carefully quenched by dropwise addition to a rapidly stirring mixture of DCM and ice. The mixture was transferred to a separatory funnel and shaken until complete dissolution, then the layers were separated. The aqueous layer was extracted with DCM and the combined organic layers were dried over $MgSO_4$, filtered and concentrated to afford the title compound as a yellow solid (287 mg, 94%). LCMS calculated for $C_{11}H_{10}Cl_2N_3O_2S$ $(M+H)^+$: m/z=318.0, found: 318.0.

Step 3. 3-(5-Amino-6-chloropyrazin-2-yl)-N-(1-(hydroxymethyl)-2-oxabicyclo[2.2.2]octan-4-yl)-4-methylbenzenesulfonamide

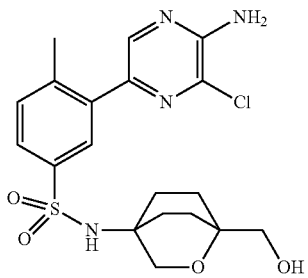 [SMILES: Cc1ccc(S(=O)(=O)NC23CCC(CO)(CC2)OC3)cc1-c1cnc(N)c(Cl)n1]

To a suspension of (4-amino-2-oxabicyclo[2.2.2]octan-1-yl)methanol hydrochloride (227 mg, 1.17 mmol) and DIPEA (0.47 ml, 2.71 mmol) in DCM (3.0 ml) at 0° C. was added a solution of 3-(5-amino-6-chloropyrazin-2-yl)-4-methylbenzenesulfonyl chloride (287 mg, 0.90 mmol) in DCM (3 mL) dropwise. The 0° C. bath was removed, and the reaction mixture was stirred at room temperature for 3 h. Conversion was low so DMA (2 mL) was added to solubilize the reaction mixture. After stirring overnight, complete conversion to the desired product was observed by LCMS. The reaction mixture was partitioned between water and EtOAc, and the layers were separated. The aqueous layer was extracted with EtOAc and the combined organic layers were washed with brine, dried over MgSO4, filtered, and concentrated. The residue was purified by flash chromatography (0-100% EtOAc/hexanes) to afford the title compound as a yellow oil. LCMS calculated for $C_{19}H_{24}ClN_4O_4S$ $(M+H)^+$: m/z=439.1, found: 439.2.

Step 4. 3-(5-Amino-6-(2-methylpyridin-4-yl)pyrazin-2-yl)-N-(1-(hydroxymethyl)-2-oxabicyclo[2.2.2]octan-4-yl)-4-methylbenzenesulfonamide Trifluoroacetate Salt A vial was charged with 3-(5-amino-6-chloropyrazin-2-yl)-N-(1-(hydroxymethyl)-2-oxabicyclo[2.2.2]octan-4-yl)-4-methylbenzenesulfonamide (15 mg, 0.034 mmol), 2-methyl-4-(4,4,5,5-tetramethyl-1,3,2-dioxaborolan-2-yl)pyridine (22 mg, 0.10 mmol), bis(di-tert-butyl(4-dimethylaminophenyl)phosphine)dichloropalladium(II) (1.2 mg, 1.7 μmol), and cesium fluoride (16 mg, 0.10 mmol). Butan-1-ol (2 ml) and water (0.5 ml) were added, and nitrogen was bubbled through the mixture for 5 min, then the reaction mixture was heated to 90° C. for 1 h. The reaction mixture was partitioned between water and EtOAc, and the layers were separated. The aqueous layer was extracted with EtOAc and the combined organic layers were washed with brine, dried over $MgSO_4$, filtered, and concentrated. The residue was purified by prep HPLC (pH 2) to afford the title compound. LCMS calculated for $C_{25}H_{30}N_5O_4S$ $(M+H)^+$: m/z=496.2, found: 496.2.

Examples 19-22

Unless otherwise indicted, the compounds of Examples 19-22 in Table 3 were prepared according to the procedure described for Example 18, Step 4 utilizing the appropriate pyridine boronates.

TABLE 3

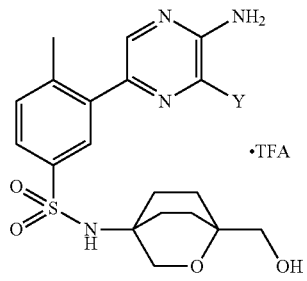

| Example No. | Compound Name | Y | LCMS |
|---|---|---|---|
| 19 | 3-(5-Amino-6-(2-cyanopyridin-4-yl)pyrazin-2-yl)-N-(1-(hydroxymethyl)-2-oxabicyclo[2.2.2]octan-4-yl)-4-methylbenzenesulfonamide trifluoroacetate salt | | Calculated for $C_{25}H_{27}N_6O_4S$ $(M + H)^+$: m/z = 507.2, found: 507.2 |
| 20 | 3-(5-Amino-6-(3-fluoropyridin-4-yl)pyrazin-2-yl)-N-(1-(hydroxymethyl)-2-oxabicyclo[2.2.2]octan-4-yl)-4-methylbenzenesulfonamide trifluoroacetate salt | | Calculated for $C_{24}H_{27}FN_5O_4S$ $(M + H)^+$: m/z = 500.2, found: 500.1 |

TABLE 3-continued

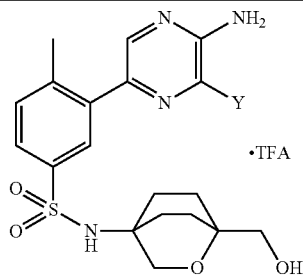

·TFA

| Example No. | Compound Name | Y | LCMS |
|---|---|---|---|
| 21 | 3-(5-Amino-6-(2-(trifluoromethyl)pyridin-4-yl)pyrazin-2-yl)-N-(1-(hydroxymethyl)-2-oxabicyclo[2.2.2]octan-4-yl)-4-methylbenzenesulfonamide trifluoroacetate salt | 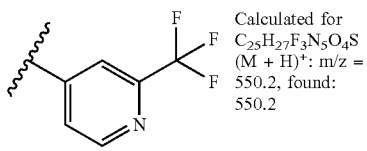 | Calculated for $C_{25}H_{27}F_3N_5O_4S$ $(M + H)^+$: m/z = 550.2, found: 550.2 |
| 22 | 3-(5-Amino-6-(3-cyanopyridin-4-yl)pyrazin-2-yl)-N-(1-(hydroxymethyl)-2-oxabicyclo[2.2.2]octan-4-yl)-4-methylbenzenesulfonamide trifluoroacetate salt | 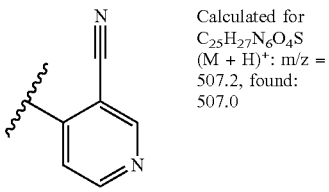 | Calculated for $C_{25}H_{27}N_6O_4S$ $(M + H)^+$: m/z = 507.2, found: 507.0 |

Example 23. 3-(5-Amino-6-(1H-1,2,4-triazol-1-yl)pyrazin-2-yl)-N-(3-cyanobicyclo[1.1.1]pentan-1-yl)-4-methylbenzenesulfonamide Trifluoroacetate Salt

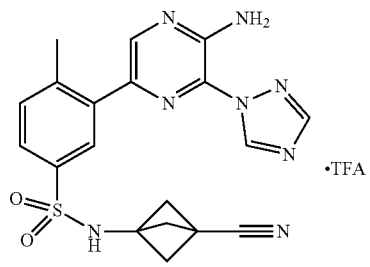 [SMILES: Cc1ccc(S(=O)(=O)NC23CC(C#N)(C2)C3)cc1-c1cnc(N)c(-n2cncn2)n1]

Step 1. 5-Bromo-3-(1H-1,2,4-triazol-1-yl)pyrazin-2-amine

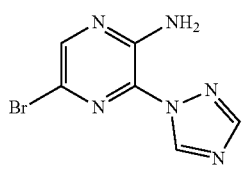 [SMILES: Nc1ncc(Br)nc1-n1cncn1]

To a solution of 5-bromo-3-chloropyrazin-2-amine (200 mg, 0.96 mmol) and 1,2,4-triazole (199 mg, 2.88 mmol) in DMF (4.0 ml) was added cesium carbonate (938 mg, 2.88 mmol) and the reaction mixture was heated to 60° C. for 1.5 h. The reaction mixture was partitioned between water and EtOAc, and the layers were separated. The aqueous layer was extracted with EtOAc and the combined organic layers were washed with brine, dried over MgSO₄, filtered, and concentrated. The residue was purified by flash chromatography (0-75% EtOAc/hexanes) to afford the title compound (192 mg, 83%). LCMS calculated for $C_6H_6BrN_6$ $(M+H)^+$: m/z=241.0, found: 241.0.

Step 2. 5-o-Tolyl-3-(1H-1,2,4-triazol-1-yl)pyrazin-2-amine

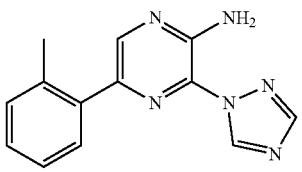 [SMILES: Cc1ccccc1-c1cnc(N)c(-n2cncn2)n1]

A 40 mL vial was charged with 5-bromo-3-(1H-1,2,4-triazol-1-yl)pyrazin-2-amine (192 mg, 0.79 mmol), o-tolyl-boronic acid (162 mg, 1.20 mmol), bis(di-tert-butyl(4-dimethylaminophenyl)phosphine)dichloropalladium(II) (14 mg, 0.020 mmol), and cesium fluoride (363 mg, 2.39 mmol). Butan-1-ol (3 ml) and water (0.75 ml) were added, and nitrogen was bubbled through the mixture for 5 min, then the reaction was heated to 90° C. for 1 h. The reaction mixture was partitioned between water and EtOAc, and the layers were separated. The aqueous layer was extracted with EtOAc and the combined organic layers were washed with brine, dried over MgSO₄, filtered, and concentrated. The residue was purified by flash chromatography (0-50%

EtOAc/hexanes) to afford the title compound (198 mg, 99%). LCMS calculated for $C_{13}H_{13}N_6$ $(M+H)^+$: m/z=253.1, found: 253.1.

Step 3. 3-(5-Amino-6-(1H-1,2,4-triazol-1-yl)pyrazin-2-yl)-4-methylbenzene-1-sulfonyl chloride

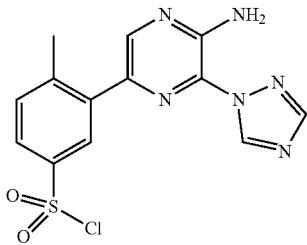 [SMILES: Cc1ccc(S(=O)(=O)Cl)cc1-c1cnc(N)c(-n2cncn2)n1]

To a solution of 5-(o-tolyl)-3-(1H-1,2,4-triazol-1-yl)pyrazin-2-amine (198 mg, 0.79 mmol) in DCM (3 ml) at 0° C. was added chlorosulfonic acid (0.53 ml, 7.85 mmol). The reaction mixture was allowed to warm to room temperature, and was then heated to 50° C. for 0.5 h. The reaction was carefully quenched by dropwise addition to a rapidly stirring mixture of DCM and ice. The precipitate was filtered and washed with DCM (LCMS indicated the precipitate was desired product). The filtrate was transferred to a separatory funnel and the layers were separated. The aqueous layer was extracted with DCM and the combined organic layers were dried over $MgSO_4$, filtered and concentrated to an off white solid. The solids were combined and air dried to afford the title compound (230 mg, 84%). LCMS calculated for $C_{13}H_{12}ClN_6O_2S$ $(M+H)^+$: m/z=351.1, found: 351.0.

Step 4. 3-(5-Amino-6-(1H-1,2,4-triazol-1-yl)pyrazin-2-yl)-N-(3-cyanobicyclo[1.1.1]pentan-1-yl)-4-methylbenzenesulfonamide Trifluoroacetate Salt This compound was synthesized by a procedure analogous to that described for Example 1, Step 4. $^1$H NMR (500 MHz, DMSO) δ 9.33 (s, 1H), 8.94 (s, 1H), 8.42 (s, 1H), 8.41 (s, 1H), 7.91 (d, J=2.0 Hz, 1H), 7.74 (dd, J=8.0, 2.0 Hz, 1H), 7.57 (d, J=8.1 Hz, 1H), 2.53 (s, 3H), 2.25 (s, 6H). LCMS calculated for $C_{19}H_{19}N_8O_2S$ $(M+H)^+$: m/z=423.1, found: 423.1.

Examples 24-29

Unless otherwise indicted, the compounds of Examples 24-29 in Table 4 were synthesized according to the procedure described for Example 1, Step 4 utilizing 3-(5-amino-6-(1H-1,2,4-triazol-1-yl)pyrazin-2-yl)-4-methylbenzene-1-sulfonyl chloride and the appropriate amines. For Example 29, Intermediate 13 was utilized as the amine.

TABLE 4

| Example No. | Compound Name $^1$H NMR | W | LCMS |
|---|---|---|---|
| 24 | 3-(5-Amino-6-(1H-1,2,4-triazol-1-yl)pyrazin-2-yl)-N-(3-(hydroxymethyl)bicyclo[1.1.1]pentan-1-yl)-4-methylbenzenesulfonamide trifluoroacetate salt | bicyclo[1.1.1]pentane-CH2OH | Calculated for $C_{19}H_{22}N_7O_3S$ $(M + H)^+$: m/z = 428.1, found: 428.1 |
| | $^1$H NMR (500 MHz, DMSO) δ 9.33 (s, 1H), 8.42 (s, 1H), 8.39 (s, 1H), 7.94 (d, J = 2.1 Hz, 1H), 7.73 (dd, J = 8.0, 2.0 Hz, 1H), 7.55 (d, J = 8.1 Hz, 1H), 3.34 (s, 2H), 2.53 (s, 3H), 1.58 (s, 6H). | | |
| 25 | 3-(5-Amino-6-(1H-1,2,4-triazol-1-yl)pyrazin-2-yl)-N-(4-(hydroxymethyl)bicyclo[2.1.1]hexan-1-yl)-4-methylbenzenesulfonamide trifluoroacetate salt | bicyclo[2.1.1]hexane-CH2OH | Calculated for $C_{20}H_{24}N_7O_3S$ $(M + H)^+$: m/z = 442.2, found: 442.1 |
| 26 | 3-(5-Amino-6-(1H-1,2,4-triazol-1-yl)pyrazin-2-yl)-N-(4-hydroxybicyclo[2.2.1]heptan-1-yl)-4-methylbenzenesulfonamide trifluoroacetate salt | bicyclo[2.2.1]heptane-OH | Calculated for $C_{20}H_{24}N_7O_3S$ $(M + H)^+$: m/z = 442.2, found: 442.1 |

TABLE 4-continued

[Structure: 3-methylphenyl-pyrazine with NH2, 1,2,4-triazol-1-yl, and sulfonamide-NH-W group]

| Example No. | Compound Name / ¹H NMR | W | LCMS |
|---|---|---|---|
| 27 | 3-(5-Amino-6-(1H-1,2,4-triazol-1-yl)pyrazin-2-yl)-N-(1-(hydroxymethyl)-2-oxabicyclo[2.1.1]hexan-4-yl)-4-methylbenzenesulfonamide trifluoroacetate salt | [2-oxabicyclo[2.1.1]hexane with CH2OH substituent] | Calculated for C₁₉H₂₂N₇O₄S (M + H)⁺: m/z = 444.1, found: 444.1 |
| 28 | 3-(5-Amino-6-(1H-1,2,4-triazol-1-yl)pyrazin-2-yl)-N-(4-cyanobicyclo[2.1.1]hexan-1-yl)-4-methylbenzenesulfonamide trifluoroacetate salt <br> ¹H NMR (600 MHz, DMSO) δ 9.33 (s, 1H), 8.70 (s, 1H), 8.42 (s, 1H), 8.41 (s, 1H), 7.95 (d, J = 2.1 Hz, 1H), 7.76 (dd, J = 8.0, 2.1 Hz, 1H), 7.56 (d, J = 8.1 Hz, 1H), 2.53 (s, 3H), 2.01-1.93 (m, 2H), 1.88-1.86 (m, 2H), 1.73-1.66 (m, 2H), 1.58 (dd, J = 4.0, 1.9 Hz, 2H). | [bicyclo[2.1.1]hexane with CN substituent] | Calculated for C₂₀H₂₁N₈O₂S (M + H)⁺: m/z = 437.1, found: 437.1 |
| 29 | 3-(5-Amino-6-(1H-1,2,4-triazol-1-yl)pyrazin-2-yl)-N-(3-(2-hydroxypropan-2-yl)bicyclo[1.1.1]pentan-1-yl)-4-methylbenzenesulfonamide trifluoroacetate salt | [bicyclo[1.1.1]pentane with C(CH3)2OH substituent] | Calculated for C₂₁H₂₆N₇O₃S (M + H)⁺: m/z = 456.2, found: 456.1 |

*In Example 29, 2-(3-aminobicyclo[1.1.1]pentan-1-yl)propan-2-ol.

Example 30. 3-(5-Amino-6-(1H-1,2,4-triazol-1-yl)pyrazin-2-yl)-N-(4-hydroxybicyclo[2.1.1]hexan-1-yl)-4-methylbenzenesulfonamide Trifluoroacetate Salt

[Structure of Example 30 compound ·TFA]

Step 1. 4-Aminobicyclo[2.1.1]hexane-1-carboxylic Acid

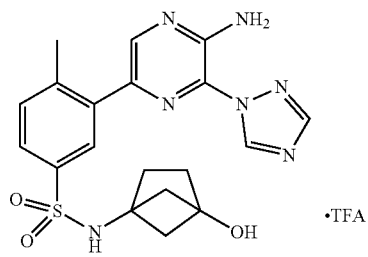 [SMILES: Cc1ccc(S(=O)(=O)NC23CCC(O)(C2)C3)cc1-c1cnc(N)c(-n2cncn2)n1]

To 4-((tert-Butoxycarbonyl)amino)bicyclo[2.1.1]hexane-1-carboxylic acid (200.0 mg, 0.829 mmol, Spirochem) was added 4 N HCl in dioxane (1.0 mL, 4.0 mmol) and the reaction was stirred for 3 hours. Volatiles were removed in vacuo and the product was used crude in the next step (117 mg, 100%).

Step 2. 4-Hydroxybicyclo[2.1.1]hexane-1-carboxylic Acid

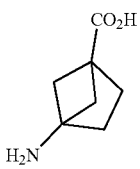

Sodium nitrite (182 mg, 2.63 mmol) in water (0.2 mL) was added dropwise to a 10° C. mixture of 4-aminobicyclo[2.1.1]hexane-1-carboxylic acid (117 mg, 0.829 mmol) and 10% acetic acid in water (1.2 mL). The mixture was then heated to 65° C. and stirred at this temperature overnight. The reaction mixture was then cooled to 5° C. and potassium hydroxide (370 mg, 6.6 mmol) in MeOH (0.8 mL) was added dropwise. The reaction was again heated to 65° C. for 3 hours. The reaction mixture was cooled to room temperature and water was added. The aqueous mixture was washed with EtOAc (2×). The aqueous layer was cooled to 0° C. and acidified by the addition of 1 N HCl to pH 3. This acidic aqueous mixture was extracted with EtOAc (4×). The organic extracts of the acidic aqueous layer were dried over MgSO$_4$, filtered and concentrated to afford product which was used without further purification (80.0 mg, 68%).

Step 3. Benzyl (4-hydroxybicyclo[2.1.1]hexan-1-yl) carbamate

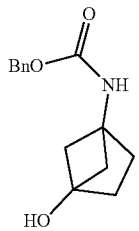

4-Hydroxybicyclo[2.1.1]hexane-1-carboxylic acid (70.0 mg, 0.49 mmol) in toluene (1 mL) was cooled to 10° C. and was treated with benzyl alcohol (230 μL, 2.2 mmol). The reaction mixture was then treated with DIEA (150 μL, 0.86 mmol) and diphenylphosphoryl azide (115 μL, 0.54 mmol). The reaction mixture was then slowly heated to 110° C. overnight. The reaction mixture was concentrated to remove solvent and was partitioned between EtOAc and brine. The organic layer was dried over MgSO$_4$, filtered and concentrated. The residue was slurried in DCM and filtered to remove reagent byproducts and the filtrate was purified by flash chromatography, eluting with a gradient of 0-100% EtOAc in hexanes (50.0 mg, 41%). $^1$H NMR (400 MHz, CD$_3$OD) δ 7.47-7.15 (m, 5H), 5.14-5.01 (m, 2H), 1.88-1.77 (m, 4H), 1.76-1.72 (m, 2H), 1.72-1.63 (m, 2H).

Step 4. 4-Aminobicyclo[2.1.1]hexan-1-ol, hydrochloric Acid Salt

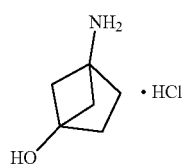

To a solution of benzyl (4-hydroxybicyclo[2.1.1]hexan-1-yl)carbamate (25 mg, 0.10 mmol) in MeOH (2 mL) and water (1 mL) was added palladium (10 mg of 10% on carbon) and the reaction mixture was shaken under H$_2$ at 30 psi for 3 hours. The reaction mixture was filtered and MeOH was removed in vacuo. The resulting aqueous mixture was adjusted to pH 3 by the addition of 1 N HCl and was washed with EtOAc to remove impurities. The aqueous mixture was then lyophilized to afford product as the HCl salt (7.0 mg, 47%).

Step 5. 3-(5-Amino-6-(1H-1,2,4-triazol-1-yl) pyrazin-2-yl)-N-(4-hydroxybicyclo[2.1.1]hexan-1-yl)-4-methylbenzenesulfonamide Trifluoroacetate Salt This compound was synthesized by a procedure analogous to that described for Example 23. LCMS calculated for C$_{19}$H$_{22}$N$_7$O$_3$S (M+H)$^+$: m/z=428.1, found: 428.1.

Example 31. (3-(3-(5-Amino-6-(1H-1,2,4-triazol-1-yl)pyrazin-2-yl)-4-methylphenylsulfonamido)bicyclo [1.1.1]pentan-1-yl)methyl Methylcarbamate Trifluoroacetate Salt

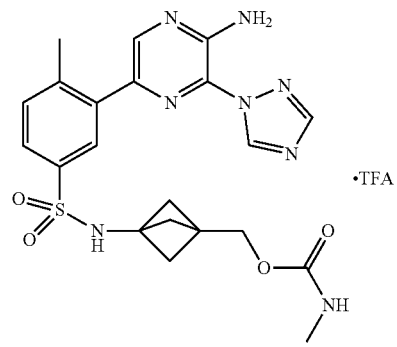 [SMILES: CNC(=O)OCC12CC(NS(=O)(=O)c3ccc(C)c(-c4cnc(N)c(-n5cncn5)n4)c3)(C1)C2]

To a solution of 3-(5-amino-6-(1H-1,2,4-triazol-1-yl) pyrazin-2-yl)-N-(3-(hydroxymethyl)bicyclo[1.1.1]pentan-1-yl)-4-methylbenzenesulfonamide (10 mg, 0.023 mmol, Example 24) in THF (1.0 ml) was added sodium hydride (4.7 mg, 0.12 mmol), followed by methylaminoformyl chloride (11 mg, 0.12 mmol), and the reaction mixture was heated to 60° C. for 3 h. After cooling to 0° C., the reaction was quenched by the dropwise addition of MeOH, followed by water. The resulting solution was diluted with MeOH and purified by prep HPLC (pH 2) to afford the title compound. LCMS calculated for C$_{21}$H$_{25}$N$_8$O$_4$S (M+H)$^+$: m/z=485.2, found: 485.2.

Example 32. 3-(3-(5-Amino-6-(1H-1,2,4-triazol-1-yl)pyrazin-2-yl)-4-methylphenylsulfonamido)-N-methylbicyclo[1.1.1]pentane-1-carboxamide trifluoroacetate Salt

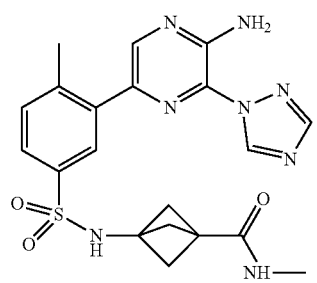 [SMILES: CNC(=O)C12CC(NS(=O)(=O)c3ccc(C)c(-c4cnc(N)c(-n5cncn5)n4)c3)(C1)C2]

Step 1. Methyl 3-(tert-butoxycarbonylamino)bicyclo [1.1.1]pentane-1-carboxylate

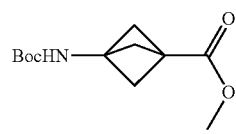 [SMILES: COC(=O)C12CC(NC(=O)OC(C)(C)C)(C1)C2]

To a solution of 3-((tert-butoxycarbonyl)amino)bicyclo [1.1.1]pentane-1-carboxylic acid (208 mg, 0.92 mmol) in methanol (4.0 ml) at 0° C. was added (trimethylsilyl)diazomethane solution (2.0 M in hexanes, 0.69 ml, 1.37 mmol). The ice bath was removed and the reaction mixture was stirred at room temperature for 1 h. The solution was concentrated in vacuo and the resulting white solid was used without purification.

Step 2. Methyl 3-aminobicyclo[1.1.1]pentane-1-carboxylate Hydrochloride

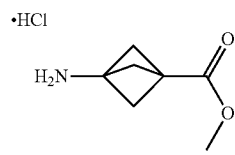

Methyl 3-((tert-butoxycarbonyl)amino)bicyclo[1.1.1]pentane-1-carboxylate (221 mg, 0.92 mmol) was stirred in HCl (4.0 M in dioxane) (4 mL, 16.0 mmol) for 1 h. Ether was added and the white precipitate was filtered and air dried to yield the title compound (150 mg, 92%). LCMS calculated for $C_7H_{12}NO_2$ (M+H)$^+$: m/z=142.1, found: 142.1.

Step 3. Methyl 3-(3-(5-amino-6-(1H-1,2,4-triazol-1-yl)pyrazin-2-yl)-4-methylphenylsulfonamido)bicyclo[1.1.1]pentane-1-carboxylate

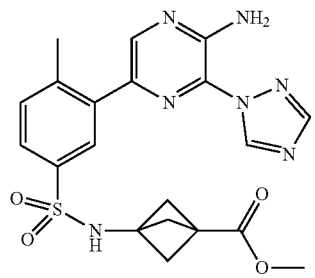 [SMILES: COC(=O)C12CC(NS(=O)(=O)c3ccc(C)c(-c4cnc(N)c(-n5cncn5)n4)c3)(C1)C2]

To a solution of methyl 3-aminobicyclo[1.1.1]pentane-1-carboxylate hydrochloride (45 mg, 0.26 mmol) and DIPEA (90 µL, 0.51 mmol) in DCM (3.0 ml) at 0° C. was added a solution of 3-(5-amino-6-(1H-1,2,4-triazol-1-yl)pyrazin-2-yl)-4-methylbenzenesulfonyl chloride (60 mg, 0.17 mmol, Example 23, Step 3) in DMA (0.5 mL) dropwise. The 0° C. bath was removed, and the reaction mixture was stirred at room temperature for 1 h. The reaction mixture was concentrated to remove DCM and purified by flash chromatography (0-100% EtOAc/hexanes). DMA that remained in the product was removed on the EZ-2 evaporator to afford the title compound (56 mg, 72%). LCMS calculated for $C_{20}H_{22}N_7O_4S$ (M+H)$^+$: m/z=456.1, found: 456.1.

Step 4. 3-(3-(5-Amino-6-(1H-1,2,4-triazol-1-yl)pyrazin-2-yl)-4-methylphenylsulfonamido)-N-methylbicyclo[1.1.1]pentane-1-carboxamide Trifluoroacetate Salt To a solution of methyl 3-((3-(5-amino-6-(1H-1,2,4-triazol-1-yl)pyrazin-2-yl)-4-methylphenyl)sulfonamido)bicyclo[1.1.1]pentane-1-carboxylate (10 mg, 0.022 mmol) in THF (1.0 ml) was added methylamine (0.11 ml, 0.22 mmol, 2M/THF) and trimethylaluminum (55 µL, 0.11 mmol). The reaction mixture was heated to 80° C. overnight. After cooling to room temperature, MeOH was added and the resulting solution was stirred for 1 h. The reaction mixture was filtered through Celite®, concentrated, and purified by prep HPLC (pH 2) to afford the title compound. LCMS calculated for $C_{20}H_{23}N_8O_3S$ (M+H)$^+$: m/z=455.2, found: 455.1.

Examples 33-35

Unless otherwise indicted, the compounds of Examples 33-35 in Table 5 were synthesized according to the procedure described for Example 32, Step 4 utilizing the appropriate amines.

TABLE 5

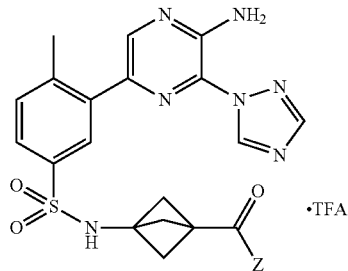

| Example No. | Compound Name | Z | LCMS |
|---|---|---|---|
| 33 | 3-(3-(5-Amino-6-(1H-1,2,4-triazol-1-yl)pyrazin-2-yl)-4-methylphenylsulfonamido)-N,N-dimethylbicyclo[1.1.1]pentane-1-carboxamide trifluoroacetate salt | 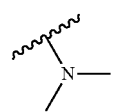 | Calculated for $C_{21}H_{25}N_8O_3S$ (M + H)$^+$: m/z = 469.2, found: 469.2 |

TABLE 5-continued

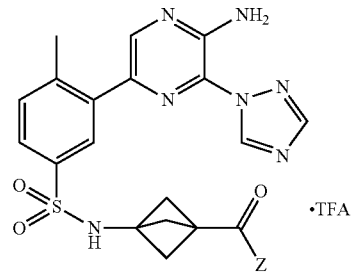

| Example No. | Compound Name | Z | LCMS |
|---|---|---|---|
| 34 | 3-(5-Amino-6-(1H-1,2,4-triazol-1-yl)pyrazin-2-yl)-N-(3-(azetidine-1-carbonyl)bicyclo[1.1.1]pentan-1-yl)-4-methylbenzenesulfonamide trifluoroacetate salt | 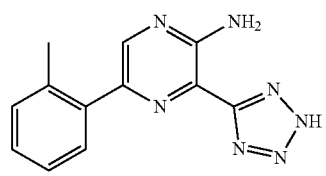 | Calculated for $C_{22}H_{25}N_8O_3S$ $(M + H)^+$: m/z = 481.2, found: 481.2 |
| 35 | 3-(3-(5-Amino-6-(1H-1,2,4-triazol-1-yl)pyrazin-2-yl)-4-methylphenylsulfonamido)-N-(2,2,2-trifluoroethyl)bicyclo[1.1.1]pentane-1-carboxamide trifluoroacetate salt | 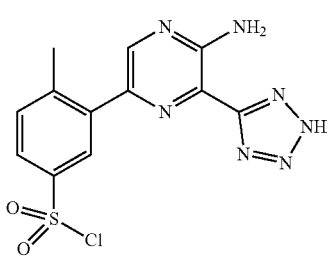 | Calculated for $C_{21}H_{22}F_3N_8O_3S$ $(M + H)^+$: m/z = 523.1, found: 523.1 |

Example 36. 3-(5-Amino-6-(2H-tetrazol-5-yl)pyrazin-2-yl)-N-(3-cyanobicyclo[1.1.1]pentan-1-yl)-4-methylbenzenesulfonamide Trifluoroacetate Salt

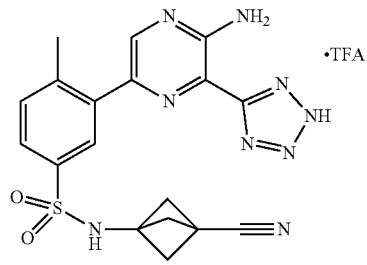 [SMILES: Cc1ccc(S(=O)(=O)NC23CC(C#N)(C2)C3)cc1-c1cnc(N)c(-c2nn[nH]n2)n1]

Step 1. 3-Amino-6-o-tolylpyrazine-2-carbonitrile

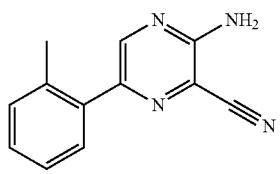 [SMILES: Cc1ccccc1-c1cnc(N)c(C#N)n1]

This compound was synthesized by a procedure analogous to that of Example 23, Step 2, utilizing 3-amino-6-bromopyrazine-2-carbonitrile (Ark Pharm) instead of 5-bromo-3-(1H-1,2,4-triazol-1-yl)pyrazin-2-amine. LCMS calculated for $C_{12}H_{11}N_4$ (M+H)$^+$: m/z=211.1, found: 211.1.

Step 2. 3-(2H-Tetrazol-5-yl)-5-o-tolylpyrazin-2-amine

A mixture of 3-amino-6-(o-tolyl)pyrazine-2-carbonitrile (150 mg, 0.71 mmol) and sodium azide (232 mg, 3.57 mmol) in NMP (4.0 ml) was heated to 130° C. for 3 h. After cooling to room temperature, the reaction mixture was partitioned between water and EtOAc, and the layers were separated. The aqueous layer was acidified with 1M HCl to pH 2. The resulting precipitate was filtered, washed with water, and air dried to yield the title compound (123 mg, 68%). LCMS calculated for $C_{12}H_{12}N_7$ (M+H)$^+$: m/z=254.1, found: 254.2.

Step 3. 3-(5-Amino-6-(2H-tetrazol-5-yl)pyrazin-2-yl)-4-methylbenzene-1-sulfonyl chloride This compound was synthesized by a procedure analogous to that described for Example 23, Step 3, utilizing 3-(2H-tetrazol-5-yl)-5-o-tolylpyrazin-2-amine instead of 5-(o-tolyl)-3-(1H-1,2,4-triazol-1-yl)pyrazin-2-amine. LCMS calculated for $C_{12}H_{11}ClN_7O_2S$ (M+H)$^+$: m/z=352.0, found: 352.0.

Step 4. 3-(5-Amino-6-(2H-tetrazol-5-yl)pyrazin-2-yl)-N-(3-cyanobicyclo[1.1.1]pentan-1-yl)-4-methylbenzenesulfonamide Trifluoroacetate Salt This compound was synthesized by a procedure analogous to that described for Example 1, Step 4, utilizing 3-(5-amino-6-(2H-tetrazol-5-yl)pyrazin-2-yl)-4-methylbenzene-1-sulfonyl chloride instead of 3-(5-amino-6-(2-methylthiazol-5-yl)pyrazin-2-yl)-4-methylbenzenesulfonyl chloride. $^1$H NMR (400 MHz, DMSO) δ 8.92 (s, 1H), 8.48 (s, 1H), 7.87 (d, J=1.9 Hz, 1H), 7.77 (dd, J=8.0, 2.0 Hz, 1H), 7.59 (d, J=8.1 Hz, 1H), 2.50 (s, 3H), 2.25 (s, 6H). LCMS calculated for $C_{18}H_{18}N_9O_2S$ (M+H)$^+$: m/z=424.1, found: 424.0.

Example 37. 3-(5-Amino-6-(2H-tetrazol-5-yl)pyrazin-2-yl)-N-(4-cyanobicyclo[2.1.1]hexan-1-yl)-4-methylbenzenesulfonamide Trifluoroacetate Salt

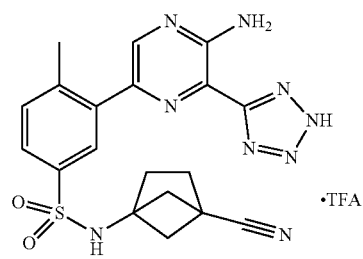 [SMILES: Cc1ccc(S(=O)(=O)NC23CCC(C#N)(C2)C3)cc1-c1cnc(N)c(-c2nn[nH]n2)n1]

This compound was synthesized by a procedure analogous to that described for Example 1, Step 4, utilizing 3-(5-amino-6-(2H-tetrazol-5-yl)pyrazin-2-yl)-4-methylbenzene-1-sulfonyl chloride and 4-aminobicyclo[2.1.1]hexane-1-carbonitrile hydrochloride. $^1$H NMR (400 MHz, DMSO) δ 8.67 (s, 1H), 8.48 (s, 1H), 7.91 (d, J=1.9 Hz, 1H), 7.79 (dd, J=8.0, 2.0 Hz, 1H), 7.58 (d, J=8.1 Hz, 1H), 2.49 (s, 3H), 1.97 (brs, 2H), 1.93-1.84 (m, 2H), 1.73-1.65 (m, 2H), 1.59 (dd, J=3.9, 1.8 Hz, 2H). LCMS calculated for $C_{19}H_{20}N_9O_2S$ (M+H)$^+$: m/z=438.1, found: 438.0.

Example 39. Ethyl 3-(3-(5-amino-6-(1H-1,2,4-triazol-1-yl)pyrazin-2-yl)-4-methylphenylsulfonamido)bicyclo[1.1.1]pentan-1-ylcarbamate Trifluoroacetate Salt

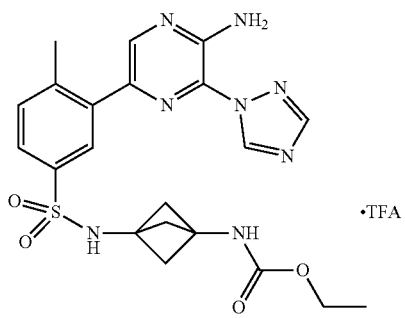 [SMILES: CCOC(=O)NC12CC(NS(=O)(=O)c3ccc(C)c(-c4cnc(N)c(-n5cncn5)n4)c3)(C1)C2]

Step 1. Ethyl 3-aminobicyclo[1.1.1]pentan-1-ylcarbamate Hydrochloride

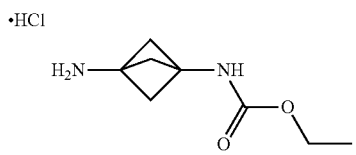

A mixture of tert-butyl (3-aminobicyclo[1.1.1]pentan-1-yl)carbamate (15 mg, 0.076 mmol) in DCM (2 ml) was treated with triethylamine (53 μL, 0.38 mmol) and cooled to 0° C. To the reaction was added ethyl chloroformate (22 μL, 0.23 mmol). The reaction mixture was allowed to warm to room temperature and stir for 2 h. Water and DCM were added, and the layers were separated. The organic layer was washed with brine, dried over MgSO$_4$, filtered and concentrated. The residue was stirred in HCl (4.0 M in dioxane) (2.0 ml, 8.0 mmol) for 1 h, and the volatiles were evaporated. The residue was used without purification. LCMS calculated for $C_8H_{15}N_2O_2$ (M+H)$^+$: m/z=171.1, found: 171.1.

Step 2. Ethyl 3-(3-(5-amino-6-(1H-1,2,4-triazol-1-yl)pyrazin-2-yl)-4-methylphenylsulfonamido)bicyclo[1.1.1]pentan-1-ylcarbamate Trifluoroacetate Salt To a solution of ethyl (3-aminobicyclo[1.1.1]pentan-1-yl)carbamate hydrochloride (8.8 mg, 0.043 mmol) and DIPEA (15 μL, 0.086 mmol) in DCM (2.0 ml) at 0° C. was added a solution of 3-(5-amino-6-(1H-1,2,4-triazol-1-yl)pyrazin-2-yl)-4-methylbenzenesulfonyl chloride (10 mg, 0.029 mmol, from Example 23, Step 3) in DMA (0.5 mL) dropwise. The 0° C. bath was removed, and the reaction mixture was stirred at room temperature for 1 h. The reaction mixture was concentrated to remove DCM, diluted with MeOH, and purified by prep HPLC (pH 2) to afford the title compound. LCMS calculated for $C_{21}H_{25}N_8O_4S$ (M+H)$^+$: m/z=485.2, found: 485.1.

Example 40. N-(3-(3-(5-Amino-6-(1H-1,2,4-triazol-1-yl)pyrazin-2-yl)-4-methylphenylsulfonamido)bicyclo[1.1.1]pentan-1-yl)acetamide Trifluoroacetate Salt

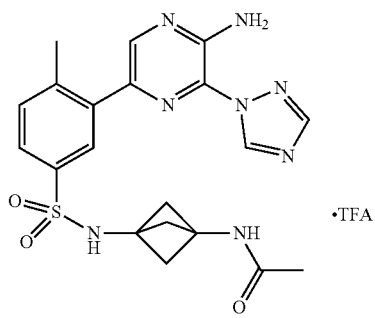 [SMILES: CC(=O)NC12CC(NS(=O)(=O)c3ccc(C)c(-c4cnc(N)c(-n5cncn5)n4)c3)(C1)C2]

Step 1. N-(3-Aminobicyclo[1.1.1]pentan-1-yl)acetamide Hydrochloride

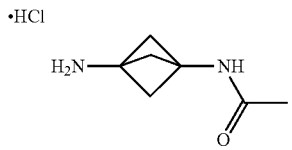

This compound was synthesized by a procedure analogous to that described for Example 39, Step 1, utilizing acetyl chloride instead of ethyl chloroformate. LCMS (Boc protected intermediate) calculated for $C_{12}H_{21}N_2O_3$ (M+H)$^+$: m/z=241.1, found: 241.1.

Step 2. N-(3-(3-(5-Amino-6-(1H-1,2,4-triazol-1-yl)pyrazin-2-yl)-4-methylphenylsulfonamido)bicyclo[1.1.1]pentan-1-yl)acetamide This compound was synthesized by a procedure analogous to that described for Example 39, Step 2, utilizing A-(3-aminobicyclo[1.1.1]pentan-1-yl)acetamide hydrochloride instead of ethyl (3-aminobicyclo[1.1.1]pentan-1-yl)carbamate hydrochloride. LCMS calculated for $C_{20}H_{23}N_8O_3S$ (M+H)$^+$: m/z=455.2, found: 455.1.

Example 41. 3-(5-Amino-6-(2H-1,2,3-triazol-2-yl)pyrazin-2-yl)-N-(3-cyanobicyclo[1.1.1]pentan-1-yl)-4-methylbenzenesulfonamide Trifluoroacetate Salt

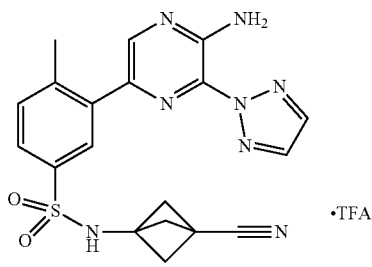 [SMILES: Cc1ccc(S(=O)(=O)NC23CC(C#N)(C2)C3)cc1-c1cnc(N)c(-n2nccn2)n1]

Step 1. 5-Bromo-3-(2H-1,2,3-triazol-2-yl)pyrazin-2-amine

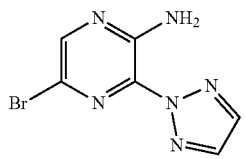 [SMILES: Nc1ncc(Br)nc1-n1nccn1]

A mixture of 5-bromo-3-chloropyrazin-2-amine (600 mg, 2.88 mmol), 1H-1,2,3-triazole (0.33 ml, 5.76 mmol), and cesium carbonate (1.88 g, 5.76 mmol) in NMP (10.0 ml) was heated to 130° C. for 2 h. After cooling to room temperature, the reaction mixture was partitioned between water and EtOAc, and the layers were separated. The aqueous layer was extracted with EtOAc and the combined organic layers were washed with brine, dried over MgSO$_4$, filtered, and concentrated. The product was obtained as a 1:1 mixture with the corresponding 1H-isomer. Complete separation of the isomers was achieved by purification on prep HPLC (pH 2) to afford the title compound. Fractions containing the desired product (peak #1 from HPLC) were combined, basified with saturated NaHCO$_3$, and extracted with DCM. The organic extract was dried over MgSO$_4$, filtered, and concentrated to afford the title compound (190 mg, 27%). $^1$H NMR (400 MHz, DMSO) δ 8.32 (s, 1H), 8.26 (s, 2H), 7.40 (br s, 2H). LCMS calculated for $C_6H_6BrN_6$ (M+H)$^+$: m/z=241.0, found: 240.9.

Step 2. 5-o-Tolyl-3-(2H-1,2,3-triazol-2-yl)pyrazin-2-amine

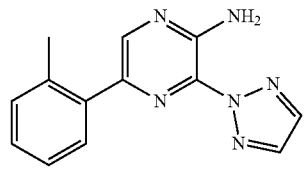 [SMILES: Cc1ccccc1-c1cnc(N)c(-n2nccn2)n1]

This compound was synthesized by a procedure analogous to that described for Example 23, Step 2, utilizing 5-bromo-3-(2H-1,2,3-triazol-2-yl)pyrazin-2-amine instead of 5-bromo-3-(1H-1,2,4-triazol-1-yl)pyrazin-2-amine. LCMS calculated for $C_{13}H_{13}N_6$ (M+H)$^+$: m/z=253.1, found: 253.2.

Step 3. 3-(5-Amino-6-(2H-1,2,3-triazol-2-yl)pyrazin-2-yl)-4-methylbenzene-1-sulfonyl Chloride

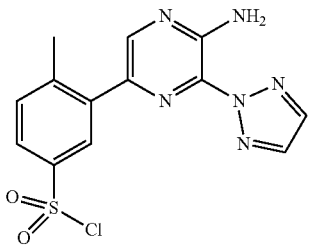 [SMILES: Cc1ccc(S(=O)(=O)Cl)cc1-c1cnc(N)c(-n2nccn2)n1]

This compound was synthesized by a procedure analogous to that described for Example 23, Step 3, utilizing 5-o-tolyl-3-(2H-1,2,3-triazol-2-yl)pyrazin-2-amine instead of 5-(o-tolyl)-3-(1H-1,2,4-triazol-1-yl)pyrazin-2-amine. LCMS calculated for $C_{13}H_{12}ClN_6O_2S$ (M+H)$^+$: m/z=351.0, found: 351.0.

Step 4. 3-(5-Amino-6-(2H-1,2,3-triazol-2-yl)pyrazin-2-yl)-N-(3-cyanobicyclo[1.1.1]pentan-1-yl)-4-methylbenzenesulfonamide Trifluoroacetate Salt This compound was synthesized by a procedure analogous to that described for Example 1, Step 4. $^1$H NMR (400 MHz, DMSO) δ 8.92 (s, 1H), 8.44 (s, 1H), 8.25 (s, 2H), 7.91 (d, J=2.0 Hz, 1H), 7.74 (dd, J=8.0, 2.1 Hz, 1H), 7.56 (d, J=8.1 Hz, 1H), 2.53 (s, 3H), 2.27 (s, 6H). LCMS calculated for $C_{19}H_{19}N_8O_2S$ (M+H)$^+$: m/z=423.1, found: 423.1.

Example 42. 3-(5-Amino-6-(2H-1,2,3-triazol-2-yl)pyrazin-2-yl)-N-(4-cyanobicyclo[2.1.1]hexan-1-yl)-4-methylbenzenesulfonamide Trifluoroacetate Salt

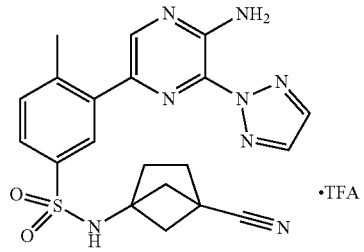 [SMILES: Cc1ccc(S(=O)(=O)NC23CCC(C#N)(C2)C3)cc1-c1cnc(N)c(-n2nccn2)n1]

This compound was synthesized by a procedure analogous to that described for Example 41 utilizing 4-aminobicyclo[2.1.1]hexane-1-carbonitrile hydrochloride instead of 3-aminobicyclo[1.1.1]pentane-1-carbonitrile hydrochloride in Step 4. $^1$H NMR (500 MHz, DMSO) δ 8.68 (s, 1H), 8.43 (s, 1H), 8.25 (s, 2H), 7.94 (d, J=2.0 Hz, 1H), 7.76 (dd, J=8.0, 2.1 Hz, 1H), 7.55 (d, J=8.1 Hz, 1H), 2.52 (s, 3H), 1.99-1.94 (m, 2H), 1.91-1.84 (m, 2H), 1.74-1.67 (m, 2H), 1.61 (dd, J=4.0, 1.9 Hz, 2H). LCMS calculated for $C_{20}H_{21}N_8O_2S$ (M+H)$^+$: m/z=437.1, found: 437.1.

Example 43. 3-(5-Amino-6-(1H-1,2,3-triazol-1-yl)pyrazin-2-yl)-N-(3-cyanobicyclo[1.1.1]pentan-1-yl)-4-methylbenzenesulfonamide Trifluoroacetate Salt

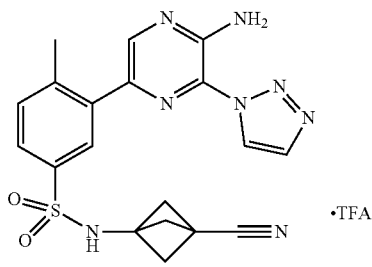 [SMILES: Cc1ccc(S(=O)(=O)NC23CC(C#N)(C2)C3)cc1-c1cnc(N)c(-n2ccnn2)n1]

This compound was synthesized by a procedure analogous to that described for Example 41, utilizing the 1H-isomer (peak #2 from HPLC) obtained in Step 1. LCMS calculated for $C_{19}H_{19}N_8O_2S$ (M+H)$^+$: m/z=423.1, found: 423.1.

Example 44. 3-(5-Amino-6-(1H-1,2,3-triazol-1-yl)pyrazin-2-yl)-N-(4-cyanobicyclo[2.1.1]hexan-1-yl)-4-methylbenzenesulfonamide Trifluoroacetate Salt

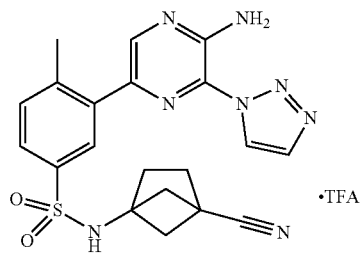 [SMILES: Cc1ccc(S(=O)(=O)NC23CCC(C#N)(C2)C3)cc1-c1cnc(N)c(-n2ccnn2)n1]

This compound was synthesized by a procedure analogous to that described for Example 41, utilizing the 1H-isomer obtained in Step 1. LCMS calculated for $C_{20}H_{21}N_8O_2S$ (M+H)$^+$: m/z=437.1, found: 437.1.

Example 45. 3-(5-Amino-6-(1-methyl-1H-1,2,4-triazol-3-yl)pyrazin-2-yl)-N-(3-cyanobicyclo[1.1.1]pentan-1-yl)-4-methylbenzenesulfonamide Trifluoroacetate Salt

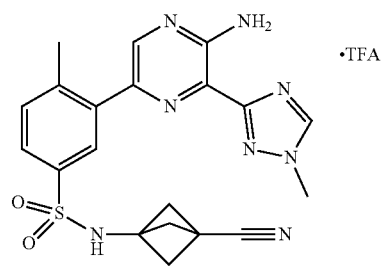 [SMILES: Cc1ccc(S(=O)(=O)NC23CC(C#N)(C2)C3)cc1-c1cnc(N)c(-c2ncn(C)n2)n1]

Step 1. 5-o-Tolyl-3-(4H-1,2,4-triazol-3-yl)pyrazin-2-amine

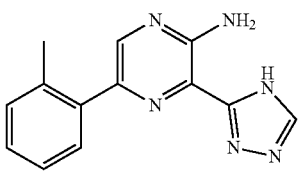 [SMILES: Cc1ccccc1-c1cnc(N)c(-c2nnc[nH]2)n1]

To a solution of 3-amino-6-(o-tolyl)pyrazine-2-carbonitrile (150 mg, 0.71 mmol, Example 36, Step 1) in EtOH (4.0 ml) was added hydrazine (0.19 ml, 3.57 mmol) and the reaction mixture was heated to reflux for 1.5 h, and the volatiles were removed in vacuo. The resulting solid was dissolved in formic acid (1 ml, 26.1 mmol) and heated to 80° C. for 3 h. After cooling to room temperature, the reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-50% EtOAc/hexanes) to afford the title compound (98 mg, 54%). LCMS calculated for $C_{13}H_{13}N_6$ (M+H)$^+$: m/z=253.1 found: 253.1.

Step 2. 3-(1-Methyl-1H-1,2,4-triazol-3-yl)-5-o-tolylpyrazin-2-amine

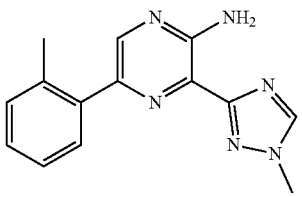 [SMILES: Cc1ccccc1-c1cnc(N)c(-c2ncn(C)n2)n1]

To a solution of 5-(o-tolyl)-3-(4H-1,2,4-triazol-3-yl)pyrazin-2-amine (98 mg, 0.39 mmol) in DMF (3.0 ml) was added potassium carbonate (81 mg, 0.58 mmol), followed by methyl iodide (36 µL, 0.58 mmol), and the reaction mixture was heated to 60° C. for 2 h. After cooling to room temperature, the reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-30% EtOAc/hexanes) to afford the title compound (40 mg, 39%). LCMS calculated for $C_{14}H_{15}N_6$ (M+H)$^+$: m/z=267.1 found: 267.1.

Step 3. 3-(5-Amino-6-(1-methyl-1H-1,2,4-triazol-3-yl)pyrazin-2-yl)-4-methylbenzene-1-sulfonyl Chloride

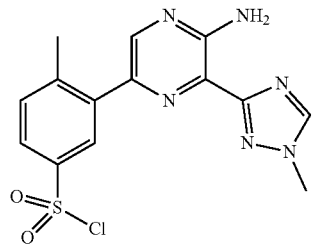 [SMILES: Cc1ccc(S(=O)(=O)Cl)cc1-c1cnc(N)c(-c2ncn(C)n2)n1]

This compound was synthesized by a procedure analogous to that described for Example 23, Step 3, utilizing 3-(1-methyl-1H-1,2,4-triazol-3-yl)-5-o-tolylpyrazin-2-amine instead of 5-(o-tolyl)-3-(1H-1,2,4-triazol-1-yl)pyrazin-2-amine. LCMS calculated for $C_{14}H_{14}ClN_6O_2S$ (M+H)$^+$: m/z=351.0, found: 351.0.

Step 4. 3-(5-Amino-6-(1-methyl-1H-1,2,4-triazol-3-yl)pyrazin-2-yl)-N-(3-cyanobicyclo[1.1.1]pentan-1-yl)-4-methylbenzenesulfonamide Trifluoroacetate Salt This compound was synthesized by a procedure analogous to that described for Example 1, Step 4, utilizing 3-(5-amino-6-(1-methyl-1H-1,2,4-triazol-3-yl)pyrazin-2-yl)-4-methylbenzene-1-sulfonyl chloride instead of 3-(5-amino-6-(2-methylthiazol-5-yl)pyrazin-2-yl)-4-methylbenzenesulfonyl chloride. $^1$H NMR (400 MHz, DMSO) δ 8.93 (s, 1H), 8.41 (s, 1H), 8.20 (s, 1H), 7.91 (d, J=2.0 Hz, 1H), 7.74 (dd, J=8.0, 2.0 Hz, 1H), 7.58 (d, J=8.1 Hz, 1H), 4.26 (s, 3H), 2.50 (s, 3H), 2.24 (s, 6H). LCMS calculated for $C_{20}H_{21}N_8O_2S$ (M+H)$^+$: m/z=437.1, found: 437.1.

Example 46. 3-(5-Amino-6-(1-methyl-1H-1,2,4-triazol-3-yl)pyrazin-2-yl)-N-(4-cyanobicyclo[2.1.1]hexan-1-yl)-4-methylbenzenesulfonamide Trifluoroacetate Salt

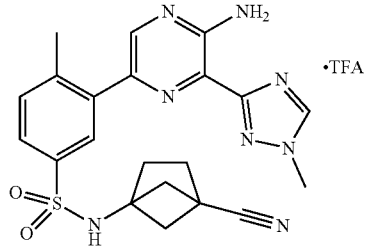 [SMILES: Cc1ccc(S(=O)(=O)NC23CCC(C#N)(C2)C3)cc1-c1cnc(N)c(-c2ncn(C)n2)n1]

This compound was synthesized by a procedure analogous to that described for Example 45 utilizing 4-aminobicyclo[2.1.1]hexane-1-carbonitrile hydrochloride instead of 3-aminobicyclo[1.1.1]pentane-1-carbonitrile hydrochloride in Step 4. $^1$H NMR (600 MHz, DMSO) δ 8.69 (s, 1H), 8.41 (s, 1H), 8.20 (s, 1H), 7.95 (d, J=2.1 Hz, 1H), 7.77 (dd, J=8.0, 2.1 Hz, 1H), 7.57 (d, J=8.1 Hz, 1H), 4.27 (s, 3H), 2.49 (s, 3H), 1.98-1.93 (m, 2H), 1.89-1.86 (m, 2H), 1.71-1.66 (m, 2H), 1.58 (dd, J=4.0, 1.9 Hz, 2H). LCMS calculated for $C_{21}H_{23}N_8O_2S$ (M+H)$^+$: m/z=451.2, found: 451.2.

Example 47. 3-(5-Amino-6-(1H-1,2,4-triazol-1-yl)pyrazin-2-yl)-N-(4-hydroxybicyclo[2.2.1]heptan-1-yl)-4-(methyl-d$_3$)benzenesulfonamide Trifluoroacetate Salt

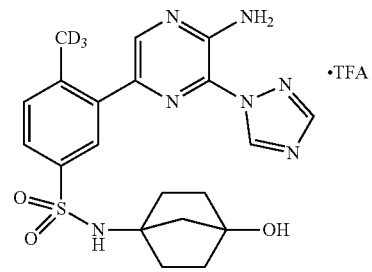 [SMILES: [2H]C([2H])([2H])c1ccc(S(=O)(=O)NC23CCC(O)(CC2)C3)cc1-c1cnc(N)c(-n2cncn2)n1]

Step 1. 3-(5-Amino-6-(1H-1,2,4-triazol-1-yl)pyrazin-2-yl)-4-(methyl-d$_3$)benzenesulfonyl Chloride

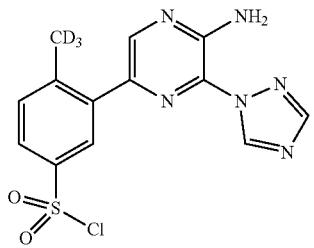

This compound was synthesized by a procedure analogous to that described in Example 23, utilizing 4,4,5,5-tetramethyl-2-(2-(methyl-d$_3$)phenyl)-1,3,2-dioxaborolane instead of o-tolylboronic acid in Step 2. LCMS calculated for $C_{13}H_9D_3ClN_6O_2S$ (M+H)$^+$: m/z=354.1, found: 354.0.

Step 2. 3-(5-Amino-6-(1H-1,2,4-triazol-1-yl)pyrazin-2-yl)-N-(4-hydroxybicyclo[2.1.1]heptan-1-yl)-4-(methyl-d$_3$)benzenesulfonamide Trifluoroacetate Salt To a mixture of 3-(5-amino-6-(1H-1,2,4-triazol-1-yl)pyrazin-2-yl)-4-(methyl-d$_3$)benzenesulfonyl chloride (35 mg, 0.10 mmol) and 4-aminobicyclo[2.2.1]heptan-1-ol hydrochloride (19 mg, 0.11 mmol, Intermediate 9) was added DCM (0.60 ml) and MeCN (0.30 ml), followed by sodium carbonate (1.0 M in H$_2$O) (0.40 ml, 0.40 mmol). The suspension was stirred overnight, at which point the reaction became a clear solution. The reaction mixture was partitioned between water and DCM, and the layers were separated. The aqueous layer was extracted with DCM and the combined organic layers were dried over MgSO$_4$, filtered, and concentrated. The residue was dissolved in MeOH, and was purified by prep HPLC (pH 2) to afford the title compound. $^1$H NMR (600 MHz, DMSO) δ 9.34 (s, 1H), 8.43 (s, 1H), 8.40 (s, 1H), 7.97 (d, J=2.0 Hz, 1H), 7.95 (s, 1H), 7.74 (dd, J=8.0, 2.1 Hz, 1H), 7.53 (d, J=8.0 Hz, 1H), 1.80-1.75 (m, 2H), 1.56-1.47 (m, 4H), 1.45-1.33 (m, 4H). LCMS calculated for C$_{20}$H$_{21}$D$_3$N$_7$O$_3$S (M+H)$^+$: m/z=445.2, found: 445.1.

Example 48. 3-(5-Amino-6-(1H-1,2,4-triazol-1-yl)pyrazin-2-yl)-N-(3-cyanobicyclo[1.1.1]pentan-1-yl)-4-(methyl-d$_3$)benzenesulfonamide Trifluoroacetate Salt

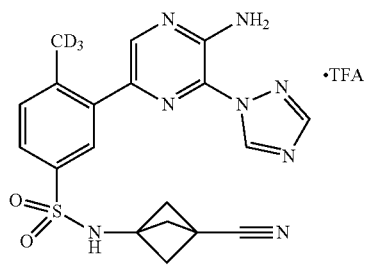

This compound was synthesized by a procedure analogous to that described for Example 47, utilizing 3-aminobicyclo[1.1.1]pentane-1-carbonitrile hydrochloride instead of 4-aminobicyclo[2.2.1]heptan-1-ol hydrochloride in Step 2. $^1$H NMR (600 MHz, DMSO) δ 9.33 (s, 1H), 8.93 (s, 1H), 8.42 (s, 1H), 8.41 (s, 1H), 7.91 (d, J=2.0 Hz, 1H), 7.74 (dd, J=8.0, 2.1 Hz, 1H), 7.57 (d, J=8.0 Hz, 1H), 2.25 (s, 6H). LCMS calculated for C$_{19}$H$_{16}$D$_3$N$_8$O$_2$S (M+H)$^+$: m/z=426.2, found: 426.3.

Example 49. 3-(5-Amino-6-(1H-1,2,4-triazol-1-yl)pyrazin-2-yl)-N-(3-(hydroxymethyl)bicyclo[1.1.1]pentan-1-yl)-4-(methyl-d$_3$)benzenesulfonamide Trifluoroacetate Salt

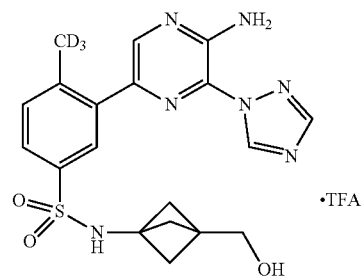 [SMILES: [2H]C([2H])([2H])c1ccc(S(=O)(=O)NC23CC(CO)(C2)C3)cc1-c1cnc(N)c(-n2cncn2)n1]

This compound was synthesized by a procedure analogous to that described for Example 47, utilizing (3-aminobicyclo[1.1.1]pentan-1-yl)methanol hydrochloride instead of 4-aminobicyclo[2.2.1]heptan-1-ol hydrochloride in Step 2. $^1$H NMR (600 MHz, DMSO) δ 9.33 (s, 1H), 8.43 (s, 1H), 8.39 (s, 1H), 7.94 (d, J=2.0 Hz, 1H), 7.73 (dd, J=8.0, 2.1 Hz, 1H), 7.55 (d, J=8.0 Hz, 1H), 3.34 (s, 2H), 1.58 (s, 6H). LCMS calculated for C$_{19}$H$_{19}$D$_3$N$_7$O$_3$S (M+H)$^+$: m/z=431.2, found: 431.2.

Example 50. 3-(5-Amino-6-(2H-1,2,3-triazol-2-yl)pyrazin-2-yl)-N-(3-cyanobicyclo[1.1.1]pentan-1-yl)-4-(methyl-d$_3$)benzenesulfonamide Trifluoroacetate Salt

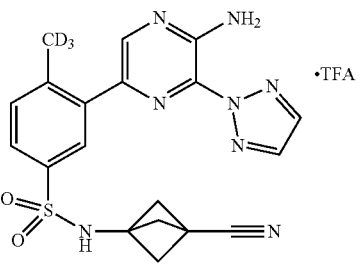 [SMILES: [2H]C([2H])([2H])c1ccc(S(=O)(=O)NC23CC(C#N)(C2)C3)cc1-c1cnc(N)c(-n2nccn2)n1]

Step 1. 3-(5-Amino-6-(2H-1,2,3-triazol-2-yl)pyrazin-2-yl)-4-(methyl-d$_3$)benzenesulfonyl Chloride

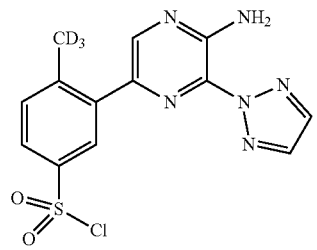 [SMILES: [2H]C([2H])([2H])c1ccc(S(=O)(=O)Cl)cc1-c1cnc(N)c(-n2nccn2)n1]

This compound was synthesized by a procedure analogous to that described in Example 41, utilizing 4,4,5,5-tetramethyl-2-(2-(methyl-d$_3$)phenyl)-1,3,2-dioxaborolane (Intermediate 12) instead of o-tolylboronic acid in Step 2. LCMS calculated for C$_{13}$H$_9$D$_3$ClN$_6$O$_2$S (M+H)$^+$: m/z=354.1, found: 354.0.

Step 2. 3-(5-Amino-6-(2H-1,2,3-triazol-2-yl)pyrazin-2-yl)-N-(3-cyanobicyclo[1.1.1]pentan-1-yl)-4-(methyl-d$_3$)benzenesulfonamide This compound was synthesized by a procedure analogous to that used in Example 47, Step 2. $^1$H NMR (500 MHz, DMSO) δ 8.91 (s, 1H), 8.44 (s, 1H), 8.25 (s, 2H), 7.91 (d, J=2.1 Hz, 1H), 7.74 (dd, J=8.0, 2.1 Hz, 1H), 7.57 (d, J=8.0 Hz, 1H), 2.27 (s, 6H). LCMS calculated for C$_{19}$H$_{16}$D$_3$N$_8$O$_2$S (M+H)$^+$: m/z=426.2, found: 426.1.

Example 51. 3-(5-Amino-6-(2H-1,2,3-triazol-2-yl) pyrazin-2-yl)-N-(3-(hydroxymethyl)bicyclo[1.1.1] pentan-1-yl)-4-(methyl-d₃)benzenesulfonamide Trifluoroacetate Salt

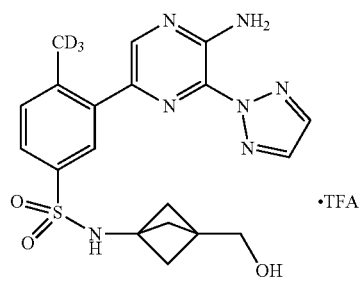 [SMILES: [2H]C([2H])([2H])c1ccc(S(=O)(=O)NC23CC(CO)(C2)C3)cc1-c1cnc(N)c(-n2nccn2)n1]

This compound was synthesized by a procedure analogous to that used for Example 50, utilizing (3-aminobicyclo[1.1.1]pentan-1-yl)methanol hydrochloride instead of 3-aminobicyclo[1.1.1]pentane-1-carbonitrile hydrochloride in Step 2. LCMS calculated for $C_{19}H_{19}D_3N_7O_3S$ $(M+H)^+$: m/z=431.2, found: 431.2.

Example 52. 3-(5-Amino-6-(2H-1,2,3-triazol-2-yl) pyrazin-2-yl)-N-(2-azabicyclo[2.1.1]hexan-4-yl)-4-(methyl-d₃)benzenesulfonamide Trifluoroacetate Salt

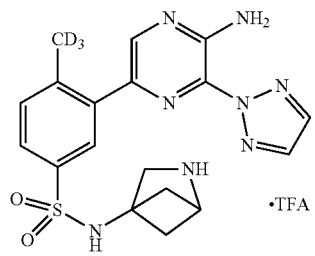 [SMILES: [2H]C([2H])([2H])c1ccc(S(=O)(=O)NC23CNC(C2)C3)cc1-c1cnc(N)c(-n2nccn2)n1]

Step 1. tert-butyl 4-(((benzyloxy)carbonyl)amino)-2-azabicyclo[2.1.1]hexane-2-carboxylate

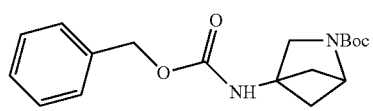 [SMILES: CC(C)(C)OC(=O)N1CC2(NC(=O)OCc3ccccc3)CC1C2]

To a solution of 2-(tert-butoxycarbonyl)-2-azabicyclo[2.1.1]hexane-4-carboxylic acid (190 mg, 0.84 mmol, Pharmablock) in toluene (4 ml) was added triethylamine (0.23 ml, 1.77 mmol), followed by diphenylphosphoryl azide (0.27 ml, 1.33 mmol), and the reaction mixture was heated to reflux for 1 h. The reaction mixture was then cooled to room temperature and benzyl alcohol (0.17 ml, 1.77 mmol) was added. The resulting solution was heated to reflux overnight. After cooling to room temperature, the reaction mixture was concentrated in vacuo and purified by flash chromatography (0-50% EtOAc/hexanes) to afford the product as a colorless oil, which solidified upon standing (210 mg, 76%). LCMS calculated for $C_{18}H_{25}N_2O_4Na$ $(M+Na)^+$: m/z=355.2, found: 355.1.

Step 2. 2-Azabicyclo[2.1.1]hexan-4-amine Dihydrochloride

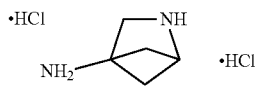

To a solution of tert-butyl 4-(((benzyloxy)carbonyl)amino)-2-azabicyclo[2.1.1]hexane-2-carboxylate (210 mg, 0.63 mmol) in MeOH (4 ml) was added palladium hydroxide on carbon (20 wt %, 44 mg, 0.032 mmol) and the atmosphere of the reaction vial was replaced with hydrogen. The reaction mixture was stirred under 1 atm of hydrogen for 30 min, and was then filtered through a pad of Celite®, which was washed with MeOH. The volatiles were removed in vacuo and the residue was stirred in HCl (4.0 M in dioxane) (3 ml, 12 mmol) for 30 min. The volatiles were removed in vacuo and the resulting white solid was triturated with ether and air dried to afford the title compound (108 mg, quant.). LCMS calculated for $C_5H_{11}N_2$ $(M+H)^+$: m/z=99.1, found: 99.2.

Step 3. 3-(5-Amino-6-(2H-1,2,3-triazol-2-yl) pyrazin-2-yl)-N-(2-azabicyclo[2.1.1]hexan-4-yl)-4-(methyl-d₃)benzenesulfonamide Trifluoroacetate Salt To a mixture of 3-(5-amino-6-(2H-1,2,3-triazol-2-yl) pyrazin-2-yl)-4-(methyl-d₃)benzenesulfonyl chloride (10 mg, 28 µmol) and 2-azabicyclo[2.1.1]hexan-4-amine dihydrochloride (5.8 mg, 34 µmol) was added DCM (0.6 ml) and MeCN (0.3 ml), followed by sodium carbonate (1.0 M in H₂O, 0.11 ml, 0.11 mmol). The suspension was stirred for 3 h, at which point the reaction became a clear solution. The reaction mixture was partitioned between water and DCM, and the layers were separated. The aqueous layer was extracted with DCM and the combined organic layers were washed with brine, dried over MgSO₄, filtered, and concentrated. The residue was dissolved in MeOH was purified by prep HPLC (pH 2) to afford the title compound. LCMS calculated for $C_{18}H_{18}D_3N_8O_2S$ $(M+H)^+$: m/z=416.2, found: 416.1.

Examples 53-59

Unless otherwise indicated, the compounds of Examples 53-59 in Tables 6-7 were synthesized according to the procedure described for Example 52, Step 3, utilizing the appropriate sulfonyl chlorides.

TABLE 6

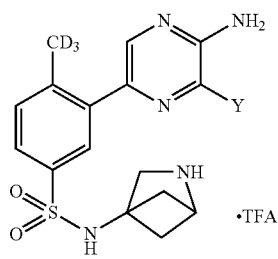

·TFA

| Example No. | Compound Name | R | LCMS |
|---|---|---|---|
| | ¹H NMR | | |
| 53 | 3-(5-Amino-6-(1H-1,2,4-triazol-1-yl)pyrazin-2-yl)-N-(2-azabicyclo[2.1.1]hexan-4-yl)-4-(methyl-d₃)benzenesulfonamide trifluoroacetate salt | triazol-1-yl | Calculated for $C_{18}H_{18}D_3N_8O_2S$ $(M + H)^+$: m/z = 416.2, found: 416.2 |

¹H NMR (400 MHz, DMSO) δ 9.31 (s, 1H), 8.69 (br s, 2H), 8.43 (s, 1H), 8.43 (s, 1H), 8.42 (s, 1H), 7.89 (d, J = 1.9 Hz, 1H), 7.76 (dd, J = 8.0, 1.9 Hz, 1H), 7.64 (d, J = 8.0 Hz, 1H), 7.41 (br s, 1H), 4.35 (s, 1H), 3.30 (s, 2H), 1.94-1.93 (m, 2H), 1.33-1.32 (m, 2H).

| 54 | 3-(5-Amino-6-(2-methylthiazol-5-yl)pyrazin-2-yl)-N-(2-azabicyclo[2.1.1]hexan-4-yl)-4-(methyl-d₃)benzenesulfonamide trifluoroacetate salt | 2-methylthiazol-5-yl | Calculated for $C_{20}H_{20}D_3N_6O_2S_2$ $(M + H)^+$: m/z = 446.1, found: 446.2 |

¹H NMR (500 MHz, DMSO) δ 8.74 (s, 1H), 8.29 (s, 1H), 8.26 (s, 1H), 7.85 (d, J = 2.0 Hz, 1H), 7.74 (dd, J = 8.0, 2.0 Hz, 1H), 7.61 (d, J = 8.0 Hz, 1H), 4.32 (t, J = 1.9 Hz, 1H), 3.29 (s, 2H), 2.69 (s, 3H), 2.00-1.89 (m, 2H), 1.32 (dd, J = 4.7, 1.7 Hz, 2H).

| 55 | 3-(5-Amino-6-(2-cyclopropylthiazol-5-yl)pyrazin-2-yl)-N-(2-azabicyclo[2.1.1]hexan-4-yl)-4-(methyl-d₃)benzenesulfonamide trifluoroacetate salt | 2-cyclopropylthiazol-5-yl | Calculated for $C_{22}H_{22}D_3N_6O_2S_2$ $(M + H)^+$: m/z = 472.2, found: 472.2 |
| 56 | 3-(5-Amino-6-(oxazol-5-yl)pyrazin-2-yl)-N-(2-azabicyclo[2.1.1]hexan-4-yl)-4-(methyl-d₃)benzenesulfonamide trifluoroacetate salt | oxazol-5-yl | Calculated for $C_{19}H_{18}D_3N_6O_3S$ $(M + H)^+$: m/z = 416.2, found: 416.2 |

TABLE 7

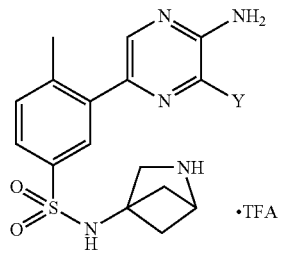

| Example No. | Compound Name | Y | LCMS |
|---|---|---|---|
| 57 | 3-(5-Amino-6-(1-methyl-1H-1,2,4-triazol-3-yl)pyrazin-2-yl)-N-(2-azabicyclo[2.1.1]hexan-4-yl)-4-methylbenzenesulfonamide trifluoroacetate salt | (1-methyl-1,2,4-triazol-3-yl) | Calculated for $C_{19}H_{23}N_8O_2S$ $(M + H)^+$: m/z = 427.2, found: 427.2 |
| 58 | 3-(5-Amino-6-(1H-pyrazol-1-yl)pyrazin-2-yl)-N-(2-azabicyclo[2.1.1]hexan-4-yl)-4-methylbenzenesulfonamide trifluoroacetate salt | (pyrazol-1-yl) | Calculated for $C_{19}H_{22}N_7O_2S$ $(M + H)^+$: m/z = 412.2, found: 412.2 |
| 59 | 3-(5-amino-6-(1H-1,2,3-triazol-1-yl)pyrazin-2-yl)-N-(2-azabicyclo[2.1.1]hexan-4-yl)-4-methylbenzenesulfonamide trifluoroacetate salt | (1,2,3-triazol-1-yl) | Calculated for $C_{18}H_{21}N_8O_2S$ $(M + H)^+$: m/z = 413.1, found: 413.1 |

Example 60. 3-(5-Amino-6-(1H-1,2,4-triazol-1-yl)pyrazin-2-yl)-N-(2-isopropyl-2-azabicyclo[2.1.1]hexan-4-yl)-4-(methyl-d₃)benzenesulfonamide Trifluoroacetate Salt

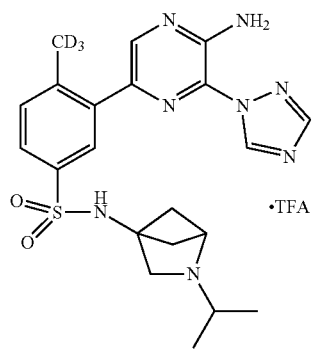 [SMILES: [2H]C([2H])([2H])c1ccc(S(=O)(=O)NC23CC(C2)N(C(C)C)C3)cc1-c1cnc(N)c(-n2cncn2)n1]

To a solution of 3-(5-amino-6-(1H-1,2,4-triazol-1-yl)pyrazin-2-yl)-N-(2-azabicyclo[2.1.1]hexan-4-yl)-4-(methyl-d₃)benzenesulfonamide (10 mg, 0.024 mmol, Example 53) and sodium cyanoborohydride (15 mg, 0.24 mmol) in MeOH (1 ml) was added formaldehyde (37 wt % in water, 36 μL, 0.48 mmol), followed by a few drops of AcOH. The reaction mixture was stirred at room temperature overnight. The reaction was quenched with saturated NaHCO₃ and extracted with EtOAc. The organic layer was washed with brine, dried over MgSO₄, filtered and concentrated. The residue was dissolved in MeOH was purified by prep HPLC (pH 2) to afford the title compound. LCMS calculated for $C_{21}H_{24}D_3N_8O_2S$ $(M+H)^+$: m/z=458.2, found: 458.2.

Example 61. 3-(5-Amino-6-(2-cyclopropylthiazol-5-yl)pyrazin-2-yl)-N-(1-(hydroxymethyl)-2-oxabicyclo[2.1.1]hexan-4-yl)-4-(methyl-d3)benzenesulfonamide Trifluoroacetate Salt

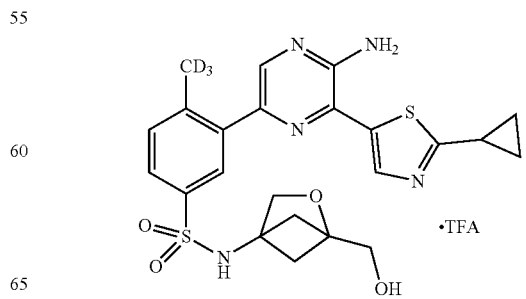

Step 1. 5-Chloro-3-(2-cyclopropylthiazol-5-yl)pyrazin-2-amine

This compound was synthesized by a procedure analogous to that described for Example 1, Step 1, utilizing 2-cyclopropyl-5-(4,4,5,5-tetramethyl-1,3,2-dioxaborolan-2-yl)thiazole instead of 2-methyl-5-(4,4,5,5-tetramethyl-1,3,2-dioxaborolan-2-yl)thiazole. LCMS calculated for $C_{10}H_{10}ClN_4S$ (M+H)$^+$: m/z=253.0, found: 253.0.

Step 2. 3-(2-Cyclopropylthiazol-5-yl)-5-(2-(methyl-d$_3$)phenyl)pyrazin-2-amine

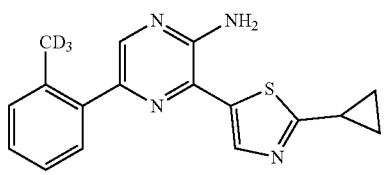 [SMILES: [2H]C([2H])([2H])c1ccccc1-c1cnc(N)c(-c2cnc(C3CC3)s2)n1]

A 40 mL vial was charged with 5-chloro-3-(2-cyclopropylthiazol-5-yl)pyrazin-2-amine (100 mg, 0.40 mmol), 4,4,5,5-tetramethyl-2-(2-(methyl-d$_3$)phenyl)-1,3,2-dioxaborolane (105 mg, 0.48 mmol), bis(di-tert-butyl(4-dimethylaminophenyl)phosphine)dichloropalladium(II) (7 mg, 9.9 µmol), and cesium fluoride (180 mg, 1.19 mmol). Butan-1-ol (3 ml) and water (0.75 ml) were added, and nitrogen was bubbled through the mixture for 5 min, then the reaction was heated to 90° C. for 1 h. The reaction mixture was partitioned between water and EtOAc, and the layers were separated. The aqueous layer was extracted with EtOAc and the combined organic extracts were washed with brine, dried over MgSO$_4$, filtered, and concentrated. The residue was purified by flash chromatography (0-90% EtOAc/hexanes) to afford the desired product as an orange oil (123 mg, quant.). LCMS calculated for $C_{17}H_{14}D_3N_4S$ (M+H)$^+$: m/z=312.1, found: 312.1.

Step 3. 3-(5-Amino-6-(2-cyclopropylthiazol-5-yl)pyrazin-2-yl)-4-(methyl-d$_3$)benzenesulfonyl Chloride

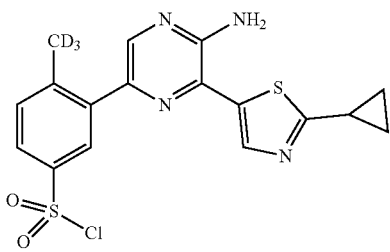 [SMILES: [2H]C([2H])([2H])c1ccc(S(=O)(=O)Cl)cc1-c1cnc(N)c(-c2cnc(C3CC3)s2)n1]

This compound was synthesized by a procedure analogous to that described for Example 1, Step 3, utilizing 3-(2-cyclopropylthiazol-5-yl)-5-(2-(methyl-d$_3$)phenyl)pyrazin-2-amine instead of 3-(2-methylthiazol-5-yl)-5-(o-tolyl)pyrazin-2-amine. LCMS calculated for $C_{17}H_{13}D_3ClN_4O_2S_2$ (M+H)$^+$: m/z=410.1, found: 410.0.

Step 4. 3-(5-Amino-6-(2-cyclopropylthiazol-5-yl)pyrazin-2-yl)-N-(1-(hydroxymethyl)-2-oxabicyclo[2.1.1]hexan-4-yl)-4-(methyl-d$_3$)benzenesulfonamide Trifluoroacetate Salt To a solution of (4-amino-2-oxabicyclo[2.1.1]hexan-1-yl)methanol (3.8 mg, 0.029 mmol) and DIPEA (13 µL, 0.073 mmol) in DCM (3.0 ml) at 0° C. was added a solution of 3-(5-amino-6-(2-cyclopropylthiazol-5-yl)pyrazin-2-yl)-4-(methyl-d$_3$)benzenesulfonyl chloride (10 mg, 0.024 mmol) in DMA (0.5 mL) dropwise. The 0° C. bath was removed, and the reaction mixture was stirred at room temperature for 1 h. The reaction mixture was concentrated, diluted with MeOH, and purified by prep HPLC (pH 2) to afford the title compound. LCMS calculated for $C_{23}H_{23}D_3N_5O_4S_2$ (M+H)$^+$: m/z=503.2, found: 503.2.

Example 62. 3-(5-Amino-6-(1H-pyrazol-1-yl)pyrazin-2-yl)-N-(4-cyanobicyclo[2.1.1]hexan-1-yl)-4-methylbenzenesulfonamide Trifluoroacetate Salt

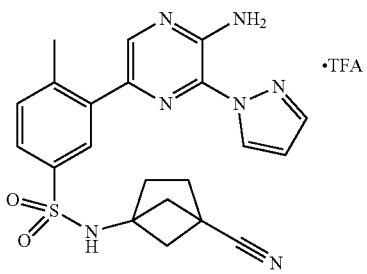 [SMILES: Cc1ccc(S(=O)(=O)NC23CCC(C#N)(C2)C3)cc1-c1cnc(N)c(-n2cccn2)n1]

Step 1. 5-Bromo-3-(1H-pyrazol-1-yl)pyrazin-2-amine

A mixture of 5-bromo-3-chloropyrazin-2-amine (150 mg, 0.72 mmol), 1H-pyrazole (49 mg, 0.72 mmol), and cesium carbonate (352 mg, 1.08 mmol) was taken up in NMP (3.0 ml) and heated to 130° C. for 3 h. After cooling to room temperature, the reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-50% EtOAc/hexanes) to afford the title compound (80 mg, 46%). LCMS calculated for $C_7H_7BrN_5$ (M+H)$^+$: m/z=240.0, found: 240.0.

Step 2. 3-(1H-Pyrazol-1-yl)-5-o-tolylpyrazin-2-amine

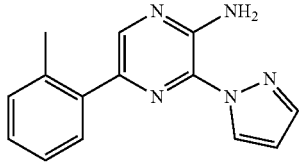 [SMILES: Cc1ccccc1-c1cnc(N)c(-n2cccn2)n1]

This compound was synthesized by a procedure analogous to that described for Example 23, Step 2, utilizing 5-bromo-3-(1H-pyrazol-1-yl)pyrazin-2-amine instead of 5-bromo-3-(1H-1,2,4-triazol-1-yl)pyrazin-2-amine. LCMS calculated for $C_{14}H_{14}N_5$ (M+H)$^+$: m/z=252.1, found: 252.1.

Step 3. 3-(5-Amino-6-(1H-pyrazol-1-yl)pyrazin-2-yl)-4-methylbenzene-1-sulfonyl chloride

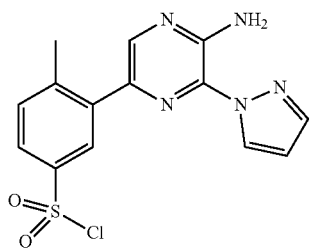 [SMILES: Cc1ccc(S(=O)(=O)Cl)cc1-c1cnc(N)c(-n2cccn2)n1]

This compound was synthesized by a procedure analogous to that described for Example 23, Step 3, utilizing 3-(1H-pyrazol-1-yl)-5-o-tolylpyrazin-2-amine instead of 5-(o-tolyl)-3-(1H-1,2,4-triazol-1-yl)pyrazin-2-amine. LCMS calculated for $C_{14}H_{13}ClN_5O_2S$ (M+H)$^+$: m/z=350.0, found: 350.0.

Step 4. 3-(5-Amino-6-(1H-pyrazol-1-yl)pyrazin-2-yl)-N-(4-cyanobicyclo[2.1.1]hexan-1-yl)-4-methyl-benzenesulfonamide Trifluoroacetate Salt To a solution of 4-aminobicyclo[2.1.1]hexane-1-carbonitrile hydrochloride (6.8 mg, 0.043 mmol) and DIPEA (15 µL, 0.086 mmol) in DCM (2.0 ml) at 0° C. was added a solution of 3-(5-amino-6-(1H-pyrazol-1-yl)pyrazin-2-yl)-4-methylbenzenesulfonyl chloride (10 mg, 0.029 mmol) in DMA (0.5 mL) dropwise. The 0° C. bath was removed, and the reaction mixture was stirred at room temperature for 1 h. The reaction mixture was concentrated to remove DCM, diluted with MeOH, and purified by prep HPLC (pH 2) to afford the title compound. $^1$H NMR (500 MHz, DMSO) δ 8.69 (s, 1H), 8.65 (dd, J=2.6, 0.6 Hz, 1H), 8.27 (s, 1H), 7.97-7.92 (m, 2H), 7.75 (dd, J=8.0, 2.1 Hz, 1H), 7.55 (d, J=8.1 Hz, 1H), 6.67 (dd, J=2.6, 1.8 Hz, 1H), 2.53 (s, 3H), 2.00-1.95 (m, 2H), 1.91-1.84 (m, 2H), 1.73-1.67 (m, 2H), 1.59 (dd, J=4.0, 1.9 Hz, 2H). LCMS calculated for $C_{21}H_{22}N_7O_2S$ (M+H)$^+$: m/z=436.2, found: 436.1.

Example 63. 3-(5-Amino-6-(1-methyl-1H-pyrazol-3-yl)pyrazin-2-yl)-N-(4-cyanobicyclo[2.1.1]hexan-1-yl)-4-(methyl-d$_3$)benzenesulfonamide Trifluoroacetate Salt

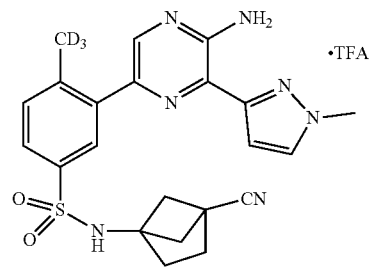 [SMILES: [2H]C([2H])([2H])c1ccc(S(=O)(=O)NC23CCC(C#N)(C2)C3)cc1-c1cnc(N)c(-c2ccn(C)n2)n1]

Step 1. 3-Chloro-5-(2-(methyl-d$_3$)phenyl)pyrazin-2-amine

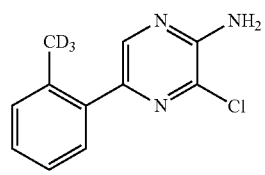 [SMILES: [2H]C([2H])([2H])c1ccccc1-c1cnc(N)c(Cl)n1]

A degassed mixture of 5-bromo-3-chloropyrazin-2-amine (0.306 g, 1.47 mmol, Ark Pharm), 4,4,5,5-tetramethyl-2-(2-(methyl-d$_3$)phenyl)-1,3,2-dioxaborolane (0.250 g, 1.13 mmol, Intermediate 12), bis(di-tert-butyl(4-dimethylaminophenyl)phosphine) dichloropalladium(II) (0.040 g, 0.057 mmol), and CsF (515 mg, 3.39 mmol) in butan-1-ol (6 mL) and H$_2$O (1.6 mL) was heated to 60° C. for 1 hour. The reaction mixture was partitioned between water and EtOAc, and the layers were separated. The aqueous layer was extracted with EtOAc and the combined organic extracts were washed with brine, dried over MgSO$_4$, filtered, and concentrated. The product was purified by flash chromatography, eluting with a gradient of 0-20% EtOAc/hexanes to afford product as a yellow solid (120 mg, 49%). LCMS calculated for $C_{11}H_8D_3ClN_3$ (M+H)$^+$: 223.1, found 223.2.

Step 2. 3-(5-Amino-6-chloropyrazin-2-yl)-4-(methyl-d$_3$)benzenesulfonyl Chloride

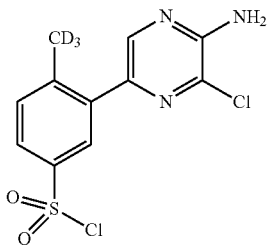 [SMILES: [2H]C([2H])([2H])c1ccc(S(=O)(=O)Cl)cc1-c1cnc(N)c(Cl)n1]

Chlorosulfonic acid (0.36 mL, 5.4 mmol) was added slowly dropwise to a mixture of 3-chloro-5-(2-(methyl-d$_3$)phenyl)pyrazin-2-amine (120 mg, 0.54 mmol) in DCM (4.0 mL) at 0° C. The ice bath was removed and the reaction mixture was stirred at room temperature for 2 hours. The reaction was then heated to 50° C. for 2 hours. The reaction mixture was cooled to room temperature, diluted with DCM, and the solution was added to stirred ice water. After the ice melted, the mixture was extracted twice with DCM and the combined organic extracts were dried over MgSO$_4$, filtered and concentrated to afford product as a light yellow solid (150 mg, 87%). LCMS calculated for C$_{11}$H$_7$D$_3$Cl$_2$N$_3$O$_2$S (M+H)$^+$: 321.0, found 321.0.

Step 3. 3-(5-Amino-6-chloropyrazin-2-yl)-N-(4-cyanobicyclo[2.1.1]hexan-1-yl)-4-(methyl-d3)benzenesulfonamide

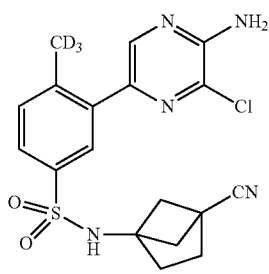 [SMILES: [2H]C([2H])([2H])c1ccc(S(=O)(=O)NC23CCC(C#N)(C2)C3)cc1-c1cnc(N)c(Cl)n1]

4-Aminobicyclo[2.1.1]hexane-1-carbonitrile, HCl salt (0.056 g, 0.36 mmol, Intermediate 4) was stirred in DCM (2.5 mL), CH$_3$CN (1.0 mL) and Na$_2$CO$_3$ (1.0 M, 1.4 mL, 1.4 mmol) for 5 minutes, and then 3-(5-amino-6-chloropyrazin-2-yl)-4-(methyl-d$_3$)benzenesulfonyl chloride (0.114 g, 0.355 mmol) was added. After stirring overnight, the reaction mixture was diluted with water and extracted with EtOAc. The combined organic extracts were dried over Na$_2$SO$_4$, filtered and concentrated. The product was purified by flash chromatography, eluting with a gradient of 0-25% EtOAc in hexanes to afford product as a light yellow solid (0.12 g, 86%). LCMS calculated for C$_{18}$H$_{16}$D$_3$ClN$_5$O$_2$S (M+H)$^+$: 407.1, found 407.2.

Step 4. 3-(5-Amino-6-(1-methyl-1H-pyrazol-3-yl)pyrazin-2-yl)-N-(4-cyanobicyclo[2.1.1]hexan-1-yl)-4-(methyl-d$_3$)benzenesulfonamide Trifluoroacetate Salt To a mixture of 3-(5-amino-6-chloropyrazin-2-yl)-N-(4-cyanobicyclo[2.1.1]hexan-1-yl)-4-(methyl-d$_3$)benzenesulfonamide (12.0 mg, 0.029 mmol) and 1-methyl-3-(4,4,5,5-tetramethyl-1,3,2-dioxaborolan-2-yl)-1H-pyrazole (7.4 mg, 0.035 mmol, WuXi AppTech) in DME (0.6 mL) was added PdCl$_2$(dppf)-CH$_2$Cl$_2$ adduct (2.4 mg, 3.0 µmol) and Na$_2$CO$_3$ solution (1.0 M, 0.088 mL, 0.088 mmol). The mixture was degassed and heated in the microwave reactor to 100° C. for 30 minutes. The product was purified by preparative HPLC-MS (pH 2) to afford product as a light yellow solid (12.9 mg, 77%). LCMS calculated for C$_{22}$H$_{21}$D$_3$N$_7$O$_2$S (M+H)$^+$: m/z=453.2, found: 453.2. $^1$H NMR (400 MHz, DMSO-d$_6$) δ 8.67 (s, 1H), 8.20 (s, 1H), 7.92 (d, J=2.0 Hz, 1H), 7.87 (d, J=2.3 Hz, 1H), 7.73 (dd, J=8.0, 2.1 Hz, 1H), 7.53 (d, J=8.0 Hz, 1H), 6.92 (d, J=2.3 Hz, 1H), 4.00 (s, 3H), 2.02-1.93 (m, 2H), 1.92-1.83 (m, 2H), 1.74-1.65 (m, 2H), 1.63-1.55 (m, 2H).

Examples 64-72

Unless otherwise indicated, the compounds of Examples 64-72 in Table 8 were synthesized according to the procedure described for Example 63, utilizing the appropriate boronic acids, boronic esters or organostannanes in Step 4.

TABLE 8

| Example No. | Compound Name<br>$^1$H NMR | Y | LCMS |
|---|---|---|---|
| 64 | 3-(5-Amino-6-(pyrimidin-5-yl)pyrazin-2-yl)-N-(4-cyanobicyclo[2.1.1]hexan-1-yl)-4-(methyl-d$_3$)benzenesulfonamide trifluoroacetate salt | pyrimidin-5-yl | Calculated for C$_{22}$H$_{19}$D$_3$N$_7$O$_2$S (M + H)$^+$: m/z = 451.2, found: 451.1 |
| | $^1$H NMR (400 MHz, DMSO-d$_6$) δ 9.26 (s, 1H), 9.15 (s, 2H), 8.67 (s, 1H), 8.31 (s, 1H), 7.92 (d, J = 2.0 Hz, 1H), 7.73 (dd, J = 8.0, 2.1 Hz, 1H), 7.53 (d, J = 8.0 Hz, 1H), 6.79 (br s, 2H), 1.99-1.89 (m, 2H), 1.89-1.81 (m, 2H), 1.72-1.64 (m, 2H), 1.61-1.53 (m, 2H). | | |
| 65 | 3-(5-Amino-6-(2-methylthiazol-5-yl)pyrazin-2-yl)-N-(4-cyanobicyclo[2.1.1]hexan-1-yl)-4-(methyl-d$_3$)benzenesulfonamide trifluoroacetate salt | 2-methylthiazol-5-yl | Calculated for C$_{22}$H$_{20}$D$_3$N$_6$O$_2$S$_2$ (M + H)$^+$: m/z = 470.1, found: 470.2 |

TABLE 8-continued

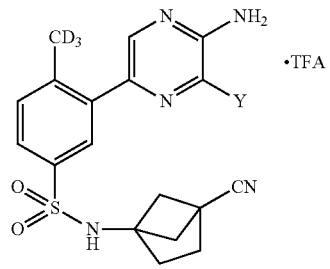

| Example No. | Compound Name | Y | LCMS |
|---|---|---|---|
| | ¹H NMR | | |

¹H NMR (400 MHz, DMSO-d₆) δ 8.66 (s, 1H), 8.29 (s, 1H), 8.24 (s, 1H), 7.89 (d, J = 1.9 Hz, 1H), 7.74 (dd, J = 8.0, 2.1 Hz, 1H), 7.54 (d, J = 8.0 Hz, 1H), 6.75 (br s, 2H), 2.68 (s, 3H), 2.03-1.93 (m, 2H), 1.93-1.83 (m, 2H), 1.74-1.65 (m, 2H), 1.65-1.51 (m, 2H).

| 66 | 3-(5-Amino-6-(2-methyloxazol-5-yl)pyrazin-2-yl)-N-(4-cyanobicyclo[2.1.1]hexan-1-yl)-4-(methyl-d₃)benzenesulfonamide trifluoroacetate salt | 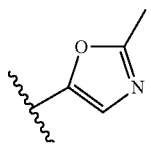 [SMILES: *c1cnc(C)o1] | Calculated for $C_{22}H_{20}D_3N_6O_3S$ (M + H)⁺: m/z = 454.2, found: 454.1 |

¹H NMR (400 MHz, DMSO-d₆) δ 8.67 (s, 1H), 8.25 (s, 1H), 7.88 (d, J = 2.0 Hz, 1H), 7.74 (dd, J = 8.0, 2.1 Hz, 1H), 7.68 (s, 1H), 7.54 (d, J = 8.0 Hz, 1H), 6.74 (br s, 2H), 2.54 (s, 3H), 2.00-1.91 (m, 2H), 1.91-1.78 (m, 2H), 1.75-1.64 (m, 2H), 1.63-1.51 (m, 2H).

| 67 | 3-(5-Amino-6-(2-(dimethylamino)pyrimidin-5-yl)pyrazin-2-yl)-N-(4-cyanobicyclo[2.1.1]hexan-1-yl)-4-(methyl-d₃)benzenesulfonamide trifluoroacetate salt | 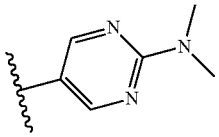 [SMILES: *c1cnc(N(C)C)nc1] | Calculated for $C_{24}H_{24}D_3N_8O_2S$ (M + H)⁺: m/z = 494.2, found: 494.2 |

¹H NMR (400 MHz, DMSO-d₆) δ 8.74 (s, 2H), 8.67 (s, 1H), 8.16 (s, 1H), 7.92 (d, J = 2.0 Hz, 1H), 7.71 (dd, J = 8.0, 2.1 Hz, 1H), 7.52 (d, J = 8.0 Hz, 1H), 3.21 (s, 6H), 2.00-1.90 (m, 2H), 1.90-1.80 (m, 2H), 1.73-1.63 (m, 2H), 1.62-1.53 (m, 2H).

| 69 | 3-(5-Amino-6-(oxazol-5-yl)pyrazin-2-yl)-N-(4-cyanobicyclo[2.1.1]hexan-1-yl)-4-(methyl-d₃)benzenesulfonamide trifluoroacetate salt | 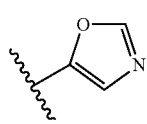 [SMILES: *c1cnco1] | Calculated for $C_{21}H_{18}D_3N_6O_3S$ (M + H)⁺: m/z = 440.2, found: 440.2 |

¹H NMR (400 MHz, DMSO-d₆) δ 8.67 (s, 1H), 8.56 (s, 1H), 8.30 (s, 1H), 7.90 (d, J = 2.0 Hz, 1H), 7.85 (s, 1H), 7.75 (dd, J = 8.0, 2.1 Hz, 1H), 7.54 (d, J = 8.0 Hz, 1H), 6.77 (br s, 2H), 2.02-1.91 (m, 2H), 1.91-1.79 (m, 2H), 1.73-1.64 (m, 2H), 1.64-1.48 (m, 2H).

| 70 | 3-(5-Amino-6-(pyrimidin-2-yl)pyrazin-2-yl)-N-(4-cyanobicyclo[2.1.1]hexan-1-yl)-4-(methyl-d₃)benzenesulfonamide trifluoroacetate salt | 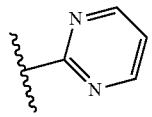 [SMILES: *c1ncccn1] | Calculated for $C_{22}H_{19}D_3N_7O_2S$ (M + H)⁺: m/z = 451.2, found: 451.1 |

¹H NMR (400 MHz, DMSO-d₆) δ 9.02 (d, J = 4.9 Hz, 1H), 8.67 (s, 1H), 8.42 (s, 1H), 7.93 (d, J = 2.0 Hz, 1H), 7.75 (dd, J = 8.0, 2.1 Hz, 1H), 7.57 (t, J = 4.9 Hz, 1H), 7.55 (d, J = 7.9 Hz, 1H), 2.04-1.93 (m, 2H), 1.93-1.80 (m, 2H), 1.74-1.66 (m, 2H), 1.66-1.49 (m, 2H).

| 71 | 3-(5-Amino-6-(oxazol-2-yl)pyrazin-2-yl)-N-(4-cyanobicyclo[2.1.1]hexan-1-yl)-4-(methyl-d₃)benzenesulfonamide trifluoroacetate salt | 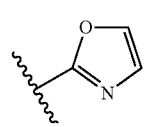 [SMILES: *c1ncco1] | Calculated for $C_{21}H_{18}D_3N_6O_3S$ (M + H)⁺: m/z = 440.2, found: 440.1 |

¹H NMR (400 MHz, CD₃OD) δ 8.32 (s, 1H), 8.11 (s, 1H), 7.99 (d, J = 2.0 Hz, 1H), 7.83 (dd, J = 8.1, 2.1 Hz, 1H), 7.55 (d, J = 8.0 Hz, 1H), 7.48 (s, 1H), 2.14-2.08 (m, 2H), 2.00-1.92 (m, 2H), 1.88-1.78 (m, 2H), 1.71-1.64 (m, 2H).

TABLE 8-continued

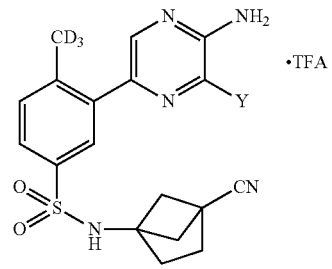

| Example No. | Compound Name ¹H NMR | Y | LCMS |
|---|---|---|---|
| 72 | 3-(5-Amino-6-(pyrimidin-4-yl)pyrazin-2-yl)-N-(4-cyanobicyclo[2.1.1]hexan-1-yl)-4-(methyl-d₃)benzenesulfonamide trifluoroacetate salt | pyrimidin-4-yl | Calculated for $C_{22}H_{19}D_3N_7O_2S$ $(M + H)^+$: m/z = 451.2, found: 451.1 |

¹H NMR (400 MHz, DMSO-$d_6$) δ 9.34 (d, J = 1.2 Hz, 1H), 8.94 (d, J = 5.5 Hz, 1H), 8.70 (s, 1H), 8.51 (s, 1H), 8.42 (dd, J = 5.5, 1.3 Hz, 1H), 7.97 (d, J = 2.0 Hz, 1H), 7.77 (dd, J = 8.0, 2.1 Hz, 1H), 7.58 (d, J = 8.0 Hz, 1H), 2.04-1.92 (m, 2H), 1.92-1.80 (m, 2H), 1.76-1.65 (m, 2H), 1.65-1.52 (m, 2H).

Examples 73-75

Unless otherwise indicated, the compounds of Examples 73-75 in Table 9 were synthesized according to the steps described for Example 63 with the modification that Step 4 (Suzuki coupling using 5-(4,4,5,5-tetramethyl-1,3,2-dioxaborolan-2-yl)oxazole, J&W Pharmlab) was performed before Steps 2 (sulfonyl chloride formation) and 3 (sulfonamide formation), utilizing appropriate amines.

TABLE 9

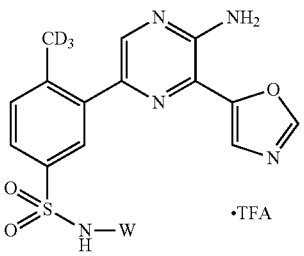

| Example No. | Compound Name ¹H NMR | W | LCMS |
|---|---|---|---|
| 73 | 3-(5-Amino-6-(oxazol-5-yl)pyrazin-2-yl)-N-(3-cyanobicyclo[1.1.1]pentan-1-yl)-4-(methyl-d₃)benzenesulfonamide trifluoroacetate salt | 3-cyanobicyclo[1.1.1]pentan-1-yl | Calculated for $C_{20}H_{16}D_3N_6O_3S$ $(M + H)^+$: m/z = 426.1, found: 426.1 |

¹H NMR (400 MHz, DMSO-$d_6$) δ 8.91 (s, 1H), 8.56 (s, 1H), 8.30 (s, 1H), 7.87 (d, J = 2.0 Hz, 1H), 7.85 (s, 1H), 7.73 (dd, J = 8.0, 2.1 Hz, 1H), 7.56 (d, J = 8.0 Hz, 1H), 6.87 (br s, 2H), 2.26 (s, 6H).

| 74 | 3-(5-Amino-6-(oxazol-5-yl)pyrazin-2-yl)-N-(4-hydroxybicyclo[2.1.1]hexan-1-yl)-4-(methyl-d₃)benzenesulfonamide trifluoroacetate salt | 4-hydroxybicyclo[2.1.1]hexan-1-yl | Calculated for $C_{20}H_{19}D_3N_5O_4S$ $(M + H)^+$: m/z = 431.2, found: 431.1 |

¹H NMR (400 MHz, DMSO-$d_6$) δ 8.57 (s, 1H), 8.27 (s, 1H), 8.23 (s, 1H), 7.89 (d, J = 1.9 Hz, 1H), 7.85 (s, 1H), 7.72 (dd, J = 8.0, 2.0 Hz, 1H), 7.52 (d, J = 8.0 Hz, 1H), 6.77 (br s, 2H), 1.66-1.57 (m, 2H), 1.47-1.38 (m, 4H), 1.36-1.29 (m, 2H).

TABLE 9-continued

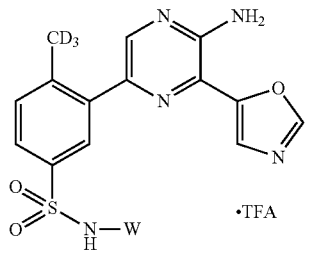

| Example No. | Compound Name<br>¹H NMR | W | LCMS |
|---|---|---|---|
| 75 | 3-(5-Amino-6-(oxazol-5-yl)pyrazin-2-yl)-N-(3-(hydroxymethyl)bicyclo[1.1.1]pentan-1-yl)-4-(methyl-d₃)benzenesulfonamide trifluoroacetate salt | | Calculated for $C_{20}H_{19}D_3N_5O_4S$ $(M + H)^+$: m/z = 431.2, found: 431.1 |

¹H NMR (400 MHz, DMSO-d₆) δ 8.57 (s, 1H), 8.50 (s, 1H), 8.28 (s, 1H), 7.88 (d, J = 1.9 Hz, 1H), 7.84 (s, 1H), 7.72 (dd, J = 8.0, 2.0 Hz, 1H), 7.53 (d, J = 8.0 Hz, 1H), 6.77 (br s, 2H), 3.34 (s, 2H), 1.59 (s, 6H).

Example 76. 3-(5-Amino-6-(2-(methylthio)pyrimidin-4-yl)pyrazin-2-yl)-N-(3-cyanobicyclo[1.1.1]pentan-1-yl)-4-(methyl-d₃)benzenesulfonamide

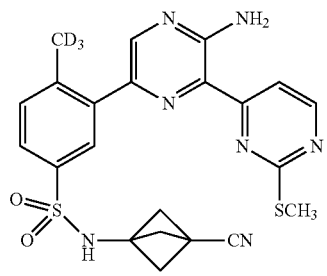 [SMILES: [2H]C([2H])([2H])c1ccc(S(=O)(=O)NC23CC(C#N)(C2)C3)cc1-c1cnc(N)c(-c2ccnc(SC)n2)n1]

Step 1. 5-(2-(Methyl-d₃)phenyl)-3-(2-(methylthio)pyrimidin-4-yl)pyrazin-2-amine

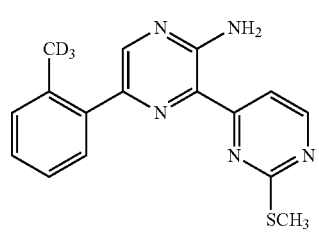 [SMILES: [2H]C([2H])([2H])c1ccccc1-c1cnc(N)c(-c2ccnc(SC)n2)n1]

To a mixture of 3-chloro-5-(2-(methyl-d₃)phenyl)pyrazin-2-amine (0.300 g, 1.35 mmol, from Example 63, Step 1), 2-(methylthio)-4-(tributylstannyl)pyrimidine (839 mg, 2.02 mmol, Frontier) and triethylamine (1.50 mL, 10.78 mmol) in toluene (12 mL) was added tetrakis(triphenylphosphine)palladium(0) (234 mg, 0.202 mmol). The mixture was degassed and heated to 120° C. for 3.5 hours. Solvent was removed in vacuo and the product was purified by flash chromatography, eluting with a gradient of 0-20% EtOAc in hexanes to afford product as a yellow solid (183 mg, 44%). LCMS calculated for $C_{16}H_{13}D_3N_5S$ $(M+H)^+$: m/z=313.1, found: 313.1.

Step 2. 3-(5-Amino-6-(2-(methylthio)pyrimidin-4-yl)pyrazin-2-yl)-N-(3-cyanobicyclo[1.1.1]pentan-1-yl)-4-(methyl-d₃)benzenesulfonamide Using 3-aminobicyclo[1.1.1]pentane-1-carbonitrile trifluoroacetate salt (Intermediate 14) in Step 3, the procedure of Example 63, Steps 2 and 3 were followed to afford the title compound, and the product was purified by preparative HPLC-MS (pH 10) to afford product as the free base. LCMS calculated for $C_{22}H_{19}D_3N_7O_2S_2$ $(M+H)^+$: m/z=483.1, found: 483.1.

Examples 77-78

Unless otherwise indicated, the compounds of Examples 77-78 in Table 10 were synthesized according to the procedure described for Example 76, utilizing the appropriate amines in Step 2.

TABLE 10

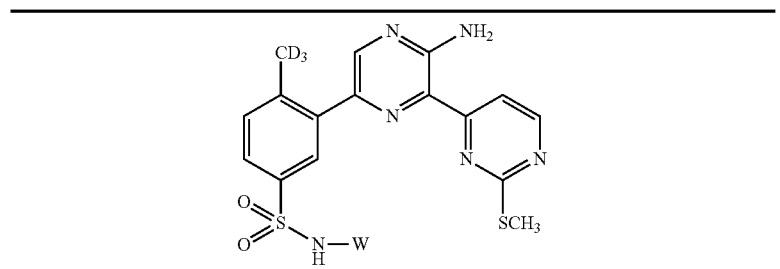

| Example No. | Compound Name | W | LCMS |
|---|---|---|---|
| 77 | 3-(5-Amino-6-(2-(methylthio)pyrimidin-4-yl)pyrazin-2-yl)-N-(4-hydroxybicyclo[2.1.1]hexan-1-yl)-4-(methyl-d₃)benzenesulfonamide | 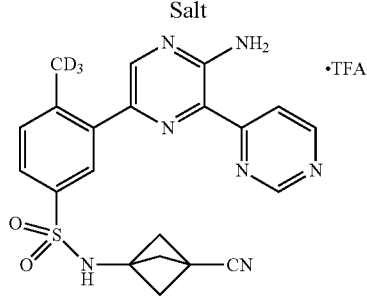 | Calculated for $C_{22}H_{22}D_3N_6O_3S_2$ $(M + H)^+$: m/z = 488.2, found: 488.1 |
| 78 | 3-(5-Amino-6-(2-(methylthio)pyrimidin-4-yl)pyrazin-2-yl)-N-(3-(hydroxymethyl)bicyclo[1.1.1]pentan-1-yl)-4-(methyl-d₃)benzenesulfonamide | | Calculated for $C_{22}H_{22}D_3N_6O_3S_2$ $(M + H)^+$: m/z = 488.2, found: 488.1 |

Example 79. 3-(5-Amino-6-(pyrimidin-4-yl)pyrazin-2-yl)-N-(3-cyanobicyclo[1.1.1]pentan-1-yl)-4-(methyl-d₃)benzenesulfonamide Trifluoroacetate Salt To 3-(5-amino-6-(2-(methylthio)pyrimidin-4-yl)pyrazin-2-yl)-N-(3-cyanobicyclo[1.1.1]pentan-1-yl)-4-(methyl-d₃) benzenesulfonamide (0.020 g, 0.041 mmol, from Example 76) in THF (1.0 mL) at 0° C. was added Pd on C (10%) (8.8 mg, 8.3 μmol) and triethylsilane (0.13 mL, 0.83 mmol). The mixture was degassed, then was stirred at room temperature for 2 hours. Trifluoroacetic acid (0.30 mL) was added, and the reaction mixture was stirred for 10 minutes. Volatiles were removed in vacuo and the sample was diluted with a mixture of acetonitrile, methanol and water, was filtered and purified via preparative HPLC-MS (pH 2) to afford product as a light yellow solid (6.1 mg, 27%). LCMS calculated for $C_{21}H_{17}D_3N_7O_2S$ $(M+H)^+$: m/z=437.2, found: 437.2. ¹H NMR (400 MHz, DMSO-d₆) δ 9.34 (d, J=1.1 Hz, 1H), 8.96-8.92 (m, 2H), 8.51 (s, 1H), 8.42 (dd, J=5.5, 1.2 Hz, 1H), 7.93 (d, J=2.0 Hz, 1H), 7.75 (dd, J=8.0, 2.0 Hz, 1H), 7.59 (d, J=8.0 Hz, 1H), 2.27 (s, 6H).

Examples 80-81

Unless otherwise indicated, the compounds of Examples 80-81 in Table 11 were synthesized according to the procedure described for using the appropriate methylthio precursors, e.g., Examples 77 and/or 78.

TABLE 11

| Example No. | Compound Name ¹H NMR | W | LCMS |
|---|---|---|---|
| 80 | 3-(5-Amino-6-(pyrimidin-4-yl)pyrazin-2-yl)-N-(4-hydroxybicyclo[2.1.1]hexan-1-yl)-4-(methyl-d₃)benzenesulfonamide trifluoroacetate salt | 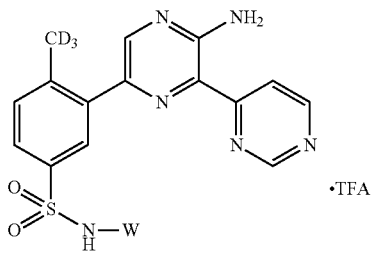 | Calculated for $C_{21}H_{20}D_3N_6O_3S$ $(M + H)^+$: m/z = 442.2, found: 442.3 |

TABLE 11-continued

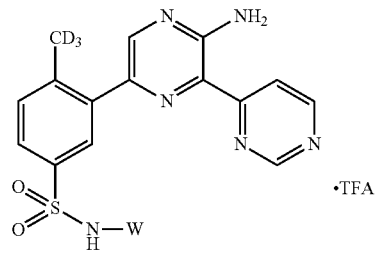

| Example No. | Compound Name<br>$^1$H NMR | W | LCMS |
|---|---|---|---|

$^1$H NMR (400 MHz, DMSO-d$_6$) δ 9.34 (d, J = 1.2 Hz, 1H), 8.93 (d, J = 5.5 Hz, 1H), 8.49 (s, 1H), 8.44 (dd, J = 5.5, 1.4 Hz, 1H), 8.25 (s, 1H), 7.96 (d, J = 2.0 Hz, 1H), 7.74 (dd, J = 8.0, 2.0 Hz, 1H), 7.56 (d, J = 8.0 Hz, 1H), 1.69-1.54 (m, 2H), 1.51-1.39 (m, 4H), 1.39-1.28 (m, 2H).

| 81 | 3-(5-Amino-6-(pyrimidin-4-yl)pyrazin-2-yl)-N-(3-(hydroxymethyl)bicyclo[1.1.1]pentan-1-yl)-4-(methyl-d$_3$)benzenesulfonamide trifluoroacetate salt | 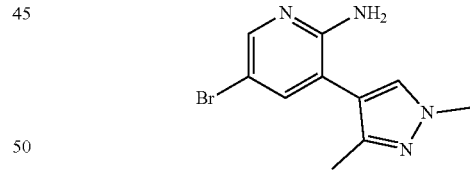 | Calculated for $C_{21}H_{20}D_3N_6O_3S$ $(M + H)^+$: m/z = 442.2, found: 442.3 |

$^1$H NMR (400 MHz, DMSO-d$_6$) δ 9.34 (d, J = 1.0 Hz, 1H), 8.94 (d, J = 5.5 Hz, 1H), 8.52 (s, 1H), 8.49 (s, 1H), 8.43 (dd, J = 5.4, 1.2 Hz, 1H), 7.95 (d, J = 1.9 Hz, 1H), 7.74 (dd, J = 8.0, 1.9 Hz, 1H), 7.57 (d, J = 8.0 Hz, 1H), 3.36 (s, 2H), 1.61 (s, 6H).

Example 82. 3-(6-Amino-5-(1,3-dimethyl-1H-pyrazol-4-yl)pyridin-3-yl)-N-(4-cyanobicyclo[2.1.1]hexan-1-yl)-4-methylbenzenesulfonamide

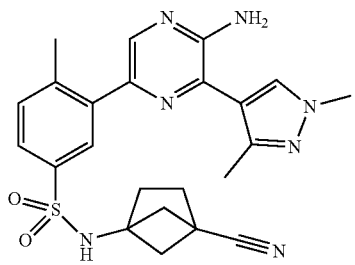 [SMILES: Cc1ccc(S(=O)(=O)NC23CCC(C#N)(C2)C3)cc1-c1cnc(N)c(-c2cn(C)nc2C)n1]

Step 1. 5-Chloro-3-(1,3-dimethyl-1H-pyrazol-4-yl)pyridin-2-amine

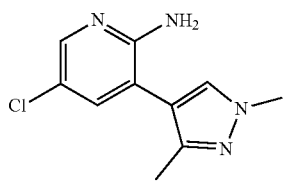

A 40 mL vial was charged with 3-bromo-5-chloropyridin-2-amine (200 mg, 0.96 mmol), cesium fluoride (510 mg, 3.37 mmol), 1,3-dimethyl-4-(4,4,5,5-tetramethyl-1,3,2-dioxaborolan-2-yl)-1H-pyrazole (240 mg, 1.06 mmol), 4-(di-tert-butylphosphino)-N,N-dimethylaniline-dichloropalladium (2:1) (17 mg, 0.024 mmol), 1-butanol (3 mL) and water (0.75 mL). The mixture was sparged with N$_2$ for 5 min, then heated to 60° C. for 2 hrs. The reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-100% EtOAc/hexanes) to afford the title compound (244 mg, 113%). LCMS calculated for $C_{10}H_{12}ClN_4(M+H)^+$: m/z=223.1, found 223.1.

Step 1. 5-Bromo-3-(1,3-dimethyl-1H-pyrazol-4-yl)pyridin-2-amine

A 40 mL vial was charged with 5-bromo-3-iodopyridin-2-amine (500 mg, 1.67 mmol), cesium fluoride (890 mg, 5.85 mmol), 1,3-dimethyl-4-(4,4,5,5-tetramethyl-1,3,2-dioxaborolan-2-yl)-1H-pyrazole (410 mg, 1.84 mmol), 4-(di-tert-butyl phosphino)-N,N-dimethylaniline-dichloropalladium (2:1) (30 mg, 0.042 mmol), 1-butanol (5.2 mL) and water (1.3 mL). The mixture was sparged with N$_2$ for 5 min, then heated to 60° C. for 2 hrs. The reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-100% EtOAc/hexanes) to afford the title compound (190 mg, 42%). LCMS calculated for $C_{10}H_{12}BrN_4(M+H)^+$: m/z=267.0, found 267.1.

Step 2: 3-(1,3-Dimethyl-1H-pyrazol-4-yl)-5-(o-tolyl)pyridin-2-amine

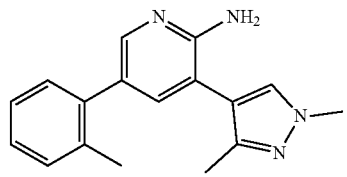

A crimp-cap vial was charged with 5-chloro-3-(1,3-dimethyl-1H-pyrazol-4-yl)pyridin-2-amine (243.0 mg, 1.091 mmol), o-tolylboronic acid (297 mg, 2.18 mmol), bis(di-tert-butyl(4-dimethylaminophenyl)phosphine)dichloropalladium(II) (19.3 mg, 0.027 mmol), and cesium fluoride (580 mg, 3.82 mmol). Butan-1-ol (8 ml) and water (2 ml) were added, and $N_2$ was bubbled through the mixture for 5 mins. The vial was sealed and heated to 90° C. for 2 hrs in an oil bath. The reaction mixture was cooled to rt, partitioned between water and EtOAc, and the layers were separated. The aqueous layer was extracted with EtOAc and the combined organic layers were washed with brine, dried over $MgSO_4$, filtered, and concentrated. The residue was purified by flash chromatography (0-100% EtOAc/hexanes) to afford the title compound (202 mg, 67%). LCMS calculated for $C_{17}H_{19}N_4(M+H)^+$: m/z=279.1, found 279.1.

Step 3: 3-(6-Amino-5-(1,3-dimethyl-1H-pyrazol-4-yl)pyridin-3-yl)-4-methylbenzenesulfonyl Chloride

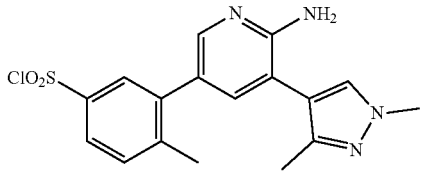

To a solution of 3-(1,3-dimethyl-1H-pyrazol-4-yl)-5-(o-tolyl)pyridin-2-amine (50 mg, 0.18 mmol) in DCM (4 ml) at 0° C. was added chlorosulfonic acid (0.12 ml, 1.80 mmol). The reaction mixture was allowed to warm to rt, then heated to 50° C. for 1 h. The reaction was carefully quenched by dropwise addition to a rapidly stirring mixture of DCM and ice. The precipitate that formed was filtered and the solid was washed with water and DCM. The filtrate was transferred to a separatory funnel and the layers were separated. The aqueous layer was extracted with DCM and the combined organic layers were dried over $MgSO_4$, filtered and concentrated to tan solid. This solid was combined with the solid from the first filtration, triturated with ether to afford the title compound (27 mg, 39%). LCMS calculated for $C_{17}H_{18}ClN_4O_2S$ $(M+H)^+$: m/z=377.1, found 377.1.

Step 4: 3-(6-Amino-5-(1,3-dimethyl-1H-pyrazol-4-yl)pyridin-3-yl)-N-(4-cyanobicyclo[2.1.1]hexan-1-yl)-4-methylbenzenesulfonamide

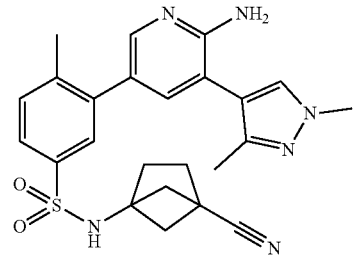

To a solution of 4-aminobicyclo[2.1.1]hexane-1-carbonitrile hydrochloride (5.0 mg, 0.032 mmol) and DIPEA (0.014 ml, 0.08 mmol) in DMA (2.0 ml) at 0° C. was added a solution of 3-(6-amino-5-(1,3-dimethyl-1H-pyrazol-4-yl)pyridin-3-yl)-4-methylbenzenesulfonyl chloride (10 mg, 0.027 mmol) in DMA (1 mL) dropwise. The 0° C. bath was removed, and the reaction mixture was stirred at rt for 1 h. The reaction mixture was diluted with MeOH and purified by prep LC/MS using pH 10 buffer to give the title compound (5.6 mg, 46%). LCMS calculated for $C_{24}H_{27}N_6O_2S$ $(M+H)^+$: m/z=463.1, found 463.1. $^1$H NMR (DMSO) δ: 8.58 (s, 1H), 7.90 (d, J=2.4 Hz, 1H), 7.77 (s, 1H), 7.66 (dd, J=8.0, 2.1 Hz, 1H), 7.62 (d, J=2.1 Hz, 1H), 7.49 (d, J=8.1 Hz, 1H), 7.29 (d, J=2.4 Hz, 1H), 5.74 (s, 2H), 3.79 (s, 3H), 2.36 (s, 3H), 2.13 (s, 3H), 1.95-1.89 (m, 2H), 1.85 (dd, J=8.0, 5.5 Hz, 2H), 1.69-1.62 (m, 2H), 1.56 (dd, J=4.0, 1.9 Hz, 2H).

Examples 83-87 and 89

Unless otherwise indicated, the compounds of Examples 83-87 and 89 in Table 12 were synthesized according to the procedure described for Example 82, using 7-1 or 7-2 (as shown in Scheme 7) with the appropriate boronic esters for Step 1 and utilizing appropriate amines for Step 4.

TABLE 12

| Example No. | Compound Name | Y $^1$H NMR Spectrum | W | LCMS [M + H]$^+$ |
|---|---|---|---|---|
| 84 | 3-(6-amino-5-(1,3-dimethyl-1H-pyrazol-4-yl)pyridin-3-yl)-N-(1-(hydroxymethyl)-2-oxabicyclo[2.1.1]hexan-4-yl)-4-methylbenzenesulfonamide | pyrazole | oxabicyclohexane-CH2OH | 470.2 |

TABLE 12-continued

| Example No. | Compound Name | Y | W | LCMS [M + H]+ |
|---|---|---|---|---|
| | ¹H NMR Spectrum | | | |
| 85 | 3-(6-amino-5-(2-methylthiazol-5-yl)pyridin-3-yl)-N-(4-cyanobicyclo[2.1.1]hexan-1-yl)-4-methylbenzenesulfonamide | 2-methylthiazol-5-yl | 4-cyanobicyclo[2.1.1]hexan-1-yl | 466.1 |
| | ¹H NMR (DMSO) δ: 8.58 (s, 1H), 8.01 (d, J = 2.3 Hz, 1H), 7.83 (s, 1H), 7.68 (dd, J = 8.0, 2.1 Hz, 1H), 7.63 (d, J = 2.1 Hz, 1H), 7.52-7.47 (m, 1H), 6.13 (s, 2H), 2.68 (s, 3H), 2.35 (s, 3H), 1.95-1.91 (m, 2H), 1.88-1.83 (m, 2H), 1.69-1.63 (m, 2H), 1.56 (dd, J = 4.0, 1.9 Hz, 2H) | | | |
| 86 | 3-(6-amino-5-(2-methylthiazol-5-yl)pyridin-3-yl)-N-(1-(hydroxymethyl)-2-oxabicyclo[2.1.1]hexan-4-yl)-4-methylbenzenesulfonamide | 2-methylthiazol-5-yl | 1-(hydroxymethyl)-2-oxabicyclo[2.1.1]hexan-4-yl | 473.1 |
| | ¹H NMR (DMSO) δ: 8.64 (s, 1H), 8.00 (d, J = 2.3 Hz, 1H), 7.83 (s, 1H), 7.69 (dd, J = 8.0, 2.0 Hz, 1H), 7.65 (d, J = 2.0 Hz, 1H), 7.50 (d, J = 8.1 Hz, 1H), 7.49 (d, J = 2.3 Hz, 1H), 6.13 (s, 2H), 4.64 (t, J = 5.9 Hz, 1H), 3.53 (s, 2H), 3.43 (d, J = 5.8 Hz, 2H), 2.68 (s, 3H), 2.35 (s, 3H), 1.64-1.59 (m, 2H), 1.39-1.34 (m, 2H) | | | |
| 87 | 3-(6-amino-5-(2-methylthiazol-5-yl)pyridin-3-yl)-N-(3-(hydroxymethyl)bicyclo[1.1.1]pentan-1-yl)-4-methylbenzenesulfonamide | 2-methylthiazol-5-yl | 3-(hydroxymethyl)bicyclo[1.1.1]pentan-1-yl | 457.2 |
| | ¹H NMR (DMSO) δ: 8.42 (s, 1H), 8.00 (d, J = 2.3 Hz, 1H), 7.83 (s, 1H), 7.65 (dd, J = 8.0, 2.0 Hz, 1H), 7.61 (d, J = 2.0 Hz, 1H), 7.49 (d, J = 8.2 Hz, 1H), 7.48 (d, J = 2.4 Hz, 1H), 6.13 (s, 2H), 4.40 (t, J = 5.7 Hz, 1H), 3.33 (d, J = 5.6 Hz, 2H), 2.68 (s, 3H), 2.35 (s, 3H), 1.55 (s, 6H) | | | |
| 89 | 3-(6-amino-5-(2-cyclopropylthiazol-5-yl)pyridin-3-yl)-N-(1-(hydroxymethyl)-2-oxabicyclo[2.1.1]hexan-4-yl)-4-methylbenzenesulfonamide | 2-cyclopropylthiazol-5-yl | 1-(hydroxymethyl)-2-oxabicyclo[2.1.1]hexan-4-yl | 499.2 |

Examples 90-95

Unless otherwise indicated, the compounds of Examples 90-95 in Table 13 were synthesized according to the procedure described for Example 52, Step 3, utilizing the appropriate sulfonyl chlorides and 1-azabicyclo[2.2.1]heptan-4-amine dihydrochloride (Enamine, Cat. I.: EN300-342668) instead of 2-azabicyclo[2.1.1]hexan-4-amine dihydrochloride.

TABLE 13

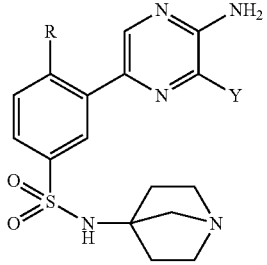

| Example No. | Compound Name | R | Y | LCMS [M + H]+ |
|---|---|---|---|---|
| 90 | 3-(5-amino-6-(1H-1,2,4-triazol-1-yl)pyrazin-2-yl)-N-(1-azabicyclo[2.2.1]heptan-4-yl)-4-(methyl-d3)benzenesulfonamide | —CD3 | 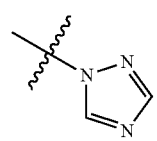 [SMILES: *n1cncn1] | 430.2 |
| 91 | 3-(5-amino-6-(2-methylthiazol-5-yl)pyrazin-2-yl)-N-(1-azabicyclo[2.2.1]heptan-4-yl)-4-(methyl-d3)benzenesulfonamide | —CD3 | 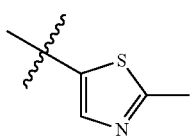 [SMILES: *c1cnc(C)s1] | 460.1 |
| 92 | 3-(5-amino-6-(1-(methyl-d3)-1H-1,2,4-triazol-3-yl)pyrazin-2-yl)-N-(1-azabicyclo[2.2.1]heptan-4-yl)-4-(methyl-d3)benzenesulfonamide | —CD3 | 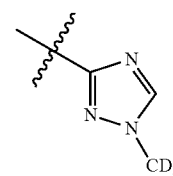 | 447.2 |
| 93 | 3-(5-amino-6-(1H-pyrazol-1-yl)pyrazin-2-yl)-N-(1-azabicyclo[2.2.1]heptan-4-yl)-4-methylbenzenesulfonamide | —CH3 | 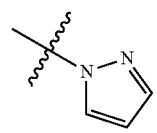 [SMILES: *n1cccn1] | 426.2 |
| 94 | 3-(5-amino-6-(oxazol-5-yl)pyrazin-2-yl)-N-(1-azabicyclo[2.2.1]heptan-4-yl)-4-(methyl-d3)benzenesulfonamide | —CD3 | 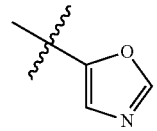 [SMILES: *c1cnco1] | 430.1 |
| 95 | 3-(5-amino-6-(pyrimidin-4-yl)pyrazin-2-yl)-N-(1-azabicyclo[2.2.1]heptan-4-yl)-4-(methyl-d3)benzenesulfonamide | —CD3 | 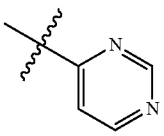 [SMILES: *c1ccncn1] | 441.1 |

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, Va.) and maintained in RPMI with 10% FBS (Gibco/Life Technologies, Carlsbad, Calif.). For the assay, THP-1 cells are serum starved overnight in RPMI, then plated in RPMI ($2\times10^5$ cells/well in 90 µL) into 96-well flat-bottom tissue culture treated plates (Corning, Corning, N.Y.), in the presence or absence of a concentration range of test compounds. Covered plates are incubated for 2 hours at 37° C., 5% $CO_2$ then treated with or without 10 nM MCP-1 (MYBioSource, San Diego, Calif.) for 15 minutes at 37° C., 5% $CO_2$. Plates are centrifuged at 1600 RPM and supernatants are removed. Cells are lysed in Lysis Buffer (Cell Signaling, Danvers, Mass.) with Protease Inhibitor (Calbiochem/EMD, Germany), PMSF (Sigma, St Louis Mo.), HALTS (Thermo Fisher, Rockford, Ill.) for 30 min on wet ice. Cell lysates are frozen at −80° C. before testing. The lysates are tested in the Human/Mouse/Rat Phospho-RPS6 ELISA (R&D Systems, Inc. Minn, Minn.). The plate is measured using a microplate reader (SpectraMax M5—Molecular Devices, LLC Sunnyvale, Calif.) set to 450 nm with a wavelength correction of 540. $IC_{50}$ determination is performed by fitting the curve of inhibitor percent inhibition versus the log of the inhibitor concentration using the GraphPad Prism 5.0 software.

Example B. PI3K-γ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, Mass.). Lipid kinase substrate, D-myo-Phosphatidylinositol 4,5-bisphosphate (PtdIns(4,5) P2)D (+)-sn-1,2-di-O-octanoylglyceryl, 3-O-phospho linked (PIP2), CAS 204858-53-7, was purchased from Echelon Biosciences (Salt Lake City, Utah). PI3Kγ (p110γ) Recombinant Human Protein was purchased from Life technology (Grand island, NY), ATP, $MgCl_2$, DTT, EDTA, MOPS and CHAPS were purchased from Sigma-Aldrich (St. Louis, Mo.).

The kinase reaction was conducted in polystyrene 384-well Greiner Bio-one white plate from Thermo Fisher Scientific in a final volume of 25 µL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 µM PIP2, 2 µM ATP, 0.5 µCi [γ-$^{33}$P] ATP, 13 nM PI3Kγ. Reactions were incubated for 120 min and terminated by the addition of 40 µL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). $IC_{50}$ determination was performed by fitting the curve of percent of the solvent control activity versus the log of the inhibitor concentration using the GraphPad Prism 6.0 software. Data for the Examples, obtained using the methods described in Example B, are provided in Table 4.

Example C. PI3Kδ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, Mass.). Lipid kinase substrate, D-myo-Phosphatidylinositol 4,5-bisphosphate (PtdIns(4,5) P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) Recombinant Human Protein was purchased from Eurofins (St Charles, Mo.). ATP, $MgCl_2$, DTT, EDTA, MOPS and CHAPS were purchased from Sigma-Aldrich (St. Louis, Mo.).

The kinase reaction was conducted in polystyrene 384-well Greiner Bio-one white plate from Thermo Fisher Scientific in a final volume of 25 µL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 µM PIP2, 2 µM ATP, 0.5 µCi [γ-$^{33}$P] ATP, 3.4 nM PI3Kδ. Reactions were incubated for 120 min and terminated by the addition of 40 µL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). $IC_{50}$ determination was performed by fitting the curve of percent of the solvent control activity versus the log of the inhibitor concentration using the GraphPad Prism 6.0 software.

Data for the Examples, obtained using the methods described in Examples A, B and C, are provided in Table A.

TABLE A

| Ex. No. | PI3Kγ $IC_{50}$ (nM) | PI3Kδ $IC_{50}$ (nM) | PI3Kγ_THP1_RPS6_ELISA $IC_{50}$ (nM) |
|---|---|---|---|
| 1 | + | + | # |
| 2 | + | + | # |
| 3 | + | + | # |
| 4 | + | + | # |
| 5 | + | + | # |
| 6 | + | + | # |
| 7 | + | + | # |
| 8 | + | + | # |
| 9 | + | + | # |
| 10 | + | + | ## |
| 11 | + | ++ | ## |
| 12 | + | ++ | ## |
| 13 | + | ++ | ## |
| 14 | + | ++ | ## |
| 15 | + | ++ | ## |
| 16 | + | + | ## |
| 17 | + | ++ | ## |
| 18 | + | ++ | ## |
| 19 | + | + | ### |
| 20 | + | ++ | ## |
| 21 | + | ++ | ## |
| 22 | +++ | ++++ | — |
| 23 | + | + | ## |
| 24 | + | ++ | # |
| 25 | + | + | # |
| 26 | + | + | # |
| 27 | + | ++ | ## |
| 28 | + | ++ | # |

TABLE A-continued

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 29 | + | ++ | ## |
| 30 | + | ++ | ## |
| 31 | + | ++ | ## |
| 32 | + | +++ | − |
| 33 | + | ++ | − |
| 34 | + | ++ | #### |
| 35 | + | ++ | ### |
| 36 | + | ++++ | − |
| 37 | + | ++++ | − |
| 39 | + | ++ | ## |
| 40 | + | ++ | ### |
| 41 | + | + | # |
| 42 | + | ++ | # |
| 43 | + | ++ | # |
| 44 | + | + | # |
| 45 | + | ++ | ## |
| 46 | + | + | ## |
| 47 | + | + | # |
| 48 | + | ++ | # |
| 49 | + | + | ## |
| 50 | + | + | ## |
| 51 | + | +++ | − |
| 52 | ++ | ++ | − |
| 53 | + | ++ | − |
| 54 | + | + | ## |
| 55 | + | + | ## |
| 56 | + | ++ | ### |
| 57 | + | + | ## |
| 58 | + | ++ | ### |
| 59 | + | ++ | ### |
| 60 | + | ++ | NT |
| 61 | + | + | # |
| 62 | + | + | # |
| 63 | + | + | # |
| 64 | + | ++ | # |
| 65 | + | + | # |
| 66 | + | + | # |
| 67 | + | ++ | # |
| 69 | + | + | # |
| 70 | + | +++ | #### |
| 71 | + | ++ | ## |
| 72 | + | + | # |
| 73 | + | + | # |
| 74 | + | ++ | # |
| 75 | + | ++ | # |
| 76 | + | + | # |
| 77 | + | + | # |
| 78 | + | + | # |
| 79 | + | + | # |
| 80 | + | + | # |
| 81 | + | + | ## |
| 82 | + | ++ | ### |
| 84 | ++ | ++ | − |
| 85 | + | + | # |
| 86 | + | ++ | ## |
| 87 | + | + | # |
| 89 | + | ++ | # |
| 90 | + | + | # |
| 91 | + | + | # |
| 92 | + | + | ## |
| 93 | + | + | # |
| 94 | + | ++ | # |
| 95 | + | + | # |

+refers to IC$_{50}$ of ≤100 nM; ++refers to IC$_{50}$ of ≤500 nM; +++refers to an IC$_{50}$ of <2000 nM; ++++refers to an IC$_{50}$ of ≥2000 nM.
refers to IC$_{50}$ of ≤100 nM; ##refers to IC$_{50}$ of ≤500 nM; ###refers to IC$_{50}$ of ≤1000 nM; ####refers to an IC$_{50}$ of ≥1000 nM.
−refers to data not available.

Compounds are considered active if the assay results are less than 2 mM.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

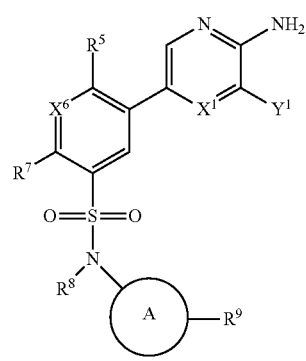

or a pharmaceutically acceptable salt thereof; wherein:
$X^1$ is N or $CR^1$;
$X^6$ is N or $CR^6$;
Ring A is a $C_{5-10}$ bridged bicycloalkyl which is optionally substituted by 1, 2, 3, or 4 independently selected $R^2$ groups;
$Y^1$ is a $C_{6-10}$ aryl, $C_{3-10}$ cycloalkyl, 5-14 membered heteroaryl, or 4-14 membered heterocycloalkyl, wherein the $C_{6-10}$ aryl, $C_{3-10}$ cycloalkyl, 5-14 membered heteroaryl and 4-14 membered heterocycloalkyl of $Y^1$ are each optionally substituted with 1, 2, 3, or 4 independently selected $R^b$ substituents;
$R^1$, $R^5$, $R^6$, and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NR$^a$R$^a$, NR$^a$C(O)R$^a$, NR$^a$C(O)OR$^a$, NR$^a$C(O)NR$^a$R$^a$, C(=NR$^k$)R$^a$, C(=NR$^k$)NR$^a$R$^a$, NR$^a$C(=NR$^k$)NR$^a$R$^a$    NR$^a$C(=NOH)NR$^a$R$^a$,   NR$^a$C(=NCN)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, S(O)(=NR$^k$)R$^a$, SF$_5$, —P(O)R$^a$R$^a$, —P(O)(OR$^a$)(OR$^a$), B(OR$^a$)$_2$ and S(O)$_2$NR$^a$R$^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 5-14 membered heterocycloalkyl-$C_{1-4}$ alkyl- of $R^1$, $R^5$, $R^6$ and $R^7$ are each optionally substituted with 1, 2, 3, or 4 independently selected $R^b$ substituents;

each $R^2$ is independently selected from D, OH, NO$_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^8$ is selected from H, D, CN, OH, $C_{1-6}$ alkyl, $C_{1-6}$ alkoxy, $C_{2-6}$ alkenyl, $C_{2-6}$ alkynyl, and $C_{1-6}$ haloalkyl;

$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR''$, $SR''$, $NHOR''$, $C(O)R''$, $C(O)NR''R''$, $C(O)OR''$, $OC(O)R''$, $OC(O)NR''R''$, $NR''R''$, $NR''C(O)R''$, $NR''C(O)OR''$, $NR''C(O)NR''R''$, $C(=NR^k)R''$, $C(=NR^k)NR''R''$, $NR''C(=NR^k)NR''R''$, $NR''C(=NOH)NR''R''$, $NR''C(=NCN)NR''R''$, $NR''S(O)R''$, $NR''S(O)_2R''$, $NR''S(O)_2NR''R''$, $S(O)R''$, $S(O)NR''R''$, $S(O)_2R''$, $S(O)(=NR^k)R''$, $SF_5$, —$P(O)R''R''$, —$P(O)(OR'')(OR'')$, $B(OR'')_2$ and $S(O)_2NR''R''$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^9$ are each optionally substituted with 1, 2, 3, or 4 independently selected $R^m$ substituents;

each $R^a$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^c(O)OR^c$, $NR^c(O)NR^cR^c$, $C(=NR^k)R^c$, $C(=NR^k)NR^cR^c$, $NR^c(=NR^k)NR^cR^c$, $NR^c(=NOH)NR^cR^c$, $NR^c(=NCN)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)(=NR^k)R^c$, $SF_5$, —$P(O)R^cR^c$, —$P(O)(OR^c)(OR^c)$, $B(OR^c)_2$ and $S(O)_2NR^cR^c$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^b$ is each optionally substituted with 1, 2, 3, or 4 independently selected $R^d$ substituents;

each $R^c$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^k)R^e$, $C(=NR^k)NR^eR^e$, $NR^eC(=NR^k)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, $S(O)(=NR^k)R^e$, $SF_5$, —$P(O)R^eR^e$, —$P(O)(OR^e)(OR^e)$, $B(OR^e)_2$ and $S(O)_2NR^eR^e$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^d$ is each optionally substituted with 1, 2, 3, or 4 independently selected $R^f$ substituents;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^e$ is each optionally substituted with 1, 2, 3, or 4 independently selected $R^f$ substituents;

each $R^f$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^g$, $SR^g$, $NHOR^g$, $C(O)R^g$, $C(O)NR^gR^g$, $C(O)OR^g$, $OC(O)R^g$, $OC(O)NR^gR^g$, $NR^gR^g$, $NR^gC(O)R^g$, $NR^gC(O)OR^g$, $NR^gC(O)NR^gR^g$, $C(=NR^k)R^g$, $C(=NR^k)NR^gR^g$, $NR^gC(=NR^k)NR^gR^g$, $NR^gC(=NOH)NR^gR^g$, $NR^gC(=NCN)NR^gR^g$, $NR^gS(O)R^g$, $NR^gS(O)_2R^g$, $NR^gS(O)_2NR^gR^g$, $S(O)R^g$, $S(O)NR^gR^g$, $S(O)_2R^g$, $S(O)(=NR^k)R^g$, $SF_5$, —$P(O)R^gR^g$, —$P(O)(OR^g)(OR^g)$, $B(OR^g)_2$ and $S(O)_2NR^gR^g$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^f$ is each optionally substituted with 1, 2, 3, or 4 independently selected $R^h$ substituents;

each $R^g$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5+-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^g$ is each optionally substituted with 1, 2, 3m or 4 independently selected $R^h$ substituents;

each $R^h$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^h$ is each optionally substituted with 1 or 2 independently selected $R^i$ substituents;

each $R^i$ is independently selected from H, D, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-;

each $R^k$ is independently selected from H, CN, OH, $C_{1-4}$ alkyl, and $C_{1-4}$ alkoxy;

each $R^m$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two $R^n$ substituents, together with the atom to which they attached form a 4-, 5-, 6, or 7-membered heterocycloalkyl group, wherein said heterocycloalkyl group is optionally substituted by 1, 2, 3, or 4 independently selected $R^m$ groups.

2. The compound of claim 1, or a pharmaceutically acceptable salt thereof, wherein Ring A is a $C_{5-10}$ bridged bicycloalkyl.

3. The compound of claim 1, or a pharmaceutically acceptable salt thereof, wherein Ring A is selected from bicyclo[1.1.1]pentanylene, bicyclo[2.1.1]hexanylene, bicyclo[2.2.1]heptanylene, and bicyclo[2.2.2]octanylene, each of which is optionally substituted by 1, 2, or 3 independently selected $R^2$ groups.

4. The compound of claim 1, or a pharmaceutically acceptable salt thereof, wherein Ring A is selected from

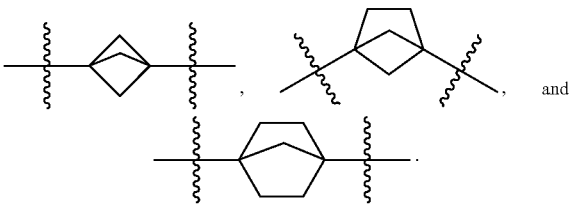

5. The compound of claim 1, or a pharmaceutically acceptable salt thereof, wherein $X^1$ is N or CH.

6. The compound of claim 1, or a pharmaceutically acceptable salt thereof, wherein $X^1$ is N.

7. The compound of claim 1, or a pharmaceutically acceptable salt thereof, wherein $X^1$ is CH.

8. The compound of claim 1, or a pharmaceutically acceptable salt thereof, wherein $R^5$ is $C_{1-6}$ alkyl or $CD_3$.

9. The compound of claim 1, or a pharmaceutically acceptable salt thereof, wherein $R^5$ is methyl or —$CD_3$.

10. The compound of claim 1, or a pharmaceutically acceptable salt thereof, wherein $X^6$ is $CR^6$.

11. The compound of claim 10, or a pharmaceutically acceptable salt thereof, wherein $R^6$ is H or halo.

12. The compound of claim 10, or a pharmaceutically acceptable salt thereof, wherein $R^6$ is H or fluoro.

13. The compound of claim 1, or a pharmaceutically acceptable salt thereof, wherein $X^6$ is N.

14. The compound of claim 1, or a pharmaceutically acceptable salt thereof, wherein $R^7$ is H.

15. The compound of claim 1, or a pharmaceutically acceptable salt thereof, wherein $R^8$ is H.

16. The compound of claim 1, or a pharmaceutically acceptable salt thereof, wherein $R^7$ and $R^8$ are each H.

17. The compound of claim 1, or a pharmaceutically acceptable salt thereof, wherein $Y^1$ is phenyl, $C_{3-7}$ cycloalkyl, 5-6 membered heteroaryl, or 4-7 membered heterocycloalkyl, wherein the phenyl, $C_{3-7}$ cycloalkyl, 5-6 membered heteroaryl, or 4-7 membered heterocycloalkyl are each optionally substituted with 1, 2, 3, or 4 independently selected $R^b$ substituents.

18. The compound of claim 1, or a pharmaceutically acceptable salt thereof, wherein $Y^1$ is a 5-6 membered heteroaryl group which is optionally substituted by 1, 2, 3, or 4 independently selected $R^b$ substituents.

19. The compound of claim 1, or a pharmaceutically acceptable salt thereof, wherein $Y^1$ is selected from thiazolyl, pyrazolyl, triazolyl, tetrazolyl, oxazolyl, pyridyl, and pyrimidinyl, wherein the thiazolyl, pyrazolyl, triazolyl, tetrazolyl, oxazolyl, pyridyl, and pyrimidinyl are each optionally substituted by 1 or 2 independently selected $R^b$ substituents.

20. The compound of claim 1, or a pharmaceutically acceptable salt thereof, wherein $Y^1$ is selected from thiazolyl, pyrazolyl, triazolyl, tetrazolyl, oxazolyl, pyridyl, and pyrimidinyl, wherein the thiazolyl, pyrazolyl, triazolyl, tetrazolyl, oxazolyl, pyridyl, and pyrimidinyl are each optionally substituted by 1 or 2 independently selected $R^b$ substituents.

21. The compound of claim 1, or a pharmaceutically acceptable salt thereof, wherein the $R^b$ substituents on $Y^1$ are each independently selected from halo, $C_{1-6}$ alkyl, $C_{1-6}$ haloalkyl, $C_{3-10}$ cycloalkyl, CN, $NR^cR^c$, and $SR^c$.

22. The compound of claim 1, or a pharmaceutically acceptable salt thereof, wherein the $R^b$ substituents on $Y^1$ are each independently selected from fluoro, methyl, trifluoromethyl, cyclopropyl, CN, dimethylamino, and methylthio.

23. The compound of claim 1, or a pharmaceutically acceptable salt thereof, wherein $Y^1$ is selected from 2-methylthiazol-5-yl, 2-cyclopropylthiazol-5-yl, oxazol-2-yl, oxazol-5-yl, 2-methyloxazol-5-yl, 1H-pyrazol-1-yl, 1-methyl-1H-pyrazol-3-yl, 1,3-dimethyl-1H-pyrazol-4-yl, 1H-1,2,4-triazol-1-yl, 1H-1,2,3-triazol-1-yl, 2H-1,2,3-triazol-2-yl, 1-methyl-1H-1,2,4-triazol-3-yl, 2H-tetrazol-5-yl, pyridin-3-yl, pyridin-4-yl, 2-methylpyridin-4-yl, 2-cyanopyridin-4-yl, 3-fluoropyridin-4-yl, 2-(trifluoromethyl)pyridin-4-yl, 3-cyanopyridin-4-yl, pyrimidin-2-yl, pyrimidin-4-yl, pyrimidin-5-yl, 2-(methylthio)pyrimidin-4-yl, and 2-(dimethyl amino) pyrimidin-5-yl.

24. The compound of claim 1, or a pharmaceutically acceptable salt thereof, wherein $R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, $OR''$, $C(O)R''$, $C(O)NR''R''$, $C(O)OR''$, $OC(O)R''$, $OC(O)NR''R''$, $NR''R''$, $NR''C(O)R''$, $NR''C(O)OR''$, and $NR''C(O)NR''R''$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of $R^9$ are each optionally substituted with 1, 2, 3 or 4 independently selected $R^m$ substituents.

25. The compound of claim 1, or a pharmaceutically acceptable salt thereof, wherein $R^9$ is selected from H, $C_{1-6}$ alkyl, $C_{1-6}$ alkoxy, CN, $OR''$, $C(O)R''$, $C(O)NR''R''$, $NR''C(O)R''$, and $NR''C(O)OR''$, wherein the $C_{1-6}$ alkyl and $C_{1-6}$ alkoxy are each optionally substituted with 1 or 2 independently selected $R^m$ substituents.

26. The compound of claim 1, or a pharmaceutically acceptable salt thereof, wherein $R^9$ is selected from H, $C_{1-6}$ alkyl, $C_{1-6}$ alkoxy, CN, $OR''$, $C(O)R''$, $C(O)NR''R''$, $NR''C(O)R''$, and $NR''C(O)OR''$, wherein the $C_{1-6}$ alkyl are each optionally substituted with 1 or 2 $R^m$ groups selected from OH and —O—$C_{1-6}$ alkylcarbamyl, and each $R''$ is independently selected from H, $C_{1-6}$ alkyl, and $C_{1-6}$ haloalkyl; or two $R''$ substituents, together with the nitrogen atom to which they attached form a 4-, 5-, 6-, or 7-membered heterocycloalkyl group.

27. The compound of claim 1, or a pharmaceutically acceptable salt thereof, wherein $R^9$ is selected from H, CN, OH, methyl, 2-isopropyl, hydroxymethyl, 1-hydroxyethyl, 2-hydroxypropan-2-yl, —$CH_2OC(O)NHCH_3$, $C(O)NHCH_3$, $C(O)N(CH_3)_2$, $C(O)$-azetidin-1-yl, $C(O)NHCH_2CF_3$, $NHC(O)OCH_2CH_3$, and $NHC(O)CH_3$.

28. The compound of claim 1, or a pharmaceutically acceptable salt thereof, wherein:
$X^1$ is N or CH;
$X^6$ is N or $CR^6$;
Ring A is a $C_{5-10}$ bridged bicycloalkyl which is optionally substituted by 1, 2, 3, or 4 independently selected $R^2$ groups;
$R^2$ is selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O— carbamyl, —O—$C_{1-6}$ alkylcarbamyl, —O-di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
$R^5$ is $C_{1-6}$ alkyl;
$R^6$ is H or halo;
$R^7$ is H;
$R^8$ is H;
$Y^1$ is phenyl, $C_{3-7}$ cycloalkyl, 5-10 membered heteroaryl, or 4-10 membered heterocycloalkyl, wherein the phenyl, $C_{3-7}$ cycloalkyl, 5-10 membered heteroaryl, or 4-10 membered heterocycloalkyl are each optionally substituted with 1, 2, 3, or 4 independently selected $R^b$ substituents;
$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, $OR''$, $C(O)R''$, $C(O)NR''R''$, $C(O)OR''$, $OC(O)R''$, $OC(O)NR''R''$, $NR''R''$ $NR''C(O)R''$, $NR^1C(O)OR''$, and $NR''C(O)NR''R''$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of $R^9$ are each optionally substituted with 1, 2, 3 or 4 independently selected $R^m$ substituents;
each $R^b$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^c(O)R^c$, $NR^c(O)OR^c$, $NR^c(O)NR^cR^c$, $C(=NR^k)R^c$, $C(=NR^k)NR^cR^c$, $NR^c(=NR^k)NR^cR^c$, $NR^c(=NOH)NR^cR^c$, $NR^c(=NCN)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)(=NR^k)R^c$, $SF_5$, —$P(O)R^cR^c$, —$P(O)(OR^c)(OR^c)$, $B(OR^c)_2$ and $S(O)_2NR^cR^c$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-4}$ alkyl- of $R^b$ is each optionally substituted with 1, 2, 3, or 4 independently selected $R^d$ substituents;

each $R^c$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-4}$ alkyl-, 5-14 membered heteroaryl-$C_{1-6}$ alkyl- and 4-14 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, 4-14 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^k)R^e$, $C(=NR^k)NR^eR^e$, $NR^eC(=NR^k)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, $S(O)(=NR^k)R^e$, $SF_5$, —$P(O)R^eR^e$, —$P(O)(OR^e)(OR^e)$, $B(OR^e)_2$ and $S(O)_2NR^eR^e$;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-14 membered heterocycloalkyl, $C_{6-10}$ aryl-$C_{1-6}$ alkyl-, $C_{3-10}$ cycloalkyl-$C_{1-6}$ alkyl-, 5-14 membered heteroaryl-$C_{1-6}$ alkyl-, and 4-14 membered heterocycloalkyl-$C_{1-6}$ alkyl-;

each $R^k$ is independently selected from H, CN, OH, $C_{1-4}$ alkyl, and $C_{1-4}$ alkoxy;

each $R^m$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^n$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two $R^n$ substituents, together with the atom to which they attached form a 4-, 5-, 6, or 7-membered heterocycloalkyl group.

29. The compound of claim 1, or a pharmaceutically acceptable salt thereof, wherein:
$X^1$ is N or CH;
$X^6$ is N or $CR^6$;
Ring A is bicyclo[1.1.1]pentanylene, bicyclo[2.1.1]hexanylene, bicyclo[2.2.1]heptanylene, or bicyclo[2.2.2]octanylene;
$R^5$ is $C_{1-6}$ alkyl;
$R^6$ is H or halo;
$R^7$ is H;
$R^8$ is H;
$Y^1$ is a 5-6 membered heteroaryl group which is optionally substituted by 1, 2, 3, or 4 independently selected $R^b$ substituents;
$R^9$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, $OR''$, $C(O)R''$, $C(O)NR''R''$, $C(O)OR''$, $OC(O)R''$, $OC(O)NR''R''$, $NR''R''$ $NR''C(O)R''$, $NR''C(O)OR''$, and $NR''C(O)NR''R''$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy of $R^9$ are each optionally substituted with 1, 2, 3 or 4 independently selected $R'''$ substituents;
each $R^b$ is independently selected from halo, $C_{1-6}$ alkyl, $C_{1-6}$ haloalkyl, $C_{3-10}$ cycloalkyl, CN, $NR^cR^c$, and $SR^c$;
each $R^c$ is independently selected from H, D, and $C_{1-6}$ alkyl;
each $R'''$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, —O-carbamyl, —O—$C_{1-6}$ alkylcarbamyl, —O-di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R''$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, phenyl, $C_{3-6}$ cycloalkyl, 5-6 membered heteroaryl, and 4-6 membered heterocycloalkyl;

or any two $R''$ substituents, together with the atom to which they attached form a 4-, 5-, 6, or 7-membered heterocycloalkyl group.

30. The compound of claim 1, or a pharmaceutically acceptable salt thereof, wherein:
$X^1$ is N or CH;
$X^6$ is N or $CR^6$;
Ring A is

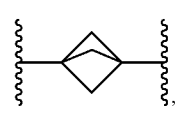 , 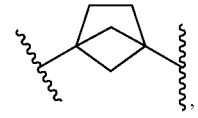 , or

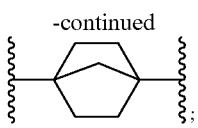

$R^5$ is $C_{1-6}$ alkyl;
$R^6$ is H or halo;
$R^7$ is H;
$R^8$ is H;
$Y^1$ is selected from thiazolyl, pyrazolyl, triazolyl, tetrazolyl, oxazolyl, pyridyl, and pyrimidinyl, wherein the thiazolyl, pyrazolyl, triazolyl, tetrazolyl, oxazolyl, pyridyl, and pyrimidinyl are each optionally substituted by 1 or 2 independently selected $R^b$ substituents;
$R^9$ is selected from H, $C_{1-6}$ alkyl, $C_{1-6}$ alkoxy, CN, OR'', C(O)R'', C(O)NR''R'', NR''C(O)R'', and NR''C(O)OR'', wherein the $C_{1-6}$ alkyl and $C_{1-6}$ alkoxy are each optionally substituted with 1 or 2 $R^m$ substituents;
each $R^b$ is independently selected from halo, $C_{1-6}$ alkyl, $C_{1-6}$ haloalkyl, $C_{3-10}$ cycloalkyl, CN, $NR^cR^c$, and $SR^c$;
each $R^c$ is independently selected from H, D, and $C_{1-6}$ alkyl;
each $R^m$ is independently selected from OH and —O—$C_{1-6}$ alkylcarbamyl; and
each R'' is independently selected from H, $C_{1-6}$ alkyl, and $C_{1-6}$ haloalkyl;
or any two R'' substituents, together with the atom to which they attached form a 4-, 5-, 6-, or 7-membered heterocycloalkyl group.

31. The compound of claim 1, or a pharmaceutically acceptable salt thereof, wherein the compound of Formula (I) is a compound of Formula (II):

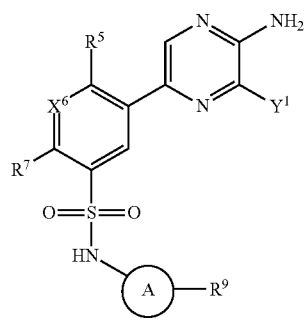

(II)

or a pharmaceutically acceptable salt thereof.

32. The compound of claim 1, wherein the compound of Formula (I) is a compound of Formula (III):

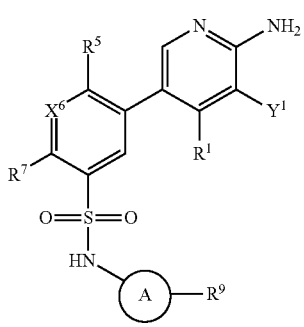

(III)

or a pharmaceutically acceptable salt thereof.

33. The compound of claim 1, wherein the compound of Formula (I) is a compound of Formula (IV):

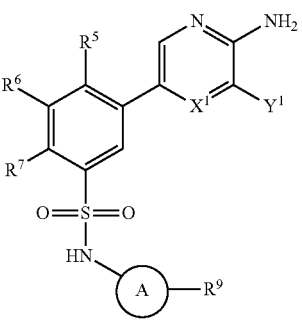

(IV)

or a pharmaceutically acceptable salt thereof.

34. The compound of claim 1, wherein the compound of Formula (I) is a compound of Formula (V):

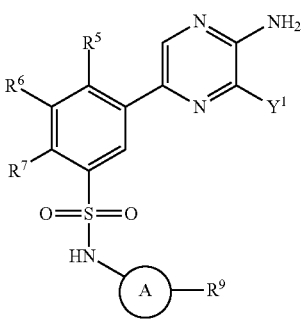

(V)

or a pharmaceutically acceptable salt thereof.

35. The compound of claim 1, wherein the compound of Formula (I) is a compound of Formula (VI):

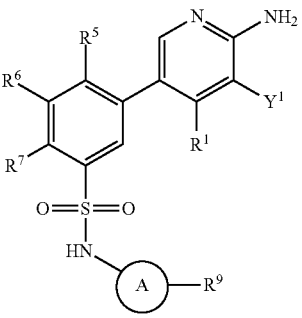

(VI)

or a pharmaceutically acceptable salt thereof.

36. The compound of claim 1, wherein the compound of Formula (I) is a compound of Formula (VII):

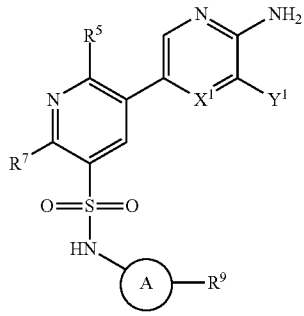

or a pharmaceutically acceptable salt thereof.

37. The compound of claim 1, wherein the compound of Formula (I) is a compound of Formula (VIII):

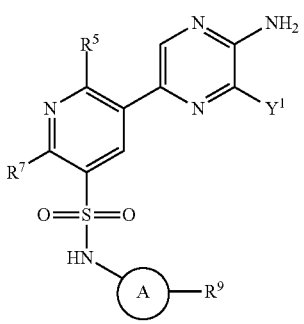

or a pharmaceutically acceptable salt thereof.

38. The compound of claim 1, wherein the compound of Formula (I) is a compound of Formula (IX):

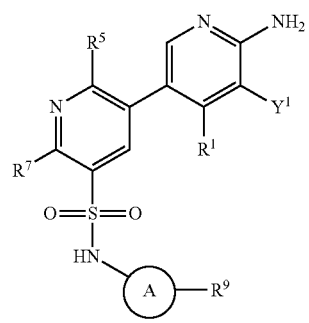

or a pharmaceutically acceptable salt thereof.

39. The compound of claim 1, selected from:
3-(5-Amino-6-(2-methylthiazol-5-yl)pyrazin-2-yl)-N-(3-cyanobicyclo[1.1.1]pentan-1-yl)-4-methylbenzenesulfonamide;
3-(5-Amino-6-(2-methylthiazol-5-yl)pyrazin-2-yl)-N-(4-cyanobicyclo[2.1.1]hexan-1-yl)-4-methylbenzenesulfonamide;
3-(5-Amino-6-(2-methylthiazol-5-yl)pyrazin-2-yl)-N-(3-(hydroxymethyl)bicyclo[1.1.1]pentan-1-yl)-4-methylbenzenesulfonamide;
3-(5-Amino-6-(2-methylthiazol-5-yl)pyrazin-2-yl)-N-(4-(hydroxymethyl)bicyclo[2.1.1]hexan-1-yl)-4-methylbenzenesulfonamide;
3-(5-Amino-6-(2-methylthiazol-5-yl)pyrazin-2-yl)-N-(4-hydroxybicyclo[2.2.1]heptan-1-yl)-4-methylbenzenesulfonamide;
3-(5-Amino-6-(1,3-dimethyl-1H-pyrazol-4-yl)pyrazin-2-yl)-N-(3-cyanobicyclo[1.1.1]pentan-1-yl)-4-methylbenzenesulfonamide;
3-(5-Amino-6-(1,3-dimethyl-1H-pyrazol-4-yl)pyrazin-2-yl)-N-(4-cyanobicyclo[2.1.1]hexan-1-yl)-4-methylbenzenesulfonamide;
3-(5-Amino-6-(1,3-dimethyl-1H-pyrazol-4-yl)pyrazin-2-yl)-N-(4-(hydroxymethyl)bicyclo[2.1.1]hexan-1-yl)-4-methylbenzenesulfonamide;
3-(5-amino-6-(1,3-dimethyl-1H-pyrazol-4-yl)pyrazin-2-yl)-N-(3-(hydroxymethyl)bicyclo[1.1.1]pentan-1-yl)-4-methylbenzenesulfonamide;
3-(5-Amino-6-(pyridin-3-yl)pyrazin-2-yl)-N-(4-hydroxybicyclo[2.2.1]heptan-1-yl)-4-methylbenzenesulfonamide;
3-(5-Amino-6-(pyridin-4-yl)pyrazin-2-yl)-N-(4-hydroxybicyclo[2.2.1]heptan-1-yl)-4-methylbenzenesulfonamide;
3-(5-Amino-6-(1H-1,2,4-triazol-1-yl)pyrazin-2-yl)-N-(3-cyanobicyclo[1.1.1]pentan-1-yl)-4-methylbenzenesulfonamide;
3-(5-Amino-6-(1H-1,2,4-triazol-1-yl)pyrazin-2-yl)-N-(3-(hydroxymethyl)bicyclo[1.1.1]pentan-1-yl)-4-methylbenzenesulfonamide;
3-(5-Amino-6-(1H-1,2,4-triazol-1-yl)pyrazin-2-yl)-N-(4-(hydroxymethyl)bicyclo[2.1.1]hexan-1-yl)-4-methylbenzenesulfonamide;
3-(5-Amino-6-(1H-1,2,4-triazol-1-yl)pyrazin-2-yl)-N-(4-hydroxybicyclo[2.2.1]heptan-1-yl)-4-methylbenzenesulfonamide;
3-(5-Amino-6-(1H-1,2,4-triazol-1-yl)pyrazin-2-yl)-N-(4-cyanobicyclo[2.1.1]hexan-1-yl)-4-methylbenzenesulfonamide;
3-(5-Amino-6-(1H-1,2,4-triazol-1-yl)pyrazin-2-yl)-N-(3-(2-hydroxypropan-2-yl)bicyclo[1.1.1]pentan-1-yl)-4-methylbenzenesulfonamide;
3-(5-Amino-6-(1H-1,2,4-triazol-1-yl)pyrazin-2-yl)-N-(4-hydroxybicyclo[2.1.1]hexan-1-yl)-4-methylbenzenesulfonamide;
(3-(3-(5-Amino-6-(1H-1,2,4-triazol-1-yl)pyrazin-2-yl)-4-methylphenylsulfonamido)bicyclo[1.1.1]pentan-1-yl) methyl methylcarbamate;
3-(3-(5-Amino-6-(1H-1,2,4-triazol-1-yl)pyrazin-2-yl)-4-methylphenyl sulfonamido)-N-methylbicyclo[1.1.1]pentane-1-carboxamide;
3-(3-(5-Amino-6-(1H-1,2,4-triazol-1-yl)pyrazin-2-yl)-4-methylphenyl sulfonamido)-N,N-dimethylbicyclo[1.1.1]pentane-1-carboxamide;
3-(5-Amino-6-(1H-1,2,4-triazol-1-yl)pyrazin-2-yl)-N-(3-(azetidine-1-carbonyl)bicyclo[1.1.1]pentan-1-yl)-4-methylbenzenesulfonamide;
3-(3-(5-Amino-6-(1H-1,2,4-triazol-1-yl)pyrazin-2-yl)-4-methylphenylsulfonamido)-N-(2,2,2-trifluoroethyl)bicyclo[1.1.1]pentane-1-carboxamide;
3-(5-Amino-6-(2H-tetrazol-5-yl)pyrazin-2-yl)-N-(3-cyanobicyclo[1.1.1]pentan-1-yl)-4-methylbenzenesulfonamide;
3-(5-Amino-6-(2H-tetrazol-5-yl)pyrazin-2-yl)-N-(4-cyanobicyclo[2.1.1]hexan-1-yl)-4-methylbenzenesulfonamide;

Ethyl 3-(3-(5-amino-6-(1H-1,2,4-triazol-1-yl)pyrazin-2-yl)-4-methylphenyl sulfonamido)bicyclo[1.1.1]pentan-1-ylcarbamate;

N-(3-(3-(5-Amino-6-(1H-1,2,4-triazol-1-yl)pyrazin-2-yl)-4-methylphenyl sulfonamido)bicyclo[1.1.1]pentan-1-yl)acetamide;

3-(5-Amino-6-(2H-1,2,3-triazol-2-yl)pyrazin-2-yl)-N-(3-cyanobicyclo[1.1.1]pentan-1-yl)-4-methylbenzenesulfonamide;

3-(5-Amino-6-(2H-1,2,3-triazol-2-yl)pyrazin-2-yl)-N-(4-cyanobicyclo[2.1.1]hexan-1-yl)-4-methylbenzenesulfonamide;

3-(5-Amino-6-(1H-1,2,3-triazol-1-yl)pyrazin-2-yl)-N-(3-cyanobicyclo[1.1.1]pentan-1-yl)-4-methylbenzenesulfonamide;

3-(5-Amino-6-(1H-1,2,3-triazol-1-yl)pyrazin-2-yl)-N-(4-cyanobicyclo[2.1.1]hexan-1-yl)-4-methylbenzenesulfonamide;

3-(5-Amino-6-(1-methyl-1H-1,2,4-triazol-3-yl)pyrazin-2-yl)-N-(3-cyanobicyclo[1.1.1]pentan-1-yl)-4-methylbenzenesulfonamide;

3-(5-Amino-6-(1-methyl-1H-1,2,4-triazol-3-yl)pyrazin-2-yl)-N-(4-cyanobicyclo[2.1.1]hexan-1-yl)-4-methylbenzenesulfonamide;

3-(5-Amino-6-(1H-1,2,4-triazol-1-yl)pyrazin-2-yl)-N-(4-hydroxybicyclo[2.2.1]heptan-1-yl)-4-(methyl-$d_3$)benzenesulfonamide;

3-(5-Amino-6-(1H-1,2,4-triazol-1-yl)pyrazin-2-yl)-N-(3-cyanobicyclo[1.1.1]pentan-1-yl)-4-(methyl-d3)benzenesulfonamide;

3-(5-Amino-6-(1H-1,2,4-triazol-1-yl)pyrazin-2-yl)-N-(3-(hydroxymethyl)bicyclo[1.1.1]pentan-1-yl)-4-(methyl-$d_3$)benzenesulfonamide;

3-(5-Amino-6-(2H-1,2,3-triazol-2-yl)pyrazin-2-yl)-N-(3-cyanobicyclo[1.1.1]pentan-1-yl)-4-(methyl-d3)benzenesulfonamide;

3-(5-Amino-6-(2H-1,2,3-triazol-2-yl)pyrazin-2-yl)-N-(3-(hydroxymethyl)bicyclo[1.1.1]pentan-1-yl)-4-(methyl-$d_3$)benzenesulfonamide;

3-(5-Amino-6-(1H-pyrazol-1-yl)pyrazin-2-yl)-N-(4-cyanobicyclo[2.1.1]hexan-1-yl)-4-methylbenzenesulfonamide;

3-(5-Amino-6-(1-methyl-1H-pyrazol-3-yl)pyrazin-2-yl)-N-(4-cyanobicyclo[2.1.1]hexan-1-yl)-4-(methyl-d3)benzenesulfonamide;

3-(5-Amino-6-(pyrimidin-5-yl)pyrazin-2-yl)-N-(4-cyanobicyclo[2.1.1]hexan-1-yl)-4-(methyl-$d_3$)benzenesulfonamide;

3-(5-Amino-6-(2-methylthiazol-5-yl)pyrazin-2-yl)-N-(4-cyanobicyclo[2.1.1]hexan-1-yl)-4-(methyl-$d_3$)benzenesulfonamide;

3-(5-Amino-6-(2-methyloxazol-5-yl)pyrazin-2-yl)-N-(4-cyanobicyclo[2.1.1]hexan-1-yl)-4-(methyl-$d_3$)benzenesulfonamide;

3-(5-Amino-6-(2-(dimethylamino)pyrimidin-5-yl)pyrazin-2-yl)-N-(4-cyanobicyclo[2.1.1]hexan-1-yl)-4-(methyl-$d_3$)benzenesulfonamide;

3-(5-Amino-6-(oxazol-5-yl)pyrazin-2-yl)-N-(4-cyanobicyclo[2.1.1]hexan-1-yl)-4-(methyl-$d_3$)benzenesulfonamide;

3-(5-Amino-6-(pyrimidin-2-yl)pyrazin-2-yl)-N-(4-cyanobicyclo[2.1.1]hexan-1-yl)-4-(methyl-$d_3$)benzenesulfonamide;

3-(5-Amino-6-(oxazol-2-yl)pyrazin-2-yl)-N-(4-cyanobicyclo[2.1.1]hexan-1-yl)-4-(methyl-$d_3$)benzenesulfonamide;

3-(5-Amino-6-(pyrimidin-4-yl)pyrazin-2-yl)-N-(4-cyanobicyclo[2.1.1]hexan-1-yl)-4-(methyl-$d_3$)benzenesulfonamide;

3-(5-Amino-6-(oxazol-5-yl)pyrazin-2-yl)-N-(3-cyanobicyclo[1.1.1]pentan-1-yl)-4-(methyl-$d_3$)benzenesulfonamide;

3-(5-Amino-6-(oxazol-5-yl)pyrazin-2-yl)-N-(4-hydroxybicyclo[2.1.1]hexan-1-yl)-4-(methyl-$d_3$)benzenesulfonamide;

3-(5-Amino-6-(oxazol-5-yl)pyrazin-2-yl)-N-(3-(hydroxymethyl)bicyclo[1.1.1]pentan-1-yl)-4-(methyl-$d_3$)benzenesulfonamide;

3-(5-Amino-6-(2-(methylthio)pyrimidin-4-yl)pyrazin-2-yl)-N-(3-cyanobicyclo[1.1.1]pentan-1-yl)-4-(methyl-$d_3$)benzenesulfonamide;

3-(5-Amino-6-(2-(methylthio)pyrimidin-4-yl)pyrazin-2-yl)-N-(4-hydroxybicyclo[2.1.1]hexan-1-yl)-4-(methyl-$d_3$)benzenesulfonamide;

3-(5-Amino-6-(2-(methylthio)pyrimidin-4-yl)pyrazin-2-yl)-N-(3-(hydroxymethyl)bicyclo[1.1.1]pentan-1-yl)-4-(methyl-$d_3$)benzenesulfonamide;

3-(5-Amino-6-(pyrimidin-4-yl)pyrazin-2-yl)-N-(3-cyanobicyclo[1.1.1]pentan-1-yl)-4-(methyl-$d_3$)benzenesulfonamide;

3-(5-Amino-6-(pyrimidin-4-yl)pyrazin-2-yl)-N-(4-hydroxybicyclo[2.1.1]hexan-1-yl)-4-(methyl-$d_3$)benzenesulfonamide;

3-(5-Amino-6-(pyrimidin-4-yl)pyrazin-2-yl)-N-(3-(hydroxymethyl)bicyclo[1.1.1]pentan-1-yl)-4-(methyl-$d_3$)benzenesulfonamide;

3-(6-Amino-5-(1,3-dimethyl-1H-pyrazol-4-yl)pyridin-3-yl)-N-(4-cyanobicyclo[2.1.1]hexan-1-yl)-4-methylbenzenesulfonamide;

3-(6-amino-5-(2-methylthiazol-5-yl)pyridin-3-yl)-N-(4-cyanobicyclo[2.1.1]hexan-1-yl)-4-methylbenzenesulfonamide; and 3-(6-amino-5-(2-methylthiazol-5-yl)pyridin-3-yl)-N-(3-(hydroxymethyl)bicyclo[1.1.1]pentan-1-yl)-4-methylbenzenesulfonamide;

or a pharmaceutically acceptable salt thereof.

40. A pharmaceutical composition comprising a compound of claim 1, or a pharmaceutically acceptable salt or a tautomer thereof, and a pharmaceutically acceptable excipient or carrier.

41. A method of inhibiting an activity of PI3Kγ kinase, comprising contacting the kinase with a compound of claim 1, or a pharmaceutically acceptable salt or a tautomer thereof.

42. The method of claim 41, wherein said compound, or a pharmaceutically acceptable salt thereof, is a selective inhibitor for PI3Kγ over one or more of PI3Kα, PI3Kβ, and PI3Kδ.

43. A method of treating a disease or disorder in a patient, wherein said disease or disorder is associated with abnormal expression or activity of PI3Kγ kinase, comprising administering to said patient a therapeutically effective amount of a compound of claim 1, or a pharmaceutically acceptable salt thereof.

44. The method of claim 43, wherein the disease or disorder is an autoimmune disease or disorder, cancer, cardiovascular disease, or neurodegenerative disease.

45. The method of claim 43, wherein disease or disorder is lung cancer, melanoma, pancreatic cancer, breast cancer, prostate cancer, liver cancer, color cancer, endometrial cancer, bladder cancer, skin cancer, cancer of the uterus, renal cancer, gastric cancer, seminoma, teratocarcinoma, astrocytoma, neuroblastoma, glioma, or sarcoma.

46. The method of claim 45, wherein the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

47. The method of claim 43, wherein the disease or disorder is acute myeloid leukemia, acute monocytic leukemia, small lymphocyctic lymphoma, chronic lymphocytic leukemia (CLL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma.

48. The method of claim 47, wherein the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma.

49. The method of claim 47, wherein the anaplastic large cell lymphoma (ALCL) is systemic ALCL or primary cutaneous ALCL.

50. The method of claim 43, wherein the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xenoderoma pigmentosum, keratoctanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

51. The method of claim 50, wherein the non-Hodgkin's lymphoma (NHL) is relapsed NHL, refractory NHL, recucurrent follicular NHL, indolent NHL (iNHL), or aggressive NHL (aNHL).

52. The method of claim 50, wherein the diffuse large B cell lymphoma is activated B-cell like (ABC) diffuse large B cell lymphoma, or germinal center B cell (GCB) diffuse large B cell lymphoma.

53. The method of claim 50, wherein the Burkitt's lymphoma is endemic Burkitt's lymphoma, sporadic Burkitt's lymphoma, or Burkitt's-like lymphoma.

54. The method of claim 43, wherein the disease or disorder is rheumatoid arthritis, multiple sclerosis, systemic lupus erythematous, asthma, allergy, allergic rhinitis, pancreatitis, psoriasis, anaphylaxis, glomerulonephritis, inflammatory bowel disease, thrombosis, meningitis, encephalitis, diabetic retinopathy, benign prostatic hypertrophy, myasthenia gravis, Sjögren's syndrome, osteoarthritis, restenosis, or atherosclerosis.

55. The method of claim 43, wherein the disease or disorder is heart hypertropy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia, bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

56. The method of claim 55, wherein the idiopathic thrombocytopenic purpura (ITP) is relapsed ITP or refractory ITP.

57. The method of claim 55, wherein the vasculitis is Behcet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or antineutrophil cytoplasm antibody associated (ANCA) systemic vasculitis (AASV).

58. The method of claim 43, wherein the disease or disorder is Alzheimer's disease, central nervous system trauma, or stroke.

* * * * *

UNITED STATES PATENT AND TRADEMARK OFFICE
CERTIFICATE OF CORRECTION

| | | |
|---|---|---|
| PATENT NO. | : 11,306,079 B2 | Page 1 of 3 |
| APPLICATION NO. | : 16/955240 | |
| DATED | : April 19, 2022 | |
| INVENTOR(S) | : Artem Shvartsbart et al. | |

It is certified that error appears in the above-identified patent and that said Letters Patent is hereby corrected as shown below:

In the Claims

Column 152, Line 38, Claim 1, delete "$C_{3-10}$cycloalkyl," and insert -- $C_{3-10}$ cycloalkyl, --;

Column 152, Line 46, Claim 1, delete "$NR^aR^{a}$'" and insert -- $NR^aR^a$, --;

Column 153, Line 61, Claim 1, delete "$NR^c(O)OR^c$, $NR^c(O)NR^cR^c$," and insert -- $NR^cC(O)OR^c$, $NR^cC(O)NR^cR^c$, --;

Column 153, Line 62, Claim 1, delete "$NR^c($" and insert -- $NR^cC($ --;

Column 153, Line 62, Claim 1, delete "$NR^{c}$" and insert -- $NR^{oc}C$ --;

Column 153, Line 63, Claim 1, delete "$NR^c($" and insert -- $NR^cC($ --;

Column 155, Line 31, Claim 1, delete "5+-14" and insert -- 5-14 --;

Column 155, Line 36 Claim 1, delete "3m" and insert -- 3, --;

Column 156, Line 18, Claim 1, delete "6," and insert -- 6-, --;

Column 157, Line 44, Claim 23, delete "(dimethyl amino)" and insert -- (dimethylamino) --;

Column 158, Line 23-24, Claim 28, delete "—O— carbamyl," and insert -- —O—carbamyl, --;

Column 158, Line 46, Claim 28, delete "$NR^nR^{n}$'" and insert -- $NR^nR^n$, --;

Column 158, Line 46, Claim 28, delete "$NR^1C$" and insert -- $NR^nC$ --;

Signed and Sealed this
Twelfth Day of August, 2025

Coke Morgan Stewart
*Acting Director of the United States Patent and Trademark Office*

CERTIFICATE OF CORRECTION (continued)
U.S. Pat. No. 11,306,079 B2

Column 158, Line 59, Claim 28, delete "NR$^c$(O)R$^c$, NR$^c$(O)OR$^c$, NR$^c$" and insert -- NR$^c$C(O)R$^c$, NR$^c$C(O)OR$^c$, NR$^c$C --;

Column 158, Line 60, Claim 28, delete "NR$^c$" and insert -- NR$^c$C --;

Column 158, Line 61, Claim 28, delete "NR$^c$(=NOH)" and insert -- NR$^c$C(=NOH) --;

Column 158, Line 61, Claim 28, delete "NR$^c$(=NCN)" and insert -- NR$^c$C(=NCN) --;

Column 160, Line 2, Claim 28, delete "6," and insert -- 6-, --;

Column 160, Line 22, Claim 29, delete "NR$^n$R$^n$" and insert -- NR$^n$R$^n$, --;

Column 160, Line 53, Claim 29, delete "6," and insert -- 6-, --;

Column 164, Line 23, Claim 39, delete "(pyri din" and insert -- (pyridin --;

Column 164, Line 51, Claim 39, delete "methylphenyl sulfonamido)" and insert -- methylphenylsulfonamido) --;

Column 164, Line 54, Claim 39, delete "methylphenyl sulfonamido)" and insert -- methylphenylsulfonamido) --;

Column 165, Line 2, Claim 39, delete "methylphenyl sulfonamido)" and insert -- methylphenylsulfonamido) --;

Column 165, Line 5, Claim 39, delete "methylphenyl sulfonamido)" and insert -- methylphenylsulfonamido) --;

Column 165, Line 30, Claim 39, delete "(methyl-d3)" and insert -- (methyl-d$_3$) --;

Column 165, Line 36, Claim 39, delete "(methyl-d3)" and insert -- (methyl-d$_3$) --;

Column 165, Line 45, Claim 39, delete "(methyl-d3)" and insert -- (methyl-d$_3$) --;

Column 167, Line 17, Claim 47, delete "lymphocyctic" and insert -- lymphocytic --;

Column 167, Line 19, Claim 47, delete "actute lymphoblasic" and insert -- acute lymphoblastic --;

Column 167, Line 28, Claim 48, delete "naplastic" and insert -- anaplastic --;

Column 167, Line 39, Claim 50, delete "xenoderoa pigmentosum," and insert -- xeroderma pigmentosum, --;

Column 167, Line 39, Claim 50, delete "keratoctanthoma," and insert -- keratoacanthoma, --;

CERTIFICATE OF CORRECTION (continued)
U.S. Pat. No. 11,306,079 B2

Column 168, Lines 2-3, Claim 1, delete "recucurrent" and insert -- recurrent --; and Column 168, Line 21, Claim 55, delete "hypertropy," and insert -- hypertrophy, --.